United States Patent
Ge et al.

(10) Patent No.: US 9,365,871 B2
(45) Date of Patent: *Jun. 14, 2016

(54) **METHOD OF USING α-AMYLASE FROM *ASPERGILLUS CLAVATUS* FOR SACCHARIFICATION**

(71) Applicant: DANISCO US INC., Palo Alto, CA (US)

(72) Inventors: Jing Ge, Shanghai (CN); Ling Hua, Shanghai (CN); Martijn Silvan Scheffers, Leiden (NL); Zhongmei Tang, Shanghai (CN); Marco Van Brussel-Zwijnen, Zoetermeer (NL); Casper Vroemen, Oegstgeest (NL); Bo Zhang, Shanghai (CN); Kathleen A. Clarkson, San Francisco, CA (US); Jacquelyn A. Huitink, Burlingame, CA (US); Paula Johanna Maria Teunissen, Saratoga, CA (US)

(73) Assignee: Danisco US Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/561,085

(22) Filed: Dec. 4, 2014

(65) Prior Publication Data

US 2015/0152442 A1 Jun. 4, 2015

Related U.S. Application Data

(62) Division of application No. 13/888,303, filed on May 6, 2013, now Pat. No. 8,945,889.

(30) Foreign Application Priority Data

May 11, 2012 (WO) ................ PCT/CN2012/075352

(51) Int. Cl.
*C12P 19/14* (2006.01)
*C12C 7/04* (2006.01)
*C12P 7/14* (2006.01)

(52) U.S. Cl.
CPC ... *C12P 7/14* (2013.01); *C12C 7/04* (2013.01); *C12P 19/14* (2013.01); *C12P 2201/00* (2013.01)

(58) Field of Classification Search
CPC .................................. C12P 19/14; C12C 7/04
USPC ......................................................... 435/151
See application file for complete search history.

(56) References Cited

U.S. PATENT DOCUMENTS

2006/0075522 A1* 4/2006 Cleveland et al. ............ 800/289

* cited by examiner

*Primary Examiner* — Maryam Monshipouri
(74) *Attorney, Agent, or Firm* — Danisco US Inc.

(57) ABSTRACT

A fungal α-amylase is provided from *Aspergillus clavatus* (AcAmy1). AcAmy1 has an optimal pH of 4.5 and is operable at 30-75° C., allowing the enzyme to be used in combination with a glucoamylase in a saccharification reaction. This obviates the necessity of running a saccharification reaction as a batch process, where the pH and temperature must be readjusted for optimal use of the α-amylase or glucoamylase. AcAmy1 also catalyzes the saccharification of starch substrates to an oligosaccharide composition significantly enriched in DP2 and (DP1+DP2) compared to the products of saccharification catalyzed by an α-amylase from *Aspergillus kawachii*. This facilitates the utilization of the oligosaccharide composition by a fermenting organism in a simultaneous saccharification and fermentation process, for example.

15 Claims, 6 Drawing Sheets

FIG. 1A

```
SEQ ID NO:  1    20  LTPAEWRGQSIYFLITDRFARTDGSTTAPCDLSQRAY  56
SEQ ID NO:  4    20  LSAAEWRSQSIYFLLTDRFARTDGSTSAPCDLSQRAY  56
SEQ ID NO:  5    20  LDADGWRSQSIYFLLTDRFARTDGSTTAACDLAQRRY  56
SEQ ID NO: 12    24  LTPAEWRSQSIYFLLTDRFGREDNSTTAACDVTQRLY  60
SEQ ID NO: 13    21  LTPAEWRSQSIYFLLTDRFGRTDNSTTAACDTSDRVY  57
                      *   ** ****** **** * *  ** * **     * *

57  CGGSWQGIIKQLDYIQGMGFTAIWITPITEQIPQDTAEGSAFHGYWQKDIYNVNSHFGTA  116
 57  CGGSWQGIIDHLDYIQGMGFTAVWITPITKQIPQATSEGSGYHGYWQQDIYSVNSNFGTA  116
 57  CGGSWQGIINQLDYIQDMGFTAIWITPITEQIPDVTAVGTGFHGYWQKNIYGVDTNLGTA  116
 61  CGGSWQGIINHLDYIQGMGFTAIWITPVTEQFYENTGDGTSYHGYWQQNIHEVNANYGTA  120
 58  CGGSWQGIINQLDYIQGMGFTAIWITPVTGQFYENTGDGTSYHGYWQQDIYDLNYNYGTA  117
     *********  ***** ***** ****  * *     *  *  *****  *     ***

117  DDIRALSKALHDRGMYLMIDVVANHMGYNGPGASTDFSTFTPFNSASYFHSYCPINNYND  176
117  DDIRALSKALHDKGMYLMIDVVANHMGYNGPGASTDFSVFTPFNSASYFHSYCPISNYDD  176
117  DDIRALSEALHDRGMYLMLDVVANHMSYGGPGGSTDFSIFTPFDSASYFHSYCAINNYDN  176
121  QDLRDLANALHARGMYLMVDVVANHMGYNGAGNSVNYGVFTPFDSATYFHPYCLITDYNN  180
118  QDLKNLANALHERGMYLMVDVVANHMGYDGAGNTVDYSVFNPFSSSSYFHPYCLISNYDN  177
      *   *  *** ****** *******  *  *       *  ** * *** ** *  *

177  QSQVENCWLGDNTVALADLYTQHSDVRNIWYSWIKEIVGNYSADGLRIDTVKHVEKDFWT  236
177  QNQVENCWLGDDTVSLTDLYTQSNQVRNIWYSWVKDLVANYTVDGLRIDTVKHVEKDFWT  236
177  QWQVENCFLGDDTVSLTDLNTQSSEVRDIWYDWIEDIVANYSVDGLRIDTVKHVEKDFWP  236
181  QTAVEDCWLGDTTVSLPDLDTTSTAVRSIWYDWVKGLVANYSIDGLRIDTVKHVEKDFWP  240
178  QTNVEDCWLGDTTVSLPDLDTTSTAVRNIWYDWVADLVANYSIDGLRVDTVKHVEKDFWP  237
      *  ** * ***  **  *    **  ** *     * **  **** ************

237  GYTQAAGVYTVGEVLDGDPAYTCPYQGYVDGVLNYPIYYPLLRAFESSSGSMGDLYNMIN  296
237  GYREAAGVYTVGEVLHGDPAYTCPYQGYVDGVFNYPIYYPLLNAFKSSSGSISDLVNMIN  296
237  GYIDAAGVYSVGEIFHGDPAYTCPYQDYMDGVMNYPIYYPLLNAFKSSSGSMSDLYNMIN  296
241  GYNDAAGVYCVGEVFSGDPQYTCPYQNYLDGVLNYPIYYQLLYAFQSTSGSISNLYNMIS  300
238  GYNSAAGVYCVGEVYSGDPAYTCPYQNYMDGVLNYPIYYQLLYAFESSSGSISDLYNMIS  297
     **  ***** ***   *** ******  * ***  ***** ** ** ** * *  ****

297  SVASDCKDPTVLGSFIENHDNPRFASYTKDMSQAKAVISYVILSDGIPIIYSGQEQHYSG  356
297  TVSSDCKDPSLLGSFIENHDNPRFPSYSDMSQAKSVIAYVFFADGIPTIYSGQEQHYTG  356
297  TVASNCRDPTLLGNFIENHDNPRFPNYTPDMSRAKNVLAFLFLTDGIPIVYAGQEQHYSG  356
301  SVASDCADPTLLGNFIENHDNPRFASYTSDYSQAKNVISFMFFSDGIPIVYAGQEQHYSG  360
298  SVASSCKDPTLLGNFIENHDNPRFASYTSDYSQAKNVITFIFLSDGIPIVYAGQEQHYSG  357
      *   * ** * ** **********  *    **  *        ****  * ****** *
```

FIG. 1B

```
357 GNDPYNREAIWLSGYSTTSELYKFIATTNKIRQLAISKDSSYLTSRNNPFYTDSNTIAMR 416
357 GNDPYNREAIWLSGYATDSELYKFITTANKIRNLAISKDSSYLTTRNNAFYTDSNTIAMR 416
357 SNDPYNREPVWWSSYSTSSELYKFIATTNKIRKLAISKDSSYLTSRNTPFYSDSNYIAMR 416
361 GADPANREAVWLSGYSTSATLYSWIASTNKIRKLAISKDSAYITSKNNPFYYDSNTLAMR 420
358 GSDPANREATWLSGYSTSATLYTWIATTNQIRSLAISKDAGYVQAKNNPFYSDSNTIAMR 417
         ** ***    *  *  *     **   *    * ** ****** *       *   ** ***  ***

417 KG-SGGSQVITVLSNSGSNGGSYTLNLGNSGYSSGANLVEVYTCSSVTVGSDGKIPVPMA 475
417 KG-SSGSQVITVLSNSGSNGASYTLELANQGYNSGAQLIEVYTCSSVKVDSNGNIPVPMT 475
417 KG-SGGSQVLTLLNNIGTSIGSYTFDLYDHGYNSGANLVELYTCSSVQVGSNGAISIPMT 475
421 KGSVAGSQVITVLSNKGSSGSSYTLSLSGTGYSAGATLVEMYTCTTLTVDSSGNLAVPMV 480
418 KGTTAGAQVITVLSNKGASGSSYTLSLSGTGYSAGATLVETYTCTTVTVDSSGNLPVPMT 477
    **       *  * **  *  *     ***   *     ** ** * * ***     *  *  *   **

476 SGLPRVLVPASWMSGSGLCGSS 497    STTTLVTATTTPTGSSSSTTLATAVTTPTGS 528
476 SGLPRVLVPASWVTGSGLCGTS 497    SG---------TPSSTTLTTTMSLASST-TSS 519
476 SGLPRVLVPAAWVSGSGLCGLT 497    NP---------------TSKTTTATTTSTTTCA 515
481 SGLPRVFVPSSWVSGSGLCGDS 502    IS-------------TTATAPSATTSATATRTA 522
478 SGLPRVFVPSSWVNGSALCN-- 497    ---------------------------------TE 499
    ****** **  *  ** **

Linker

529 CKTATTVPVVLEESVRTSYGENIFISGSIPQLGSWNPDKAVALSSSQYTSSNPLWAVTLD 588
520 CVSATSLPITFNELVTTSYGENIFIAGSIPQLGNWNSANAVPLASTQYTSTNPVWSVSLD 579
516 SATATAITVVFQERVQTAYGENVFLAGSISQLGNWDTTEAVALSAAQYTATDPLWTVAIE 575
523 CAAATAIPILFEELVTTTYGESIYLTGSISQLGNWDTSSAIALSASKYTSSNPEWYVTVT 582
500 CTAATSISVLFEELVTTTYGENIYLSGSISQLGSWNTASAVALSASQYTSSNPEWYVSVT 559
         **      *  *  ***   *** *** *    *     **     *  *   *

589 LPVGTSFEYKFLKKEQNGGVAWENDPNRSYTVPEACAGTSQKVDSSWR 636  SEQ ID NO: 1
580 LPVGSTFQYKFMKKEKDGSVVWESDPNRSYTVGNGCTGAKYTVNDSWR 627  SEQ ID NO: 4
576 LPVGTSFEFKFLKKRQDGSIVWESNPNRSAKVNEGCARTTQTISTSWR 623  SEQ ID NO: 5
583 LPVGTSFEYKFVKKGSDGSIAWESDPNRSYTVPTGCAGTTVTVSDTWR 630  SEQ ID NO: 12
560 LPVGTSFQYKFIKKGSDGSVVWESDPNRSYTVPAGCEGATVTVADTWR 607  SEQ ID NO: 13
    ****  *  ** **  *   ** ****  *      *        **

Carbohydrate Binding Domain
```

SEQUENCE LISTING

```
<160> NUMBER OF SEQ ID NOS: 13

<210> SEQ ID NO 1
<211> LENGTH: 636
<212> TYPE: PRT
<213> ORGANISM: Aspergillus clavatus
<220> FEATURE:
<221> NAME/KEY: misc_feature
<222> LOCATION: (1)..(636)
<223> OTHER INFORMATION: Protein sequence of wild-type AcAmy1

<400> SEQUENCE: 1

Met Lys Leu Leu Ala Leu Thr Thr Ala Phe Ala Leu Leu Gly Lys Gly
1               5                   10                  15

Val Phe Gly Leu Thr Pro Ala Glu Trp Arg Gly Gln Ser Ile Tyr Phe
                20                  25                  30

Leu Ile Thr Asp Arg Phe Ala Arg Thr Asp Gly Ser Thr Thr Ala Pro
            35                  40                  45

Cys Asp Leu Ser Gln Arg Ala Tyr Cys Gly Gly Ser Trp Gln Gly Ile
        50                  55                  60

Ile Lys Gln Leu Asp Tyr Ile Gln Gly Met Gly Phe Thr Ala Ile Trp
65                  70                  75                  80

Ile Thr Pro Ile Thr Glu Gln Ile Pro Gln Asp Thr Ala Glu Gly Ser
                85                  90                  95

Ala Phe His Gly Tyr Trp Gln Lys Asp Ile Tyr Asn Val Asn Ser His
            100                 105                 110

Phe Gly Thr Ala Asp Asp Ile Arg Ala Leu Ser Lys Ala Leu His Asp
        115                 120                 125

Arg Gly Met Tyr Leu Met Ile Asp Val Val Ala Asn His Met Gly Tyr
    130                 135                 140

Asn Gly Pro Gly Ala Ser Thr Asp Phe Ser Thr Phe Thr Pro Phe Asn
145                 150                 155                 160

Ser Ala Ser Tyr Phe His Ser Tyr Cys Pro Ile Asn Asn Tyr Asn Asp
                165                 170                 175

Gln Ser Gln Val Glu Asn Cys Trp Leu Gly Asp Asn Thr Val Ala Leu
            180                 185                 190
```

```
Ala Asp Leu Tyr Thr Gln His Ser Asp Val Arg Asn Ile Trp Tyr Ser
            195                 200                 205

Trp Ile Lys Glu Ile Val Gly Asn Tyr Ser Ala Asp Gly Leu Arg Ile
        210                 215                 220

Asp Thr Val Lys His Val Glu Lys Asp Phe Trp Thr Gly Tyr Thr Gln
225                 230                 235                 240

Ala Ala Gly Val Tyr Thr Val Gly Glu Val Leu Asp Gly Asp Pro Ala
                245                 250                 255

Tyr Thr Cys Pro Tyr Gln Gly Tyr Val Asp Gly Val Leu Asn Tyr Pro
                260                 265                 270

Ile Tyr Tyr Pro Leu Leu Arg Ala Phe Glu Ser Ser Ser Gly Ser Met
        275                 280                 285

Gly Asp Leu Tyr Asn Met Ile Asn Ser Val Ala Ser Asp Cys Lys Asp
        290                 295                 300

Pro Thr Val Leu Gly Ser Phe Ile Glu Asn His Asp Asn Pro Arg Phe
305                 310                 315                 320

Ala Ser Tyr Thr Lys Asp Met Ser Gln Ala Lys Ala Val Ile Ser Tyr
                325                 330                 335

Val Ile Leu Ser Asp Gly Ile Pro Ile Ile Tyr Ser Gly Gln Glu Gln
                340                 345                 350

His Tyr Ser Gly Gly Asn Asp Pro Tyr Asn Arg Glu Ala Ile Trp Leu
        355                 360                 365

Ser Gly Tyr Ser Thr Thr Ser Glu Leu Tyr Lys Phe Ile Ala Thr Thr
        370                 375                 380

Asn Lys Ile Arg Gln Leu Ala Ile Ser Lys Asp Ser Ser Tyr Leu Thr
385                 390                 395                 400

Ser Arg Asn Asn Pro Phe Tyr Thr Asp Ser Asn Thr Ile Ala Met Arg
                405                 410                 415

Lys Gly Ser Gly Gly Ser Gln Val Ile Thr Val Leu Ser Asn Ser Gly
                420                 425                 430

Ser Asn Gly Gly Ser Tyr Thr Leu Asn Leu Gly Asn Ser Gly Tyr Ser
        435                 440                 445

Ser Gly Ala Asn Leu Val Glu Val Tyr Thr Cys Ser Ser Val Thr Val
        450                 455                 460

Gly Ser Asp Gly Lys Ile Pro Val Pro Met Ala Ser Gly Leu Pro Arg
465                 470                 475                 480

Val Leu Val Pro Ala Ser Trp Met Ser Gly Gly Leu Cys Gly Ser
                485                 490                 495

Ser Ser Thr Thr Thr Leu Val Thr Ala Thr Thr Pro Thr Gly Ser
        500                 505                 510

Ser Ser Ser Thr Thr Leu Ala Thr Ala Val Thr Thr Pro Thr Gly Ser
        515                 520                 525

Cys Lys Thr Ala Thr Thr Val Pro Val Val Leu Glu Glu Ser Val Arg
        530                 535                 540

Thr Ser Tyr Gly Glu Asn Ile Phe Ile Ser Gly Ser Ile Pro Gln Leu
545                 550                 555                 560

Gly Ser Trp Asn Pro Asp Lys Ala Val Ala Leu Ser Ser Ser Gln Tyr
                565                 570                 575

Thr Ser Ser Asn Pro Leu Trp Ala Val Thr Leu Asp Leu Pro Val Gly
                580                 585                 590

Thr Ser Phe Glu Tyr Lys Phe Leu Lys Lys Glu Gln Asn Gly Gly Val
            595                 600                 605
```

```
Ala Trp Glu Asn Asp Pro Asn Arg Ser Tyr Thr Val Pro Glu Ala Cys
    610                 615                 620

Ala Gly Thr Ser Gln Lys Val Asp Ser Ser Trp Arg
625                 630                 635

<210> SEQ ID NO 2
<211> LENGTH: 2316
<212> TYPE: DNA
<213> ORGANISM: Aspergillus clavatus
<220> FEATURE:
<221> NAME/KEY: misc_feature
<222> LOCATION: (1)..(2316)
<223> OTHER INFORMATION: Nucleotide sequence of AcAmy1 gene

<400> SEQUENCE: 2
```

| | | | | | |
|---|---|---|---|---|---|
| atgaagcttc | tagctttgac | aactgccttc | gccctgttgg | gcaaaggggt | atttggtcta    60 |
| actccggccg | aatggcgggg | ccagtctatc | tacttcctga | taacggaccg | gtttgctcgt   120 |
| acagatggct | caacaaccgc | tccatgtgat | ctcagccaga | gggttagtga | tttcatcgta   180 |
| ttctttgtca | tgtgtcatga | cgctgacgat | ttcaggcgta | ctgtggtgga | agctggcagg   240 |
| gtattatcaa | gcaagtaagc | ctactggttt | ccaattttgt | tgaattcctt | tctgactcgg   300 |
| ccagctcgat | tatatccaag | gaatgggctt | cactgctatt | tggatcacac | ccattacgga   360 |
| gcaaatccca | caggataccg | ctgaaggatc | agcattccac | ggctattggc | agaaggatat   420 |
| gtgagtttcc | ttataacatt | cactacgttt | tgctaatata | gaacagttac | aatgtcaact   480 |
| cccatttcgg | aaccgccgat | gacattcggg | cattgtccaa | ggcccttcac | gacaggggaa   540 |
| tgtacctgat | gattgacgtt | gttgccaacc | acatggtagg | tgatatctca | ctgattgagt   600 |
| tataccattc | ctactgacag | cccgacctca | acaaagggt  | tacaatggac | ctggtgcctc   660 |
| gactgatttt | agcacccttta | ccccgttcaa | ctctgcctcc | tacttccact | cgtactgccc   720 |
| gatcaacaac | tataacgacc | agtctcaggt | agagaactgt | tggttgggag | acaacactgt   780 |
| ggctctggca | gacctataca | cccagcattc | ggatgtgcgg | aacatctggt | acagctggat   840 |
| caaagaaatt | gttggcaatt | actctggtta | gtaatccaat | ccaagtcccg | tccctggcg    900 |
| tctttcagaa | ctaacagaaa | cagctgatgg | tctgcgtatc | gacaccgtca | agcacgttga   960 |
| aaaggatttc | tggactggct | cacccaagc  | tgctggtgtt | tataccgttg | gcgaggtatt  1020 |
| agatggggac | ccggcttata | cctgccccta | tcagggatat | gtggacggtg | tcctgaatta  1080 |
| tcccatgtga | gttcacccctt | tcatatacag | attgatgtac | taaccaatca | gctattatcc  1140 |
| cctcctgaga | gcgttcgaat | cgtcgagtgg | tagcatgggt | gatctttaca | atatgatcaa  1200 |
| ctctgtggcc | tcggattgta | aagacccac  | cgtgctagga | agtttcattg | agaaccatga  1260 |
| caatcctcgc | ttcgctaggt | aggccaatac | tgacatagga | aaggagaaga | ggctaactgt  1320 |
| tgcagctata | ccaaggatat | gtcccaggcc | aaggctgtta | ttagctatgt | catactatcg  1380 |
| gacggaatcc | ccatcatcta | ttctggacag | gagcagcact | actctggtgg | aaatgacccg  1440 |
| tacaaccgcg | aagctatctg | gttgtcgggt | tactctacca | cctcagagct | gtataaattc  1500 |
| attgccacca | cgaacaagat | ccgtcagctc | gccatttcaa | aggattcaag | ctatcttact  1560 |
| tcacgagtat | gtgttctggc | cagactcaca | ctgcaatact | aaccggtata | gaacaatccc  1620 |
| ttctacactg | atagcaacac | cattgcaatg | cgaaagggct | ccgggggctc | gcaggtcatc  1680 |
| actgtacttt | ccaactctgg | ttccaacggt | ggatcgtaca | cgctcaactt | gggtaacagc  1740 |
| ggatactcgt | ctggagccaa | tctagtggag | gtgtacacct | gctcgtctgt | cacggtcggt  1800 |
| tccgacggca | agatccccgt | ccccatggca | tctggtcttc | ccgtgtcct  | tgttccggca  1860 |

```
tcttggatgt ccggaagtgg attgtgcggc agctcttcca ccactaccct cgtcaccgcc      1920
accacgactc caactggcag ctcttccagc actaccctcg ccaccgccgt cacgactcca      1980
actggtagct gcaaaactgc gacgaccgtt ccagtggtcc ttgaagagag cgtgagaaca      2040
tcctacggcg agaacatctt catctccggc tccatccctc agctcggtag ctggaacccg      2100
gataaagcag tcgctctttc ttccagccag tacacttcgt cgaatccttt gtgggccgtc      2160
actctcgacc tccccgtggg aacttcgttt gaatacaaat tcctcaagaa ggagcagaat      2220
ggtggcgtcg cttgggagaa tgaccctaac cggtcttaca ctgttcccga agcgtgtgcc      2280
ggtacctccc aaaaggtgga cagctcttgg aggtga                                2316

<210> SEQ ID NO 3
<211> LENGTH: 19
<212> TYPE: PRT
<213> ORGANISM: Aspergillus clavatus
<220> FEATURE:
<221> NAME/KEY: misc_feature
<222> LOCATION: (1)..(19)
<223> OTHER INFORMATION: Amino acid sequence of the AcAmy1 signal
      peptide

<400> SEQUENCE: 3

Met Lys Leu Leu Ala Leu Thr Thr Ala Phe Ala Leu Leu Gly Lys Gly
1               5                   10                  15

Val Phe Gly

<210> SEQ ID NO 4
<211> LENGTH: 627
<212> TYPE: PRT
<213> ORGANISM: Talaromyces stipitatus
<220> FEATURE:
<221> NAME/KEY: misc_feature
<222> LOCATION: (1)..(627)
<223> OTHER INFORMATION: Putative alpha-amylase from Talaromyces
      stipitatus ATCC 10500

<400> SEQUENCE: 4

Met Lys Leu Ser Leu Leu Ala Thr Thr Leu Pro Leu Phe Gly Lys Ile
1               5                   10                  15

Val Asp Ala Leu Ser Ala Ala Glu Trp Arg Ser Gln Ser Ile Tyr Phe
                20                  25                  30

Leu Leu Thr Asp Arg Phe Ala Arg Thr Asp Gly Ser Thr Ser Ala Pro
            35                  40                  45

Cys Asp Leu Ser Gln Arg Ala Tyr Cys Gly Gly Ser Trp Gln Gly Ile
        50                  55                  60

Ile Asp His Leu Asp Tyr Ile Gln Gly Met Gly Phe Thr Ala Val Trp
65                  70                  75                  80

Ile Thr Pro Ile Thr Lys Gln Ile Pro Gln Ala Thr Ser Glu Gly Ser
                85                  90                  95

Gly Tyr His Gly Tyr Trp Gln Gln Asp Ile Tyr Ser Val Asn Ser Asn
                100                 105                 110

Phe Gly Thr Ala Asp Asp Ile Arg Ala Leu Ser Lys Ala Leu His Asp
            115                 120                 125

Lys Gly Met Tyr Leu Met Ile Asp Val Val Ala Asn His Met Gly Tyr
        130                 135                 140

Asn Gly Pro Gly Ala Ser Thr Asp Phe Ser Val Phe Thr Pro Phe Asn
145                 150                 155                 160

Ser Ala Ser Tyr Phe His Ser Tyr Cys Pro Ile Ser Asn Tyr Asp Asp
                165                 170                 175
```

```
Gln Asn Gln Val Glu Asn Cys Trp Leu Gly Asp Asp Thr Val Ser Leu
            180                 185                 190
Thr Asp Leu Tyr Thr Gln Ser Asn Gln Val Arg Asn Ile Trp Tyr Ser
        195                 200                 205
Trp Val Lys Asp Leu Val Ala Asn Tyr Thr Val Asp Gly Leu Arg Ile
    210                 215                 220
Asp Thr Val Lys His Val Glu Lys Asp Phe Trp Thr Gly Tyr Arg Glu
225                 230                 235                 240
Ala Ala Gly Val Tyr Thr Val Gly Glu Val Leu His Gly Asp Pro Ala
            245                 250                 255
Tyr Thr Cys Pro Tyr Gln Gly Tyr Val Asp Gly Val Phe Asn Tyr Pro
        260                 265                 270
Ile Tyr Tyr Pro Leu Leu Asn Ala Phe Lys Ser Ser Gly Ser Ile
    275                 280                 285
Ser Asp Leu Val Asn Met Ile Asn Thr Val Ser Ser Asp Cys Lys Asp
290                 295                 300
Pro Ser Leu Leu Gly Ser Phe Ile Glu Asn His Asp Asn Pro Arg Phe
305                 310                 315                 320
Pro Ser Tyr Thr Ser Asp Met Ser Gln Ala Lys Ser Val Ile Ala Tyr
        325                 330                 335
Val Phe Phe Ala Asp Gly Ile Pro Thr Ile Tyr Ser Gly Gln Glu Gln
            340                 345                 350
His Tyr Thr Gly Gly Asn Asp Pro Tyr Asn Arg Glu Ala Ile Trp Leu
        355                 360                 365
Ser Gly Tyr Ala Thr Asp Ser Glu Leu Tyr Lys Phe Ile Thr Thr Ala
    370                 375                 380
Asn Lys Ile Arg Asn Leu Ala Ile Ser Lys Asp Ser Ser Tyr Leu Thr
385                 390                 395                 400
Thr Arg Asn Asn Ala Phe Tyr Thr Asp Ser Asn Thr Ile Ala Met Arg
            405                 410                 415
Lys Gly Ser Ser Gly Ser Gln Val Ile Thr Val Leu Ser Asn Ser Gly
        420                 425                 430
Ser Asn Gly Ala Ser Tyr Thr Leu Glu Leu Ala Asn Gln Gly Tyr Asn
    435                 440                 445
Ser Gly Ala Gln Leu Ile Glu Val Tyr Thr Cys Ser Ser Val Lys Val
450                 455                 460
Asp Ser Asn Gly Asn Ile Pro Val Pro Met Thr Ser Gly Leu Pro Arg
465                 470                 475                 480
Val Leu Val Pro Ala Ser Trp Val Thr Gly Ser Gly Leu Cys Gly Thr
            485                 490                 495
Ser Ser Gly Thr Pro Ser Ser Thr Thr Leu Thr Thr Met Ser Leu
        500                 505                 510
Ala Ser Ser Thr Thr Ser Ser Cys Val Ser Ala Thr Ser Leu Pro Ile
    515                 520                 525
Thr Phe Asn Glu Leu Val Thr Thr Ser Tyr Gly Glu Asn Ile Phe Ile
530                 535                 540
Ala Gly Ser Ile Pro Gln Leu Gly Asn Trp Asn Ser Ala Asn Ala Val
545                 550                 555                 560
Pro Leu Ala Ser Thr Gln Tyr Thr Ser Thr Asn Pro Val Trp Ser Val
            565                 570                 575
Ser Leu Asp Leu Pro Val Gly Ser Thr Phe Gln Tyr Lys Phe Met Lys
        580                 585                 590
```

```
Lys Glu Lys Asp Gly Ser Val Val Trp Glu Ser Asp Pro Asn Arg Ser
            595                 600                 605

Tyr Thr Val Gly Asn Gly Cys Thr Gly Ala Lys Tyr Thr Val Asn Asp
610                 615                 620

Ser Trp Arg
625

<210> SEQ ID NO 5
<211> LENGTH: 623
<212> TYPE: PRT
<213> ORGANISM: Aspergillus nidulans
<220> FEATURE:
<221> NAME/KEY: misc_feature
<222> LOCATION: (1)..(623)
<223> OTHER INFORMATION: Protein AN3402.2 from Aspergillus nidulans
      FGSC A4

<400> SEQUENCE: 5

Met Arg Leu Leu Ala Leu Thr Ser Ala Leu Ala Leu Leu Gly Lys Ala
1               5                   10                  15

Val His Gly Leu Asp Ala Asp Gly Trp Arg Ser Gln Ser Ile Tyr Phe
                20                  25                  30

Leu Leu Thr Asp Arg Phe Ala Arg Thr Asp Gly Ser Thr Thr Ala Ala
            35                  40                  45

Cys Asp Leu Ala Gln Arg Arg Tyr Cys Gly Gly Ser Trp Gln Gly Ile
        50                  55                  60

Ile Asn Gln Leu Asp Tyr Ile Gln Asp Met Gly Phe Thr Ala Ile Trp
65                  70                  75                  80

Ile Thr Pro Ile Thr Glu Gln Ile Pro Asp Val Thr Ala Val Gly Thr
                85                  90                  95

Gly Phe His Gly Tyr Trp Gln Lys Asn Ile Tyr Gly Val Asp Thr Asn
            100                 105                 110

Leu Gly Thr Ala Asp Asp Ile Arg Ala Leu Ser Glu Ala Leu His Asp
        115                 120                 125

Arg Gly Met Tyr Leu Met Leu Asp Val Val Ala Asn His Met Ser Tyr
130                 135                 140

Gly Gly Pro Gly Gly Ser Thr Asp Phe Ser Ile Phe Thr Pro Phe Asp
145                 150                 155                 160

Ser Ala Ser Tyr Phe His Ser Tyr Cys Ala Ile Asn Asn Tyr Asp Asn
                165                 170                 175

Gln Trp Gln Val Glu Asn Cys Phe Leu Gly Asp Asp Thr Val Ser Leu
            180                 185                 190

Thr Asp Leu Asn Thr Gln Ser Ser Glu Val Arg Asp Ile Trp Tyr Asp
        195                 200                 205

Trp Ile Glu Asp Ile Val Ala Asn Tyr Ser Val Asp Gly Leu Arg Ile
210                 215                 220

Asp Thr Val Lys His Val Glu Lys Asp Phe Trp Pro Gly Tyr Ile Asp
225                 230                 235                 240

Ala Ala Gly Val Tyr Ser Val Gly Glu Ile Phe His Gly Asp Pro Ala
                245                 250                 255

Tyr Thr Cys Pro Tyr Gln Asp Tyr Met Asp Gly Val Met Asn Tyr Pro
            260                 265                 270

Ile Tyr Tyr Pro Leu Leu Asn Ala Phe Lys Ser Ser Ser Gly Ser Met
        275                 280                 285

Ser Asp Leu Tyr Asn Met Ile Asn Thr Val Ala Ser Asn Cys Arg Asp
290                 295                 300
```

-continued

```
Pro Thr Leu Leu Gly Asn Phe Ile Glu Asn His Asp Asn Pro Arg Phe
305                 310                 315                 320

Pro Asn Tyr Thr Pro Asp Met Ser Arg Ala Lys Asn Val Leu Ala Phe
            325                 330                 335

Leu Phe Leu Thr Asp Gly Ile Pro Ile Val Tyr Ala Gly Gln Glu Gln
            340                 345                 350

His Tyr Ser Gly Ser Asn Asp Pro Tyr Asn Arg Glu Pro Val Trp Trp
            355                 360                 365

Ser Ser Tyr Ser Thr Ser Ser Glu Leu Tyr Lys Phe Ile Ala Thr Thr
370                 375                 380

Asn Lys Ile Arg Lys Leu Ala Ile Ser Lys Asp Ser Ser Tyr Leu Thr
385                 390                 395                 400

Ser Arg Asn Thr Pro Phe Tyr Ser Asp Ser Asn Tyr Ile Ala Met Arg
                405                 410                 415

Lys Gly Ser Gly Gly Ser Gln Val Leu Thr Leu Asn Asn Ile Gly
                420                 425                 430

Thr Ser Ile Gly Ser Tyr Thr Phe Asp Leu Tyr Asp His Gly Tyr Asn
                435                 440                 445

Ser Gly Ala Asn Leu Val Glu Leu Tyr Thr Cys Ser Ser Val Gln Val
450                 455                 460

Gly Ser Asn Gly Ala Ile Ser Ile Pro Met Thr Ser Gly Leu Pro Arg
465                 470                 475                 480

Val Leu Val Pro Ala Ala Trp Val Ser Gly Ser Leu Cys Gly Leu
                485                 490                 495

Thr Asn Pro Thr Ser Lys Thr Thr Ala Thr Thr Thr Ser Thr Thr
                500                 505                 510

Thr Cys Ala Ser Ala Thr Ala Thr Ala Ile Thr Val Val Phe Gln Glu
                515                 520                 525

Arg Val Gln Thr Ala Tyr Gly Glu Asn Val Phe Leu Ala Gly Ser Ile
530                 535                 540

Ser Gln Leu Gly Asn Trp Asp Thr Thr Glu Ala Val Ala Leu Ser Ala
545                 550                 555                 560

Ala Gln Tyr Thr Ala Thr Asp Pro Leu Trp Thr Val Ala Ile Glu Leu
                565                 570                 575

Pro Val Gly Thr Ser Phe Glu Phe Lys Phe Leu Lys Lys Arg Gln Asp
                580                 585                 590

Gly Ser Ile Val Trp Glu Ser Asn Pro Asn Arg Ser Ala Lys Val Asn
                595                 600                 605

Glu Gly Cys Ala Arg Thr Thr Gln Thr Ile Ser Thr Ser Trp Arg
610                 615                 620
```

<210> SEQ ID NO 6
<211> LENGTH: 478
<212> TYPE: PRT
<213> ORGANISM: Aspergillus niger
<220> FEATURE:
<221> NAME/KEY: misc_feature
<222> LOCATION: (1)..(478)
<223> OTHER INFORMATION: Alpha-Amylase from Aspergillus niger

<400> SEQUENCE: 6

```
Ala Thr Pro Ala Asp Trp Arg Ser Gln Ser Ile Tyr Phe Leu Leu Thr
1               5                   10                  15

Asp Arg Phe Ala Arg Thr Asp Gly Ser Thr Thr Ala Thr Cys Asn Thr
                20                  25                  30
```

```
Ala Asp Gln Lys Tyr Cys Gly Thr Trp Gln Gly Ile Ile Asp Lys
             35                  40                  45

Leu Asp Tyr Ile Gln Gly Met Gly Phe Thr Ala Ile Trp Ile Thr Pro
 50                  55                  60

Val Thr Ala Gln Leu Pro Gln Thr Thr Ala Tyr Gly Asp Ala Tyr His
 65                  70                  75                  80

Gly Tyr Trp Gln Gln Asp Ile Tyr Ser Leu Asn Glu Asn Tyr Gly Thr
                 85                  90                  95

Ala Asp Asp Leu Lys Ala Leu Ser Ser Ala Leu His Glu Arg Gly Met
                100                 105                 110

Tyr Leu Met Val Asp Val Val Ala Asn His Met Gly Tyr Asp Gly Ala
            115                 120                 125

Gly Ser Ser Val Asp Tyr Ser Val Phe Lys Pro Phe Ser Ser Gln Asp
130                 135                 140

Tyr Phe His Pro Phe Cys Phe Ile Gln Asn Tyr Glu Asp Gln Thr Gln
145                 150                 155                 160

Val Glu Asp Cys Trp Leu Gly Asp Asn Thr Val Ser Leu Pro Asp Leu
                165                 170                 175

Asp Thr Thr Lys Asp Val Val Lys Asn Glu Trp Tyr Asp Trp Val Gly
            180                 185                 190

Ser Leu Val Ser Asn Tyr Ser Ile Asp Gly Leu Arg Ile Asp Thr Val
        195                 200                 205

Lys His Val Gln Lys Asp Phe Trp Pro Gly Tyr Asn Lys Ala Ala Gly
210                 215                 220

Val Tyr Cys Ile Gly Glu Val Leu Asp Gly Asp Pro Ala Tyr Thr Cys
225                 230                 235                 240

Pro Tyr Gln Asn Val Met Asp Gly Val Leu Asn Tyr Pro Ile Tyr Tyr
                245                 250                 255

Pro Leu Leu Asn Ala Phe Lys Ser Thr Ser Gly Ser Met Asp Asp Leu
            260                 265                 270

Tyr Asn Met Ile Asn Thr Val Lys Ser Asp Cys Pro Asp Ser Thr Leu
        275                 280                 285

Leu Gly Thr Phe Val Glu Asn His Asp Asn Pro Arg Phe Ala Ser Tyr
290                 295                 300

Thr Asn Asp Ile Ala Leu Ala Lys Asn Val Ala Ala Phe Ile Ile Leu
305                 310                 315                 320

Asn Asp Gly Ile Pro Ile Ile Tyr Ala Gly Gln Glu Gln His Tyr Ala
                325                 330                 335

Gly Gly Asn Asp Pro Ala Asn Arg Glu Ala Thr Trp Leu Ser Gly Tyr
            340                 345                 350

Pro Thr Asp Ser Glu Leu Tyr Lys Leu Ile Ala Ser Ala Asn Ala Ile
        355                 360                 365

Arg Asn Tyr Ala Ile Ser Lys Asp Thr Gly Phe Val Thr Tyr Lys Asn
370                 375                 380

Trp Pro Ile Tyr Lys Asp Asp Thr Thr Ile Ala Met Arg Lys Gly Thr
385                 390                 395                 400

Asp Gly Ser Gln Ile Val Thr Ile Leu Ser Asn Lys Gly Ala Ser Gly
                405                 410                 415

Asp Ser Tyr Thr Leu Ser Leu Ser Gly Ala Gly Tyr Thr Ala Gly Gln
            420                 425                 430

Gln Leu Thr Glu Val Ile Gly Cys Thr Thr Val Thr Val Gly Ser Asp
        435                 440                 445
```

```
Gly Asn Val Pro Val Pro Met Ala Gly Gly Leu Pro Arg Val Leu Tyr
    450                 455                 460

Pro Thr Glu Lys Leu Ala Gly Ser Lys Ile Cys Ser Ser Ser
465                 470                 475
```

<210> SEQ ID NO 7
<211> LENGTH: 1911
<212> TYPE: DNA
<213> ORGANISM: Aspergillus clavatus
<220> FEATURE:
<221> NAME/KEY: misc_feature
<222> LOCATION: (1)..(1911)
<223> OTHER INFORMATION: cDNA encoding, Aspergillus clavatus NRRL 1
      alpha amylase, putative

<400> SEQUENCE: 7

```
atgaagcttc tagctttgac aactgccttc gccctgttgg gcaaaggggt atttggtcta    60
actccggccg aatggcgggg ccagtctatc tacttcctga taacggaccg gtttgctcgt   120
acagatggct caacaaccgc tccatgtgat ctcagccaga gggcgtactg tggtggaagc   180 tggcaggggta ttatcaagca actcgattat atccaaggaa tgggcttcac tgctatttgg   240
atcacaccca ttacggagca aatcccacag gataccgctg aaggatcagc attccacggc   300
tattggcaga aggatattta caatgtcaac tcccatttcg gaaccgccga tgacattcgg   360
gcattgtcca aggcccttca cgacagggga atgtacctga tgattgacgt tgttgccaac   420
cacatgggtt acaatggacc tggtgcctcg actgattta gcacctttac cccgttcaac   480
tctgcctcct acttccactc gtactgcccg atcaacaact ataacgacca gtctcaggta   540
gagaactgtt ggttgggaga caacactgtg gctctggcag acctatacac ccagcattcg   600
gatgtgcgga acatctggta cagctggatc aaagaaattg ttggcaatta ctctgctgat   660
ggtctgcgta tcgacaccgt caagcacgtt gaaaaggatt tctggactgg ctacacccaa   720
gctgctggtg tttataccgt tggcgaggta ttagatgggg accggcctta ccctgcccc   780 tatcagggat atgtggacgg tgtcctgaat tatcccatct attatcccct cctgagagcg   840
ttcgaatcgt cgagtggtag catgggtgat ctttacaata tgatcaactc tgtggcctcg   900
gattgtaaag accccaccgt gctaggaagt ttcattgaga accatgacaa tcctcgcttc   960
gctagctata ccaaggatat gtcccaggcc aaggctgtta ttagctatgt catactatcg  1020
gacggaatcc ccatcatcta ttctggacag gagcagcact actctggtgg aaatgacccg  1080
tacaaccgcg aagctatctg gttgtcgggt tactctacca cctcagagct gtataaattc  1140
attgccacca cgaacaagat ccgtcagctc gccatttcaa aggattcaag ctatcttact  1200
tcacgaaaca atcccttcta cactgatagc aacaccattg caatgcgaaa gggctccggg  1260
ggctcgcagg tcatcactgt actttccaac tctggttcca acggtggatc gtacacgctc  1320
aacttgggta cagcggata ctcgtctgga gccaatctag tggaggtgta cacctgctcg  1380
tctgtcacgg tcggttccga cggcaagatc cccgtcccca tggcatctgg tcttcccgt  1440 gtccttgttc cggcatcttg gatgtccgga agtggattgt gcggcagctc ttccaccact  1500
accctcgtca ccgccaccac gactccaact ggcagctctt ccagcactac cctcgccacc  1560
gccgtcacga ctccaactgg tagctgcaaa actgcgacga ccgttccagt ggtccttgaa  1620
gagagcgtga gcatccta cggcgagaac atcttcatct ccggctccat ccctcagctc  1680
ggtagctgga accgggataa agcagtcgct ctttcttcca gccagtacac ttcgtcgaat  1740
cctttgtggg ccgtcactct cgacctcccc gtgggaactt cgtttgaata caaattcctc  1800
```

```
aagaaggagc agaatggtgg cgtcgcttgg gagaatgacc ctaaccggtc ttacactgtt   1860
cccgaagcgt gtgccggtac ctcccaaaag gtggacagct cttggaggtg a            1911
```

<210> SEQ ID NO 8
<211> LENGTH: 38
<212> TYPE: DNA
<213> ORGANISM: Artificial Sequence
<220> FEATURE:
<223> OTHER INFORMATION: Synthetic primer

<400> SEQUENCE: 8

```
ggggcggccg ccaccatgaa gcttctagct ttgacaac                             38
```

<210> SEQ ID NO 9
<211> LENGTH: 35
<212> TYPE: DNA
<213> ORGANISM: Artificial Sequence
<220> FEATURE:
<223> OTHER INFORMATION: Synthetic primer

<400> SEQUENCE: 9

```
cccggcgcgc cttatcacct ccaagagctg tccac                               35
```

<210> SEQ ID NO 10
<211> LENGTH: 108
<212> TYPE: PRT
<213> ORGANISM: Aspergillus clavatus
<220> FEATURE:
<221> NAME/KEY: misc_feature
<222> LOCATION: (1)..(108)
<223> OTHER INFORMATION: AcAmy1 carbohydrate binding domain

<400> SEQUENCE: 10

```
Cys Lys Thr Ala Thr Thr Val Pro Val Val Leu Glu Glu Ser Val Arg
1               5                   10                  15

Thr Ser Tyr Gly Glu Asn Ile Phe Ile Ser Gly Ser Ile Pro Gln Leu
            20                  25                  30

Gly Ser Trp Asn Pro Asp Lys Ala Val Ala Leu Ser Ser Ser Gln Tyr
        35                  40                  45

Thr Ser Ser Asn Pro Leu Trp Ala Val Thr Leu Asp Leu Pro Val Gly
    50                  55                  60

Thr Ser Phe Glu Tyr Lys Phe Leu Lys Lys Glu Gln Asn Gly Gly Val
65                  70                  75                  80

Ala Trp Glu Asn Asp Pro Asn Arg Ser Tyr Thr Val Pro Glu Ala Cys
                85                  90                  95

Ala Gly Thr Ser Gln Lys Val Asp Ser Ser Trp Arg
            100                 105
```

<210> SEQ ID NO 11
<211> LENGTH: 31
<212> TYPE: PRT
<213> ORGANISM: Aspergillus clavatus
<220> FEATURE:
<221> NAME/KEY: misc_feature
<222> LOCATION: (1)..(31)
<223> OTHER INFORMATION: AcAmy1 linker (linker region)

<400> SEQUENCE: 11

```
Ser Thr Thr Thr Leu Val Thr Ala Thr Thr Pro Thr Gly Ser Ser
1               5                   10                  15

Ser Ser Thr Thr Leu Ala Thr Ala Val Thr Thr Pro Thr Gly Ser
            20                  25                  30
```

<210> SEQ ID NO 12
<211> LENGTH: 630
<212> TYPE: PRT
<213> ORGANISM: Aspergillus fumigatus
<220> FEATURE:
<221> NAME/KEY: misc_feature
<222> LOCATION: (1)..(630)
<223> OTHER INFORMATION: Alpha-amylase from Aspergillus fumigatus Af293

<400> SEQUENCE: 12

```
Met Lys Trp Ile Ala Gln Leu Phe Pro Leu Ser Leu Cys Ser Ser Leu
1               5                   10                  15

Leu Gly Gln Ala Ala His Ala Leu Thr Pro Ala Glu Trp Arg Ser Gln
            20                  25                  30

Ser Ile Tyr Phe Leu Leu Thr Asp Arg Phe Gly Arg Glu Asp Asn Ser
        35                  40                  45

Thr Thr Ala Ala Cys Asp Val Thr Gln Arg Leu Tyr Cys Gly Gly Ser
    50                  55                  60

Trp Gln Gly Ile Ile Asn His Leu Asp Tyr Ile Gln Gly Met Gly Phe
65                  70                  75                  80

Thr Ala Ile Trp Ile Thr Pro Val Thr Glu Gln Phe Tyr Glu Asn Thr
                85                  90                  95

Gly Asp Gly Thr Ser Tyr His Gly Tyr Trp Gln Gln Asn Ile His Glu
            100                 105                 110

Val Asn Ala Asn Tyr Gly Thr Ala Gln Asp Leu Arg Asp Leu Ala Asn
        115                 120                 125

Ala Leu His Ala Arg Gly Met Tyr Leu Met Val Asp Val Val Ala Asn
    130                 135                 140

His Met Gly Tyr Asn Gly Ala Gly Asn Ser Val Asn Tyr Gly Val Phe
145                 150                 155                 160

Thr Pro Phe Asp Ser Ala Thr Tyr Phe His Pro Tyr Cys Leu Ile Thr
                165                 170                 175

Asp Tyr Asn Asn Gln Thr Ala Val Glu Asp Cys Trp Leu Gly Asp Thr
            180                 185                 190

Thr Val Ser Leu Pro Asp Leu Asp Thr Thr Ser Thr Ala Val Arg Ser
        195                 200                 205

Ile Trp Tyr Asp Trp Val Lys Gly Leu Val Ala Asn Tyr Ser Ile Asp
    210                 215                 220

Gly Leu Arg Ile Asp Thr Val Lys His Val Glu Lys Asp Phe Trp Pro
225                 230                 235                 240

Gly Tyr Asn Asp Ala Ala Gly Val Tyr Cys Val Gly Glu Val Phe Ser
                245                 250                 255

Gly Asp Pro Gln Tyr Thr Cys Pro Tyr Gln Asn Tyr Leu Asp Gly Val
            260                 265                 270

Leu Asn Tyr Pro Ile Tyr Tyr Gln Leu Leu Tyr Ala Phe Gln Ser Thr
        275                 280                 285

Ser Gly Ser Ile Ser Asn Leu Tyr Asn Met Ile Ser Ser Val Ala Ser
    290                 295                 300

Asp Cys Ala Asp Pro Thr Leu Leu Gly Asn Phe Ile Glu Asn His Asp
305                 310                 315                 320

Asn Pro Arg Phe Ala Ser Tyr Thr Ser Asp Tyr Ser Gln Ala Lys Asn
                325                 330                 335

Val Ile Ser Phe Met Phe Phe Ser Asp Gly Ile Pro Ile Val Tyr Ala
            340                 345                 350

Gly Gln Glu Gln His Tyr Ser Gly Gly Ala Asp Pro Ala Asn Arg Glu
        355                 360                 365
```

```
Ala Val Trp Leu Ser Gly Tyr Ser Thr Ser Ala Thr Leu Tyr Ser Trp
    370                 375                 380

Ile Ala Ser Thr Asn Lys Ile Arg Lys Leu Ala Ile Ser Lys Asp Ser
385                 390                 395                 400

Ala Tyr Ile Thr Ser Lys Asn Asn Pro Phe Tyr Tyr Asp Ser Asn Thr
                405                 410                 415

Leu Ala Met Arg Lys Gly Ser Val Ala Gly Ser Gln Val Ile Thr Val
            420                 425                 430

Leu Ser Asn Lys Gly Ser Ser Gly Ser Ser Tyr Thr Leu Ser Leu Ser
        435                 440                 445

Gly Thr Gly Tyr Ser Ala Gly Ala Thr Leu Val Glu Met Tyr Thr Cys
    450                 455                 460

Thr Thr Leu Thr Val Asp Ser Ser Gly Asn Leu Ala Val Pro Met Val
465                 470                 475                 480

Ser Gly Leu Pro Arg Val Phe Val Pro Ser Ser Trp Val Ser Gly Ser
                485                 490                 495

Gly Leu Cys Gly Asp Ser Ile Ser Thr Thr Ala Thr Ala Pro Ser Ala
            500                 505                 510

Thr Thr Ser Ala Thr Ala Thr Arg Thr Ala Cys Ala Ala Ala Thr Ala
        515                 520                 525

Ile Pro Ile Leu Phe Glu Glu Leu Val Thr Thr Thr Tyr Gly Glu Ser
    530                 535                 540

Ile Tyr Leu Thr Gly Ser Ile Ser Gln Leu Gly Asn Trp Asp Thr Ser
545                 550                 555                 560

Ser Ala Ile Ala Leu Ser Ala Ser Lys Tyr Thr Ser Ser Asn Pro Glu
                565                 570                 575

Trp Tyr Val Thr Val Thr Leu Pro Val Gly Thr Ser Phe Glu Tyr Lys
            580                 585                 590

Phe Val Lys Lys Gly Ser Asp Gly Ser Ile Ala Trp Glu Ser Asp Pro
        595                 600                 605

Asn Arg Ser Tyr Thr Val Pro Thr Gly Cys Ala Gly Thr Thr Val Thr
    610                 615                 620

Val Ser Asp Thr Trp Arg
625                 630

<210> SEQ ID NO 13
<211> LENGTH: 607
<212> TYPE: PRT
<213> ORGANISM: Aspergillus terreus
<220> FEATURE:
<221> NAME/KEY: misc_feature
<222> LOCATION: (1)..(607)
<223> OTHER INFORMATION: Alpha-amylase precursor from Aspergillus
      terreus NIH2624

<400> SEQUENCE: 13

Met Lys Trp Thr Ser Ser Leu Leu Leu Leu Ser Val Ile Gly Gln
1               5                   10                  15

Ala Thr His Ala Leu Thr Pro Ala Glu Trp Arg Ser Gln Ser Ile Tyr
            20                  25                  30

Phe Leu Leu Thr Asp Arg Phe Gly Arg Thr Asp Asn Ser Thr Thr Ala
        35                  40                  45

Ala Cys Asp Thr Ser Asp Arg Val Tyr Cys Gly Gly Ser Trp Gln Gly
    50                  55                  60

Ile Ile Asn Gln Leu Asp Tyr Ile Gln Gly Met Gly Phe Thr Ala Ile
65                  70                  75                  80
```

```
Trp Ile Thr Pro Val Thr Gly Gln Phe Tyr Glu Asn Thr Gly Asp Gly
                85                  90                  95
Thr Ser Tyr His Gly Tyr Trp Gln Asp Ile Tyr Asp Leu Asn Tyr
            100                 105                 110
Asn Tyr Gly Thr Ala Gln Asp Leu Lys Asn Leu Ala Asn Ala Leu His
            115                 120                 125
Glu Arg Gly Met Tyr Leu Met Val Asp Val Val Ala Asn His Met Gly
130                 135                 140
Tyr Asp Gly Ala Gly Asn Thr Val Asp Tyr Ser Val Phe Asn Pro Phe
145                 150                 155                 160
Ser Ser Ser Ser Tyr Phe His Pro Tyr Cys Leu Ile Ser Asn Tyr Asp
                165                 170                 175
Asn Gln Thr Asn Val Glu Asp Cys Trp Leu Gly Asp Thr Thr Val Ser
            180                 185                 190
Leu Pro Asp Leu Asp Thr Thr Ser Thr Ala Val Arg Asn Ile Trp Tyr
            195                 200                 205
Asp Trp Val Ala Asp Leu Val Ala Asn Tyr Ser Ile Asp Gly Leu Arg
210                 215                 220
Val Asp Thr Val Lys His Val Glu Lys Asp Phe Trp Pro Gly Tyr Asn
225                 230                 235                 240
Ser Ala Ala Gly Val Tyr Cys Val Gly Glu Val Tyr Ser Gly Asp Pro
                245                 250                 255
Ala Tyr Thr Cys Pro Tyr Gln Asn Tyr Met Asp Gly Val Leu Asn Tyr
            260                 265                 270
Pro Ile Tyr Tyr Gln Leu Leu Tyr Ala Phe Glu Ser Ser Ser Gly Ser
            275                 280                 285
Ile Ser Asp Leu Tyr Asn Met Ile Ser Ser Val Ala Ser Ser Cys Lys
            290                 295                 300
Asp Pro Thr Leu Leu Gly Asn Phe Ile Glu Asn His Asp Asn Pro Arg
305                 310                 315                 320
Phe Ala Ser Tyr Thr Ser Asp Tyr Ser Gln Ala Lys Asn Val Ile Thr
                325                 330                 335
Phe Ile Phe Leu Ser Asp Gly Ile Pro Ile Val Tyr Ala Gly Gln Glu
            340                 345                 350
Gln His Tyr Ser Gly Gly Ser Asp Pro Ala Asn Arg Glu Ala Thr Trp
            355                 360                 365
Leu Ser Gly Tyr Ser Thr Ser Ala Thr Leu Tyr Thr Trp Ile Ala Thr
            370                 375                 380
Thr Asn Gln Ile Arg Ser Leu Ala Ile Ser Lys Asp Ala Gly Tyr Val
385                 390                 395                 400
Gln Ala Lys Asn Asn Pro Phe Tyr Ser Asp Ser Asn Thr Ile Ala Met
                405                 410                 415
Arg Lys Gly Thr Thr Ala Gly Ala Gln Val Ile Thr Val Leu Ser Asn
            420                 425                 430
Lys Gly Ala Ser Gly Ser Ser Tyr Thr Leu Ser Leu Ser Gly Thr Gly
            435                 440                 445
Tyr Ser Ala Gly Ala Thr Leu Val Glu Thr Tyr Thr Cys Thr Thr Val
            450                 455                 460
Thr Val Asp Ser Ser Gly Asn Leu Pro Val Pro Met Thr Ser Gly Leu
465                 470                 475                 480
Pro Arg Val Phe Val Pro Ser Ser Trp Val Asn Gly Ser Ala Leu Cys
                485                 490                 495
```

```
Asn Thr Glu Cys Thr Ala Ala Thr Ser Ile Ser Val Leu Phe Glu Glu
            500             505             510

Leu Val Thr Thr Thr Tyr Gly Glu Asn Ile Tyr Leu Ser Gly Ser Ile
        515             520             525

Ser Gln Leu Gly Ser Trp Asn Thr Ala Ser Ala Val Ala Leu Ser Ala
    530             535             540

Ser Gln Tyr Thr Ser Ser Asn Pro Glu Trp Tyr Val Ser Val Thr Leu
545             550             555                         560

Pro Val Gly Thr Ser Phe Gln Tyr Lys Phe Ile Lys Lys Gly Ser Asp
            565             570             575

Gly Ser Val Val Trp Glu Ser Asp Pro Asn Arg Ser Tyr Thr Val Pro
        580             585             590

Ala Gly Cys Glu Gly Ala Thr Val Thr Val Ala Asp Thr Trp Arg
        595             600             605
```

US 9,365,871 B2

METHOD OF USING α-AMYLASE FROM *ASPERGILLUS CLAVATUS* FOR SACCHARIFICATION

CROSS REFERENCE TO RELATED APPLICATIONS

This application is a Divisional of U.S. patent application Ser. No. 13/888,303, filed May 6, 2013, (now U.S. Pat. No. 8,945,889) which claims priority to the filing date of PCT Patent Application Serial No. PCT/CN2012/075352, filed May 11, 2012; the disclosure of which applications are herein incorporated by reference in their entirety.

SEQUENCE LISTING

The sequence listing submitted via EFS, in compliance with 37 C.F.R. §1.52(e), is incorporated herein by reference. The sequence listing text file submitted via EFS contains the file "40077US SeqList.txt" created on Aug. 12, 2013, which is 40,502 bytes in size.

FIELD OF THE INVENTION

Methods of using an α-amylase from *Aspergillus clavatus* (AcAmy1) or a variant thereof include saccharification of starch, for example, simultaneous saccharification and fermentation (SSF).

BACKGROUND

Starch consists of a mixture of amylose (15-30% w/w) and amylopectin (70-85% w/w). Amylose consists of linear chains of α-1,4-linked glucose units having a molecular weight (MW) from about 60,000 to about 800,000. Amylopectin is a branched polymer containing α-1,6 branch points every 24-30 glucose units; its MW may be as high as 100 million.

Sugars from starch, in the form of concentrated dextrose syrups, are currently produced by an enzyme catalyzed process involving: (1) liquefaction (or viscosity reduction) of solid starch with an α-amylase into dextrins having an average degree of polymerization of about 7-10, and (2) saccharification of the resulting liquefied starch (i.e. starch hydrolysate) with amyloglucosidase (also called glucoamylase or GA). The resulting syrup has a high glucose content. Much of the glucose syrup that is commercially produced is subsequently enzymatically isomerized to a dextrose/fructose mixture known as isosyrup. The resulting syrup also may be fermented with microorganisms, such as yeast, to produce commercial products including ethanol, citric acid, lactic acid, succinic acid, itaconic acid, monosodium glutamate, gluconates, lysine, other organic acids, other amino acids, and other biochemicals, for example. Fermentation and saccharification can be conducted simultaneously (i.e., an SSF process) to achieve greater economy and efficiency.

α-Amylases hydrolyze starch, glycogen, and related polysaccharides by cleaving internal α-1,4-glucosidic bonds at random. α-Amylases, particularly from Bacilli, have been used for a variety of different purposes, including starch liquefaction and saccharification, textile desizing, starch modification in the paper and pulp industry, brewing, baking, production of syrups for the food industry, production of feedstocks for fermentation processes, and in animal feed to increase digestability. These enzymes can also be used to remove starchy soils and stains during dishwashing and laundry washing.

Several *Aspergillus* species, including *A. clavatus*, show strong amylolytic behavior, which is retained under acidic conditions. See Nahira et al. (1956) "Taxonomic studies on the genus *Aspergillus*. VIII. The relation between the morphological characteristics and the amylolytic properties in the *Aspergillus*," *Hakko Kogaku Zasshi* 34: 391-99, 423-28, 457-63. *A. clavatus*, for example, secretes an amylase activity among other polysaccharide-degrading enzymes, which allows this fungus to digest complex carbohydrates in its environment. See Ogundero et al. (1987) "Polysaccharide degrading enzymes of a toxigenic strain of *Aspergillus clavatus* from Nigerian poultry feeds," *Die Nahrung* 10: 993-1000. When the effect of pH on the ability of *A. clavatus* to degrade milled feedstuff was determined, *A. clavatus* was shown to degrade feeds over all the tested pH values from 3.2 to 7.8. See Ogundero (1987) "Toxigenic fungi and the deterioration of Nigerian poultry feeds," *Mycopathologia* 100: 75-83. Later studies showed peak *A. clavatus* amylase activity at pH 7-8, when the *A. clavatus* were grown on maize yeast extract medium or wheat yeast extract medium. Adisa (1994) "Mycoflora of post-harvest maize and wheat grains and the implications of their contamination by molds," *Die Nahrung* 38(3): 318-26.

SUMMARY

An α-amylase from *Aspergillus clavatus* (AcAmy1) catalyzes saccharification for extended periods at moderate temperatures and an acidic pH. An example of a known α-amylase from *Aspergillus clavatus* NRRL1 (SEQ ID NO: 1), a variant of the α-amylase, encoding nucleic acids, and host cells that express the polynucleotides are provided. AcAmy1 has an acidic working range and contributes to high ethanol yield and low residual starch in simultaneous saccharification and fermentation (SSF), for example, particularly when used together with a glucoamylase. Despite the Adisa 1994 disclosure that the peak *A. clavatus* amylase activity occurs at pH 7-8 at 25-30° C., AcAmy1 has a pH optimum at pH 4.5 at 50° C. AcAmy1 exhibits high activity at elevated temperatures and at low pH, so AcAmy1 can be used efficiently in a process of saccharification in the presence of fungal glucoamylases, such as *Aspergillus niger* glucoamylase (AnGA). AcAmy1 advantageously catalyzes starch saccharification to an oligosaccharide composition significantly enriched in DP1 and DP2 (i.e., glucose and maltose) compared to the products of saccharification catalyzed by *Aspergillus kawachii* alpha-amylase (AkAA). AcAmy1 can be used at a lower dosage than AkAA to produce comparable levels of ethanol. AcAmy1 can be used in combination with enzymes derived from plants (e.g., cereals and grains). AcAmy1 also can be used in combination with enzymes secreted by, or endogenous to, a host cell. For example, AcAmy1 can be added to a fermentation or SSF process during which one or more amylases, glucoamylases, proteases, lipases, phytases, esterases, redox enzymes, transferases, or other enzymes are secreted by the production host. AcAmy1 may also work in combination with endogenous non-secreted production host enzymes. In another example, AcAmy1 can be secreted by a production host cell with other enzymes during fermentation or SSF. The AcAmy1 amylase may also be effective in direct hydrolysis of starch for syrup and/or biochemicals (e.g., alcohols, organic acids, amino acids, other biochemicals and biomaterials) where the reaction temperature is below the gelatinization temperature of substrate. AcAmy1 can be secreted by a host cell with other enzymes during fermentation or SSF.

Accordingly, provided is a method of saccharifying a solution may comprise starch to produce a composition comprising glucose, where the method may comprise (i) contacting the solution comprising starch with an isolated AcAmy1 or variant thereof having α-amylase activity and comprising an amino acid sequence with at least 80% amino acid sequence identity to (a) residues 20-636 of SEQ ID NO:1 or (b) residues 20-497 of SEQ ID NO:1; and (ii) saccharifying the solution comprising starch to produce the composition comprising glucose; where the isolated AcAmy1 or variant thereof catalyzes the saccharification of the starch solution to glucose.

The AcAmy1 or variant thereof may be dosed at about 17%-50%, or optionally about 17%-34% the dose of AkAA, to reduce the same quantity of residual starch under the same conditions. The AcAmy1 or variant thereof may also be dosed at about 17%-50%, or optionally about 17%-34% the dose of AkAA, to reduce the same quantity of DP3+ under the same conditions.

The composition comprising glucose may be enriched in DP1, DP2, or (DP1+DP2), when measured as a weight percentage of total DP1-DP7, compared to a second composition comprising glucose produced by AkAA under the same conditions. DP1 may be enriched about 1.5-fold at about 2 hours. In addition, DP2 may be enriched two- to three-fold at about 2 hours. Moreover, (DP1+DP2) may be enriched about 2.2-fold at about 2 hours.

The AcAmy1 or variant thereof may comprise an amino acid sequence with at least 90%, 95%, or 99% amino acid sequence identity to (a) residues 20-636 of SEQ ID NO:1 or (b) residues 20-497 of SEQ ID NO:1. The AcAmy1 or variant thereof may also comprise (a) residues 20-636 of SEQ ID NO:1 or (b) residues 20-497 of SEQ ID NO:1. The AcAmy1 or variant thereof may consist of an amino acid sequence with at least 80%, 90%, 95%, or 99% amino acid sequence identity to (a) residues 20-636 of SEQ ID NO:1 or (b) residues 20-497 of SEQ ID NO:1. The AcAmy1 or variant thereof may also consist of (a) residues 20-636 of SEQ ID NO:1 or (b) residues 20-497 of SEQ ID NO:1.

The starch solution may comprise liquefied starch, gelatinized starch, or granular starch. Saccharification may be conducted at a temperature range of about 30° C. to about 75° C. The temperature range may further be 47° C.-74° C. Saccharification may be conducted over a pH range of pH 2.0-pH 7.5. The pH range may further be pH 3.5-pH 5.5. The pH range may further be pH 3.5-pH 4.5.

The method may further comprise fermenting the glucose composition to produce an End of Fermentation (EOF) product. The fermentation may be a simultaneous saccharification and fermentation (SSF) reaction. The fermentation may be conducted for 48-70 hours at pH 2-8 and in a temperature range of 25° C.-70° C. The EOF product may comprise 8%-18% (v/v) ethanol. The EOF product may comprise a metabolite. The metabolite may be a citric acid, lactic acid, succinic acid, monosodium glutamate, gluconic acid, sodium gluconate, calcium gluconate, potassium gluconate, glucono delta-lactone, sodium erythorbate, omega 3 fatty acid, butanol, an amino acid, lysine, itaconic acid, 1,3-propanediol, or isoprene.

Use of AcAmy1 or variant thereof in the production of a fermented beverage is also provided, as well as a method of making a fermented beverage which may comprise: contacting a mash and/or a wort with AcAmy1 or variant thereof. A method of making a fermented beverage which may comprise: (a) preparing a mash; (b) filtering the mash to obtain a wort; and (c) fermenting the wort to obtain a fermented beverage, where AcAmy1 or variant thereof are added to: (i) the mash of step (a) and/or (ii) the wort of step (b) and/or (iii) the wort of step (c). A fermented beverage produced by the disclosed methods is also provided.

The fermented beverage or end of fermentation product can be selected from the group consisting of a beer selected such as full malted beer, beer brewed under the "Reinheitsgebot", ale, IPA, lager, bitter, Happoshu (second beer), third beer, dry beer, near beer, light beer, low alcohol beer, low calorie beer, porter, bock beer, stout, malt liquor, non-alcoholic beer, and non-alcoholic malt liquor; or cereal or malt beverages such as fruit flavoured malt beverages, liquor flavoured malt beverages, and coffee flavoured malt beverages.

The method may further comprise adding glucoamylase, hexokinase, xylanase, glucose isomerase, xylose isomerase, phosphatase, phytase, pullulanase, β-amylase, α-amylase that is not AcAmy1, protease, cellulase, hemicellulase, lipase, cutinase, isoamylase, redox enzyme, esterase, transferase, pectinase, alpha-glucosidase, beta-glucosidase, or a combination thereof, to the starch solution. Glucoamylase may be added to 0.1-2 glucoamylase units (GAU)/g ds.

The isolated AcAmy1 or a variant thereof may be expressed and secreted by a host cell. The starch solution may be contacted with the host cell. The host cell may further express and secrete a glucoamylase. The host cell may further be capable of fermenting the glucose composition.

Accordingly, provided is a composition for the use of saccharifying a solution comprising starch, may comprise an isolated AcAmy1 or variant thereof having α-amylase activity and comprising an amino acid sequence with at least 80%, 90%, 95%, 99% or 100% amino acid sequence identity to (a) residues 20-636 of SEQ ID NO:1 or (b) residues 20-497 of SEQ ID NO:1. The AcAmy1 or variant thereof may consist of an amino acid sequence with at least 80%, 90%, 95%, 99%, or 100% amino acid sequence identity to (a) residues 20-636 of SEQ ID NO:1 or (b) residues 20-497 of SEQ ID NO:1.

The composition may be a cultured cell material. The composition may further comprise a glucoamylase. The AcAmy1 or variant thereof may also be purified.

The AcAmy1 or variant thereof may be expressed and secreted by a host cell. The host cell may be a filamentous fungal cell. The host cell may be an *Aspergillus* sp. or *Trichoderma reesei* cell.

Accordingly, provided is a method of baking comprising adding a baking composition to a substance to be baked, and baking the substance to produce a baked good, where the baking composition comprises an isolated AcAmy1 or variant thereof having α-amylase activity and comprising an amino acid sequence with at least 80%, 90%, 95%, 99% or 100% amino acid sequence identity to (a) residues 20-636 of SEQ ID NO:1 or (b) residues 20-497 of SEQ ID NO:1, where the isolated AcAmy1 or variant thereof catalyzes the hydrolysis of starch components present in the substance to produce smaller starch-derived molecules. The AcAmy1 or variant thereof may consist of an amino acid sequence with at least 80%, 90%, 95%, 99%, or 100% amino acid sequence identity to (a) residues 20-636 of SEQ ID NO:1 or (b) residues 20-497 of SEQ ID NO:1. The baking composition may further comprise flour, an anti-staling amylase, a phospholipase, and/or a phospholipid.

Accordingly, also provided is a method of producing a food composition, comprising combining (i) one or more food ingredients, and (ii) an isolated AcAmy1 or variant thereof having α-amylase activity and comprising an amino acid sequence with at least 80%, 90%, 95%, 99% or 100% amino acid sequence identity to (a) residues 20-636 of SEQ ID NO:1 or (b) residues 20-497 of SEQ ID NO:1, wherein said isolated AcAmy1 or variant thereof catalyzes the hydrolysis of starch components present in the food ingredients to produce glucose. The AcAmy1 or variant thereof may consist of an amino acid sequence with at least 80%, 90%, 95%, 99%, or 100% amino acid sequence identity to (a) residues 20-636 of SEQ ID NO:1 or (b) residues 20-497 of SEQ ID NO:1. The method may further comprise baking the food composition to produce a baked good. The method may further comprise (i) providing a starch medium; (ii) adding to the starch medium the AcAmy1 or variant thereof; and (iii) applying heat to the starch medium during or after step (b) to produce a bakery product.

The food composition may be enriched in DP1, DP2, or (DP1+DP2), when measured as a weight percentage of total DP1-DP7, compared to a second baked good produced by AkAA under the same conditions. The food composition may be selected from the group consisting of a food product, a baking composition, a food additive, an animal food product, a feed product, a feed additive, an oil, a meat, and a lard. The food composition may comprise a dough or a dough product, preferably a processed dough product.

The one or more food ingredients may comprise a baking ingredient or an additive. The one or more food ingredients may also be selected from the group consisting of flour; an anti-staling amylase; a phospholipase; a phospholipid; a maltogenic alpha-amylase or a variant, homologue, or mutants thereof which has maltogenic alpha-amylase activity; a bakery xylanase (EC 3.2.1.8); and a lipase. The one or more food ingredients may further be selected from the group consisting of (i) a maltogenic alpha-amylase from *Bacillus stearothermophilus*, (ii) a bakery xylanase is from *Bacillus, Aspergillus, Thermomyces* or *Trichoderma*, (iii) a glycolipase from *Fusarium heterosporum*.

Accordingly, also provided is a composition for use producing a food composition, comprising an isolated AcAmy1 or variant thereof having α-amylase activity and comprising an amino acid sequence with at least 80% amino acid sequence identity to (a) residues 20-636 of SEQ ID NO:1 or (b) residues 20-497 of SEQ ID NO:1 and one or more food ingredients. Also provided is a use of the AcAmy1 or variant thereof of any one of claims 69-73 in preparing a food composition. The food composition may comprise a dough or a dough product, including a processed dough product. The food composition may be a bakery composition. The AcAmy1 or variant thereof may be used in a dough product to retard or reduce staling, preferably detrimental retrogradation, of the dough product.

Accordingly, provided is a method of removing starchy stains from laundry, dishes, or textiles, which may comprise incubating a surface of the laundry, dishes, or textiles in the presence of an aqueous composition comprising an effective amount of an isolated AcAmy1 or variant thereof having α-amylase activity and comprising an amino acid sequence with at least 80%, 90%, 95%, 99% or 100% amino acid sequence identity to (a) residues 20-636 of SEQ ID NO:1 or (b) residues 20-497 of SEQ ID NO:1, and allowing the AcAmy1 or variant thereof to hydrolyze starch components present in the starchy stain to produce smaller starch-derived molecules that dissolve in the aqueous composition, and rinsing the surface, thereby removing the starchy stain from the surface. The AcAmy1 or variant thereof may consist of an amino acid sequence with at least 80%, 90%, 95%, 99%, or 100% amino acid sequence identity to (a) residues 20-636 of SEQ ID NO:1 or (b) residues 20-497 of SEQ ID NO:1.

Accordingly, provided is a composition for use in removing starchy stains from laundry, dishes, or textiles, which may comprise an isolated AcAmy1 or variant thereof having α-amylase activity and comprising an amino acid sequence with at least 80%, 90%, 95%, 99% or 100% amino acid sequence identity to (a) residues 20-636 of SEQ ID NO:1 or (b) residues 20-497 of SEQ ID NO:1 and a surfactant. The AcAmy1 or variant thereof may consist of an amino acid sequence with at least 80%, 90%, 95%, 99%, or 100% amino acid sequence identity to (a) residues 20-636 of SEQ ID NO:1 or (b) residues 20-497 of SEQ ID NO:1. The composition may be a laundry detergent, a laundry detergent additive, or a manual or automatic dishwashing detergent.

Accordingly, a method of desizing a textile is also provided, that may comprise contacting a desizing composition with a textile for a time sufficient to desize the textile, where the desizing composition may comprise an isolated AcAmy1 or variant thereof having α-amylase activity and comprising an amino acid sequence with at least 80%, 90%, 95%, 99% or 100% amino acid sequence identity to (a) residues 20-636 of SEQ ID NO:1 or (b) residues 20-497 of SEQ ID NO:1 and allowing the AcAmy1 or variant thereof to desize starch components present in the starchy stain to produce smaller starch-derived molecules that dissolve in the aqueous composition, and rinsing the surface, thereby removing the starchy stain from the surface. The AcAmy1 or variant thereof may consist of an amino acid sequence with at least 80%, 90%, 95%, 99%, or 100% amino acid sequence identity to (a) residues 20-636 of SEQ ID NO:1 or (b) residues 20-497 of SEQ ID NO:1.

Accordingly, use of AcAmy1 or variant thereof in the production of a glucose composition is also provided. A glucose composition produced by the disclosed methods is also provided. Use of AcAmy1 or variant thereof in the production of a liquefied starch is further provided. And a liquefied starch prepared by the disclosed methods is also disclosed.

Moreover, use of a desizing composition which may comprise AcAmy1 or variant thereof in desizing textiles is disclosed, as well as use of a baking composition which may comprise AcAmy1 or variant thereof in the production of a baked good.

BRIEF DESCRIPTION OF THE DRAWINGS

The accompanying drawings are incorporated in and constitute a part of this specification and illustrate various methods and compositions disclosed herein. In the drawings:

FIG. 1A and FIG. 1B depict a ClustalW alignment of the AcAmy1 catalytic core, linker region, and carbohydrate binding domain (residues 20-497, 498-528, and 529-636 of SEQ ID NO: 1, respectively), or the full length, with the corresponding residues of the α-amylases from: *T. stipitatus* ATCC 10500 (residues 20-497 and 520-627 of SEQ ID NO: 4, respectively); *A. nidulans* FGSC A4 (residues 20-497 and 516-623 of SEQ ID NO: 5, respectively); *A. fumigatus* Af293 (residues 24-502 and 523-630 of SEQ ID NO: 12, respectively); and *A. terreus* NIH2624 (residues 21-497 and 500-607 of SEQ ID NO: 13, respectively). Residues designated by an asterisk in FIG. 1 are AcAmy1 residues corresponding to conserved residues in SEQ ID NOS: 4-5 and 12-13.

DETAILED DESCRIPTION

Figure 2:
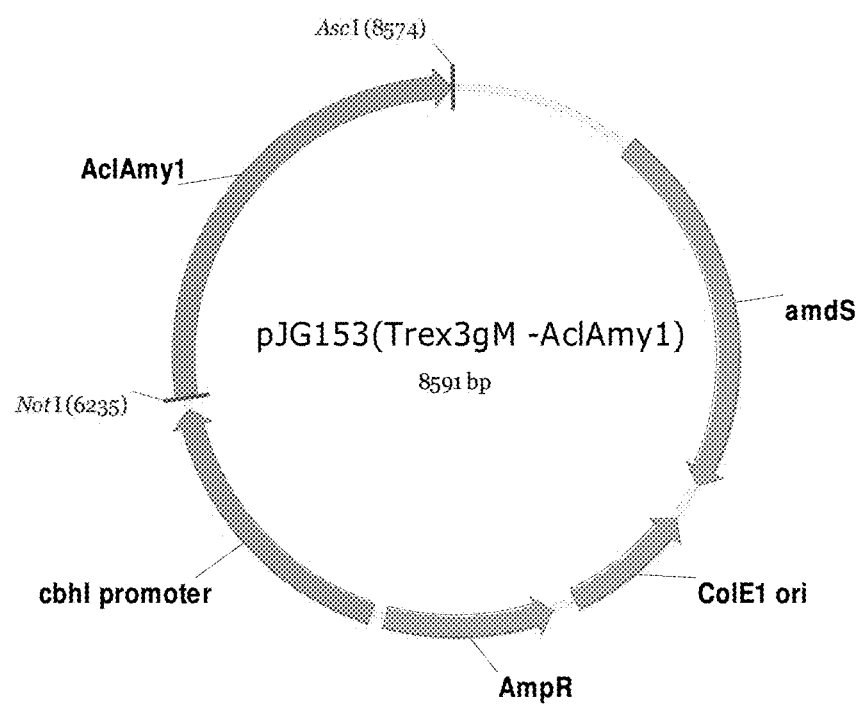
FIG. 2 depicts a map of a pJG153 expression vector comprising a polynucleotide that encodes an AcAmy1 polypeptide, pJG153(Tex3gM-AcAmy1).

A fungal α-amylase from *Aspergillus clavatus* (AcAmy1) is provided. AcAmy1 has a pH optimum of pH 4.5 and at least 70% activity over a range of pH 3 to pH 7. The enzyme has an optimum temperature of 66° C. and at least 70% activity over a temperature range of 47°-74° C., when tested at pH 4.5. These properties allow the enzyme to be used in combination with a glucoamylase under the same reaction conditions. This obviates the necessity of running a saccharification reaction as a batch process, where the pH and temperature must be adjusted for optimal use of the α-amylase or glucoamylase.

AcAmy1 also catalyzes the saccharification of a composition comprising starch to glucose. For example, after two hours of saccharification at 50° C., pH 5.3, using a DP7, amylopectin, or maltodextrin substrate, an oligosaccharide composition is produced. The composition is enriched in DP1, DP2, and (DP1+DP2), when measured as a weight percentage of total DP1-DP7, compared to the products of AkAA-catalyzed saccharification under the same conditions. For example, DP2 is enriched two- to three-fold at about 2 hours, DP1 is enriched about 1.5-fold at about 2 hours, and (DP1+DP2) is enriched about 2.2-fold at about 2 hours. This facilitates the utilization of the oligosaccharide composition by a fermenting organism in a SSF process, for example. In this role, AcAmy1 can produce the same ethanol yield as AkAA with a lower enzyme dosage, while reducing insoluble residual starch and minimizing any negative effects of insoluble residual starch on final product quality.

Exemplary applications for AcAmy1 and variants thereof amylases are in a process of starch saccharification, e.g., SSF, the preparation of cleaning compositions, such as detergent compositions for cleaning laundry, dishes, and other surfaces, for textile processing (e.g., desizing).

1. Definitions & Abbreviations

In accordance with this detailed description, the following abbreviations and definitions apply. Note that the singular forms "a," "an," and "the" include plural referents unless the context clearly dictates otherwise. Thus, for example, reference to "an enzyme" includes a plurality of such enzymes, and reference to "the dosage" includes reference to one or more dosages and equivalents thereof known to those skilled in the art, and so forth.

Unless defined otherwise, all technical and scientific terms used herein have the same meaning as commonly understood by one of ordinary skill in the art. The following terms are provided below.

1.1. Abbreviations and Acronyms

The following abbreviations/acronyms have the following meanings unless otherwise specified:

ABTS 2,2-azino-bis-3-ethylbenzothiazoline-6-sulfonic acid
AcAmy1 *Aspergillus clavatus* α-amylase
AE alcohol ethoxylate
AEO alcohol ethoxylate
AEOS alcohol ethoxysulfate
AES alcohol ethoxysulfate
AkAA *Aspergillus kawachii* α-amylase
AnGA *Aspergillus niger* glucoamylase
AOS α-olefinsulfonate
AS alkyl sulfate
cDNA complementary DNA
CMC carboxymethylcellulose
DE dextrose equivalent
DNA deoxyribonucleic acid
DPn degree of saccharide polymerization having n subunits
ds or DS dry solids
DTMPA diethylenetriaminepentaacetic acid
EC Enzyme Commission
EDTA ethylenediaminetetraacetic acid
EO ethylene oxide (polymer fragment)
EOF End of Fermentation
FGSC Fungal Genetics Stock Center
GA glucoamylase
GAU/g ds glucoamylase activity unit/gram dry solids
HFCS high fructose corn syrup
HgGA *Humicola grisea* glucoamylase
IPTG isopropyl β-D-thiogalactoside
IRS insoluble residual starch
kDa kiloDalton
LAS linear alkylbenzenesulfonate
MW molecular weight
MWU modified Wohlgemuth unit; $1.6 \times 10^{-5}$ mg/MWU=unit of activity
NCBI National Center for Biotechnology Information
NOBS nonanoyloxybenzenesulfonate
NTA nitriloacetic acid
OxAm Purastar HPAM 5000L (Danisco US Inc.)
PAHBAH p-hydroxybenzoic acid hydrazide
PEG polyethyleneglycol
pI isoelectric point
ppm parts per million, e.g., μg protein per gram dry solid
PVA poly(vinyl alcohol)
PVP poly(vinylpyrrolidone)
RNA ribonucleic acid
SAS alkanesulfonate
SDS-PAGE sodium dodecyl sulfate polyacrylamide gel electrophoresis
SSF simultaneous saccharification and fermentation
SSU/g solid soluble starch unit/gram dry solids
sp. species
TAED tetraacetylethylenediamine
TrGA *Trichoderma reesei* glucoamylase
w/v weight/volume
w/w weight/weight
v/v volume/volume
wt % weight percent
° C. degrees Centigrade
$H_2O$ water
$dH_2O$ or DI deionized water
$dIH_2O$ deionized water, Milli-Q filtration
g or gm grams
μg micrograms
mg milligrams
kg kilograms
μL and μl microliters
mL and ml milliliters
mm millimeters
μm micrometer
M molar mM millimolar
μM micromolar
U units
sec seconds
min(s) minute/minutes
hr(s) hour/hours
DO dissolved oxygen
Ncm Newton centimeter
ETOH ethanol
eq. equivalents
N normal

1.2. Definitions

The terms "amylase" or "amylolytic enzyme" refer to an enzyme that is, among other things, capable of catalyzing the degradation of starch. α-Amylases are hydrolases that cleave the α-D-(1→4) O-glycosidic linkages in starch. Generally, α-amylases (EC 3.2.1.1; α-D-(1→4)-glucan glucanohydrolase) are defined as endo-acting enzymes cleaving α-D-(1→4) O-glycosidic linkages within the starch molecule in a random fashion yielding polysaccharides containing three or more (1-4)-α-linked D-glucose units. In contrast, the exo-acting amylolytic enzymes, such as β-amylases (EC 3.2.1.2; α-D-(1→4)-glucan maltohydrolase) and some product-specific amylases like maltogenic α-amylase (EC 3.2.1.133) cleave the polysaccharide molecule from the non-reducing end of the substrate. β-amylases, α-glucosidases (EC 3.2.1.20; α-D-glucoside glucohydrolase), glucoamylase (EC 3.2.1.3; α-D-(1→4)-glucan glucohydrolase), and product-specific amylases like the maltotetraosidases (EC 3.2.1.60) and the maltohexaosidases (EC 3.2.1.98) can produce malto-oligosaccharides of a specific length or enriched syrups of specific maltooligosaccharides.

"Enzyme units" herein refer to the amount of product formed per time under the specified conditions of the assay. For example, a "glucoamylase activity unit" (GAU) is defined as the amount of enzyme that produces 1 g of glucose per hour from soluble starch substrate (4% DS) at 60° C., pH 4.2. A "soluble starch unit" (SSU) is the amount of enzyme that produces 1 mg of glucose per minute from soluble starch substrate (4% DS) at pH 4.5, 50° C. DS refers to "dry solids."

As used herein the term "starch" refers to any material comprised of the complex polysaccharide carbohydrates of plants, comprised of amylose and amylopectin with the formula $(C_6H_{10}O_5)_x$, wherein X can be any number. The term includes plant-based materials such as grains, cereal, grasses, tubers and roots, and more specifically materials obtained from wheat, barley, corn, rye, rice, sorghum, brans, cassava, millet, potato, sweet potato, and tapioca. The term "starch" includes granular starch. The term "granular starch" refers to raw, i.e., uncooked starch, e.g., starch that has not been subject to gelatinization.

The terms, "wild-type," "parental," or "reference," with respect to a polypeptide, refer to a naturally-occurring polypeptide that does not include a man-made substitution, insertion, or deletion at one or more amino acid positions. Similarly, the terms "wild-type," "parental," or "reference," with respect to a polynucleotide, refer to a naturally-occurring polynucleotide that does not include a man-made nucleoside change. However, note that a polynucleotide encoding a wild-type, parental, or reference polypeptide is not limited to a naturally-occurring polynucleotide, and encompasses any polynucleotide encoding the wild-type, parental, or reference polypeptide.

Reference to the wild-type protein is understood to include the mature form of the protein. A "mature" polypeptide means a AcAmy1 polypeptide or variant thereof from which a signal sequence is absent. For example, the signal sequence may be cleaved during expression of the polypeptide. The mature AcAmy1 is 617 amino acids in length covering positions 20-636 of SEQ ID NO: 1, where positions are counted from the N-terminus. The signal sequence of the wild-type AcAmy1 is 19 amino acids in length and has the sequence set forth in SEQ ID NO: 3. A mature AcAmy1 or variant thereof may comprise a signal sequence taken from different proteins. The mature protein can be a fusion protein between the mature polypeptide and a signal sequence polypeptide.

The "catalytic core" of AcAmy1 spans residues 20-497 of SEQ ID NO: 1. The "linker" or "linker region" of AcAmy1 span residues 498-528. The amino acid residues 529-636 constitute the "carbohydrate binding domain" of AcAmy1.

The term "variant," with respect to a polypeptide, refers to a polypeptide that differs from a specified wild-type, parental, or reference polypeptide in that it includes one or more naturally-occurring or man-made substitutions, insertions, or deletions of an amino acid. Similarly, the term "variant," with respect to a polynucleotide, refers to a polynucleotide that differs in nucleotide sequence from a specified wild-type, parental, or reference polynucleotide. The identity of the wild-type, parental, or reference polypeptide or polynucleotide will be apparent from context. A "variant" of AcAmy1 and a "variant α-amylase polypeptide" are synonymous herein.

In the case of the present α-amylases, "activity" refers to α-amylase activity, which can be measured as described, herein.

The term "recombinant," when used in reference to a subject cell, nucleic acid, protein or vector, indicates that the subject has been modified from its native state. Thus, for example, recombinant cells express genes that are not found within the native (non-recombinant) form of the cell, or express native genes at different levels or under different conditions than found in nature. Recombinant nucleic acids differ from a native sequence by one or more nucleotides and/or are operably linked to heterologous sequences, e.g., a heterologous promoter in an expression vector. Recombinant proteins may differ from a native sequence by one or more amino acids and/or are fused with heterologous sequences. A vector comprising a nucleic acid encoding an AcAmy1 or variant thereof is a recombinant vector.

The terms "recovered," "isolated," and "separated," refer to a compound, protein (polypeptides), cell, nucleic acid, amino acid, or other specified material or component that is removed from at least one other material or component with which it is naturally associated as found in nature, e.g., an AcAmy1 isolated from an *A. clavatus* sp. cell. An "isolated" AcAmy1 or variant thereof includes, but is not limited to, a culture broth containing secreted AcAmy1 or variant polypeptides and AcAmy1 or variant polypeptides expressed in a heterologous host cell (i.e., a host cell that is not *A. clavatus*).

As used herein, the term "purified" refers to material (e.g., an isolated polypeptide or polynucleotide) that is in a relatively pure state, e.g., at least about 90% pure, at least about 95% pure, at least about 98% pure, or even at least about 99% pure.

The terms "thermostable" and "thermostability," with reference to an enzyme, refer to the ability of the enzyme to retain activity after exposure to an elevated temperature. The thermostability of an enzyme, such as an amylase enzyme, is measured by its half-life ($t_{1/2}$) given in minutes, hours, or days, during which half the enzyme activity is lost under defined conditions. The half-life may be calculated by measuring residual α-amylase activity following exposure to (i.e., challenge by) an elevated temperature.

A "pH range," with reference to an enzyme, refers to the range of pH values under which the enzyme exhibits catalytic activity.

As used herein, the terms "pH stable" and "pH stability," with reference to an enzyme, relate to the ability of the enzyme to retain activity over a wide range of pH values for a predetermined period of time (e.g., 15 min, 30 min., 1 hour).

As used herein, the term "amino acid sequence" is synonymous with the terms "polypeptide," "protein," and "peptide," and are used interchangeably. Where such amino acid sequences exhibit activity, they may be referred to as an "enzyme." The conventional one-letter or three-letter codes for amino acid residues are used, with amino acid sequences being presented in the standard amino-to-carboxy terminal orientation (i.e., N→C).

The term "nucleic acid" encompasses DNA, RNA, heteroduplexes, and synthetic molecules capable of encoding a polypeptide. Nucleic acids may be single stranded or double stranded, and may be chemical modifications. The terms "nucleic acid" and "polynucleotide" are used interchangeably. Because the genetic code is degenerate, more than one codon may be used to encode a particular amino acid, and the present compositions and methods encompass nucleotide sequences that encode a particular amino acid sequence. Unless otherwise indicated, nucleic acid sequences are presented in 5'-to-3' orientation.

As used herein, "hybridization" refers to the process by which one strand of nucleic acid forms a duplex with, i.e., base pairs with, a complementary strand, as occurs during blot hybridization techniques and PCR techniques. Stringent hybridization conditions are exemplified by hybridization under the following conditions: 65° C. and 0.1×SSC (where 1×SSC=0.15 M NaCl, 0.015 M Na$_3$ citrate, pH 7.0). Hybridized, duplex nucleic acids are characterized by a melting temperature ($T_m$), where one half of the hybridized nucleic acids are unpaired with the complementary strand. Mismatched nucleotides within the duplex lower the $T_m$. A nucleic acid encoding a variant α-amylase may have a $T_m$ reduced by 1° C.-3° C. or more compared to a duplex formed between the nucleotide of SEQ ID NO: 2 and its identical complement.

As used herein, a "synthetic" molecule is produced by in vitro chemical or enzymatic synthesis rather than by an organism.

As used herein, the terms "transformed," "stably transformed," and "transgenic," used with reference to a cell means that the cell contains a non-native (e.g., heterologous) nucleic acid sequence integrated into its genome or carried as an episome that is maintained through multiple generations.

The term "introduced" in the context of inserting a nucleic acid sequence into a cell, means "transfection", "transformation" or "transduction," as known in the art.

A "host strain" or "host cell" is an organism into which an expression vector, phage, virus, or other DNA construct, including a polynucleotide encoding a polypeptide of interest (e.g., AcAmy1 or variant thereof) has been introduced. Exemplary host strains are microorganism cells (e.g., bacteria, filamentous fungi, and yeast) capable of expressing the polypeptide of interest and/or fermenting saccharides. The term "host cell" includes protoplasts created from cells.

The term "heterologous" with reference to a polynucleotide or protein refers to a polynucleotide or protein that does not naturally occur in a host cell.

The term "endogenous" with reference to a polynucleotide or protein refers to a polynucleotide or protein that occurs naturally in the host cell.

As used herein, the term "expression" refers to the process by which a polypeptide is produced based on a nucleic acid sequence. The process includes both transcription and translation.

A "selective marker" or "selectable marker" refers to a gene capable of being expressed in a host to facilitate selection of host cells carrying the gene. Examples of selectable markers include but are not limited to antimicrobials (e.g., hygromycin, bleomycin, or chloramphenicol) and/or genes that confer a metabolic advantage, such as a nutritional advantage on the host cell.

A "vector" refers to a polynucleotide sequence designed to introduce nucleic acids into one or more cell types. Vectors include cloning vectors, expression vectors, shuttle vectors, plasmids, phage particles, cassettes and the like.

An "expression vector" refers to a DNA construct comprising a DNA sequence encoding a polypeptide of interest, which coding sequence is operably linked to a suitable control sequence capable of effecting expression of the DNA in a suitable host. Such control sequences may include a promoter to effect transcription, an optional operator sequence to control transcription, a sequence encoding suitable ribosome binding sites on the mRNA, enhancers and sequences which control termination of transcription and translation.

The term "operably linked" means that specified components are in a relationship (including but not limited to juxtaposition) permitting them to function in an intended manner. For example, a regulatory sequence is operably linked to a coding sequence such that expression of the coding sequence is under control of the regulatory sequences.

A "signal sequence" is a sequence of amino acids attached to the N-terminal portion of a protein, which facilitates the secretion of the protein outside the cell. The mature form of an extracellular protein lacks the signal sequence, which is cleaved off during the secretion process.

As used herein, "biologically active" refer to a sequence having a specified biological activity, such an enzymatic activity.

As used herein, a "swatch" is a piece of material such as a fabric that has a stain applied thereto. The material can be, for example, fabrics made of cotton, polyester or mixtures of natural and synthetic fibers. The swatch can further be paper, such as filter paper or nitrocellulose, or a piece of a hard material such as ceramic, metal, or glass. For amylases, the stain is starch based, but can include blood, milk, ink, grass, tea, wine, spinach, gravy, chocolate, egg, cheese, clay, pigment, oil, or mixtures of these compounds.

As used herein, a "smaller swatch" is a section of the swatch that has been cut with a single hole punch device, or has been cut with a custom manufactured 96-hole punch device, where the pattern of the multi-hole punch is matched to standard 96-well microtiter plates, or the section has been otherwise removed from the swatch. The swatch can be of textile, paper, metal, or other suitable material. The smaller swatch can have the stain affixed either before or after it is placed into the well of a 24-, 48- or 96-well microtiter plate. The smaller swatch can also be made by applying a stain to a small piece of material. For example, the smaller swatch can be a stained piece of fabric ⅝" or 0.25" in diameter. The custom manufactured punch is designed in such a manner that it delivers 96 swatches simultaneously to all wells of a 96-well plate. The device allows delivery of more than one swatch per well by simply loading the same 96-well plate multiple times. Multi-hole punch devices can be conceived of to deliver simultaneously swatches to any format plate, including but not limited to 24-well, 48-well, and 96-well plates. In another conceivable method, the soiled test platform can be a bead made of metal, plastic, glass, ceramic, or another suitable material that is coated with the soil substrate. The one or more coated beads are then placed into wells of 96-, 48-, or 24-well plates or larger formats, containing suitable buffer and enzyme.

As used herein, "a cultured cell material comprising an AcAmy1 or variant thereof," or similar language, refers to a cell lysate or supernatant (including media) that includes an AcAmy1 or variant thereof as a component. The cell material may be from a heterologous host that is grown in culture for the purpose of producing the AcAmy1 or variant thereof.

"Percent sequence identity" means that a variant has at least a certain percentage of amino acid residues identical to a wild-type AcAmy1, when aligned using the CLUSTAL W algorithm with default parameters. See Thompson et al. (1994) *Nucleic Acids Res*. 22:4673-4680. Default parameters for the CLUSTAL W algorithm are:

Gap opening penalty: 10.0
Gap extension penalty: 0.05
Protein weight matrix: BLOSUM series
DNA weight matrix: IUB
Delay divergent sequences %: 40
Gap separation distance: 8
DNA transitions weight: 0.50
List hydrophilic residues: GPSNDQEKR
Use negative matrix: OFF
Toggle Residue specific penalties: ON
Toggle hydrophilic penalties: ON
Toggle end gap separation penalty OFF.

Deletions are counted as non-identical residues, compared to a reference sequence. Deletions occurring at either termini are included. For example, a variant with five amino acid deletions of the C-terminus of the mature AcAmy1 polypeptide of SEQ ID NO: 1 would have a percent sequence identity of 99% (612/617 identical residues×100, rounded to the nearest whole number) relative to the mature polypeptide. Such a variant would be encompassed by a variant having "at least 99% sequence identity" to a mature AcAmy1 polypeptide.

"Fused" polypeptide sequences are connected, i.e., operably linked, via a peptide bond between the two polypeptide sequences.

The term "filamentous fungi" refers to all filamentous forms of the subdivision Eumycotina.

The term "degree of polymerization" (DP) refers to the number (n) of anhydro-glucopyranose units in a given saccharide. Examples of DP1 are the monosaccharides glucose and fructose. Examples of DP2 are the disaccharides maltose and sucrose. The term "DE," or "dextrose equivalent," is defined as the percentage of reducing sugar, i.e., D-glucose, as a fraction of total carbohydrate in a syrup.

As used herein the term "dry solids content" (ds) refers to the total solids of a slurry in a dry weight percent basis. The term "slurry" refers to an aqueous mixture containing insoluble solids.

The phrase "simultaneous saccharification and fermentation (SSF)" refers to a process in the production of biochemicals in which a microbial organism, such as an ethanologenic microorganism, and at least one enzyme, such as AcAmy1 or a variant thereof, are present during the same process step. SSF includes the contemporaneous hydrolysis of starch substrates (granular, liquefied, or solubilized) to saccharides, including glucose, and the fermentation of the saccharides into alcohol or other biochemical or biomaterial in the same reactor vessel.

As used herein "ethanologenic microorganism" refers to a microorganism with the ability to convert a sugar or oligosaccharide to ethanol.

The term "fermented beverage" refers to any beverage produced by a method comprising a fermentation process, such as a microbial fermentation, e.g., a bacterial and/or yeast fermentation.

"Beer" is an example of such a fermented beverage, and the term "beer" is meant to comprise any fermented wort produced by fermentation/brewing of a starch-containing plant material. Often, beer is produced exclusively from malt or adjunct, or any combination of malt and adjunct. Examples of beers include: full malted beer, beer brewed under the "Reinheitsgebot," ale, IPA, lager, bitter, Happoshu (second beer), third beer, dry beer, near beer, light beer, low alcohol beer, low calorie beer, porter, bock beer, stout, malt liquor, non-alcoholic beer, non-alcoholic malt liquor and the like, but also alternative cereal and malt beverages such as fruit flavored malt beverages, e.g., citrus flavored, such as lemon-, orange-, lime-, or berry-flavored malt beverages, liquor flavored malt beverages, e.g., vodka-, rum-, or tequila-flavored malt liquor, or coffee flavored malt beverages, such as caffeine-flavored malt liquor, and the like.

The term "malt" refers to any malted cereal grain, such as malted barley or wheat.

The term "adjunct" refers to any starch and/or sugar containing plant material which is not malt, such as barley or wheat malt. Examples of adjuncts include common corn grits, refined corn grits, brewer's milled yeast, rice, sorghum, refined corn starch, barley, barley starch, dehusked barley, wheat, wheat starch, torrified cereal, cereal flakes, rye, oats, potato, tapioca, cassava and syrups, such as corn syrup, sugar cane syrup, inverted sugar syrup, barley and/or wheat syrups, and the like.

The term "mash" refers to an aqueous slurry of any starch and/or sugar containing plant material, such as grist, e.g., comprising crushed barley malt, crushed barley, and/or other adjunct or a combination thereof, mixed with water later to be separated into wort and spent grains.

The term "wort" refers to the unfermented liquor run-off following extracting the grist during mashing.

"Iodine-positive starch" or "IPS" refers to (1) amylose that is not hydrolyzed after liquefaction and saccharification, or (2) a retrograded starch polymer. When saccharified starch or saccharide liquor is tested with iodine, the high DPn amylose or the retrograded starch polymer binds iodine and produces a characteristic blue color. The saccharide liquor is thus termed "iodine-positive saccharide," "blue saccharide," or "blue sac."

The terms "retrograded starch" or "starch retrogradation" refer to changes that occur spontaneously in a starch paste or gel on ageing.

The term "about" refers to ±15% to the referenced value.

2. *Aspergillus clavatus* α-Amylase (AcAmy1) and Variants Thereof

An isolated and/or purified AcAmy1 polypeptide from *A. clavatus* sp. or a variant thereof having α-amylase activity is provided. The AcAmy1 polypeptide can be the mature AcAmy1 polypeptide comprising residues 20-636 of the polypeptide sequence depicted in SEQ ID NO: 1. The polypeptides may be fused to additional amino acid sequences at the N-terminus and/or C-terminus. Additional N-terminal sequences can be a signal peptide, which may have the sequence shown in SEQ ID NO: 3, for example. Other amino acid sequences fused at either termini include fusion partner polypeptides useful for labeling or purifying the protein.

For example, a known α-amylase from *A. clavatus* is the α-amylase from *A. clavatus* NRRL1. *A. clavatus* NRRL1 α-amylase precursor, i.e., containing a signal peptide has the following amino acid sequence (SEQ ID NO: 1):

*MKLLALTTAFALLGKGVFG*LTPAEWRGQSIYFLITDRFARTDGSTTAPCD

LSQRAYCGGSWQGIIKQLDYIQGMGFTAIWITPITEQIPQDTAEGSAFHG

YWQKDIYNVNSHFGTADDIRALSKALHDRGMYLMIDVVANHMGYNGPGAS

TDFSTFTPFNSASYFHSYCPINNYNDQSQVENCWLGDNTVALADLYTQHS

DVRNIWYSWIKEIVGNYSADGLRIDTVKHVEKDFWTGYTQAAGVYTVGEV

LDGDPAYTCPYQGYVDGVLNYPIYYPLLRAFESSSGSMGDLYNMINSVAS

DCKDPTVLGSFIENHDNPRFASYTKDMSQAKAVISYVILSDGIPIIYSGQ

EQHYSGGNDPYNREAIWLSGYSTTSELYKFIATTNKIRQLAISKDSSYLT

SRNNPFYTDSNTIAMRKGSGGSQVITVLSNSGSNGGSYTLNLGNSGYSSG

ANLVEVYTCSSVTVGSDGKIPVPMASGLPRVLVPASWMSGSGLCGSSSTT

TLVTATTTPTGSSSSTTLATAVTTPTGSCKTATTVPVVLEESVRTSYGEN

IFISGSIPQLGSWNPDKAVALSSSQYTSSNPLWAVTLDLPVGTSFEYKFL

KKEQNGGVAWENDPNRSYTVPEACAGTSQKVDSSWR.

See NCBI Reference Number XP_001272245.1 (>gi|121708778|ref|XP_001272245.1| alpha amylase, putative [*Aspergillus clavatus* NRRL 1]).

The bolded amino acids above constitute a C-terminal carbohydrate binding (CBM) domain (SEQ ID NO: 10). A glycosylated linker region (highlighted, bolded amino acids above; SEQ ID NO: 11) connects the N-terminal catalytic core with the CBM domain. The CBM domain in AcAmy1 is conserved with a CBM20 domain found in a large number of starch degrading enzymes, including alpha-amylases, beta-amylases, glucoamylases, and cyclodextrin glucanotransferases. CBM20 folds as an antiparallel beta-barrel structure with two starch binding sites 1 and 2. These two sites are thought to differ functionally: site 1 may act as the initial starch recognition site, whereas site 2 may be involved in specific recognition of appropriate regions of starch. See Sorimachi et al. (1997) "Solution structure of the granular starch binding domain of *Aspergillus niger* glucoamylase bound to beta-cyclodextrin," Structure 5(5): 647-61. Residues in the AcAmy1 CBM domain that are conserved with starch binding sites 1 and 2 are indicated in the sequence below by the numbers 1 and 2, respectively:

```
                                        (SEQ ID NO: 10)
CKTATTVPVVLEESVRTSYGENIFISGSIPQLGSWNPDKAVALSSS
         222222       1    1 1111       2

QYTSSNPLWAVTLDLPVGTSFEYKFLKKEQNGGVAWENDPNRSYTV
2222   22                                    1

PEACAGTSQKVDSSWR.
```

A variant AcAmy1 may comprise some or no amino acid residues of the CBM domain of SEQ ID NO: 10 or the linker of SEQ ID NO: 11. A variant alternatively may comprise a CBM domain with at least 80%, 85%, 90%, 95%, or 98% sequence identity to the CBM domain of SEQ ID NO: 10. A variant may comprise a heterologous or an engineered CBM20 domain.

The AcAmy1 or variant thereof may be expressed in a eukaryotic host cell, e.g., a filamentous fungal cell, that allows proper glycosylation of the linker sequence, for example.

A representative polynucleotide encoding AcAmy1 is the polynucleotide sequence set forth in SEQ ID NO: 2. NCBI Reference Number ACLA_052920 discloses such a polynucleotide. The polypeptide sequence, MKLLALTTA-FALLGKGVFG (SEQ ID NO: 3), shown in italics above, is an N-terminal signal peptide that is cleaved when the protein is expressed in an appropriate host cell.

The polypeptide sequence of AcAmy1 is similar to other fungal alpha-amylases. For example, AcAmy1 has the high sequence identity to the following fungal α-amylases:

77% sequence identity to the putative α-amylase from *Talaromyces stipitatus* ATCC 10500 (XP_00248703.1; SEQ ID NO: 4); and 72% sequence identity to protein AN3402.2 from *Aspergillus nidulans* FGSC A4 (XP_661006.1; SEQ ID NO: 5). Sequence identity was determined by a BLAST alignment, using the mature form of the AcAmy1 of SEQ ID NO: 1 (i.e., residues 20-636) as the query sequence. See Altschul et al. (1990) *J. Mol. Biol.* 215: 403-410.

A variant of an AcAmy1 polypeptide is provided. The variant can consist of or comprise a polypeptide with at least 80%, at least 90%, at least 95%, at least 98%, or at least 99% amino acid sequence identity to the polypeptide of residues 20-636 or residues 20-497 of SEQ ID NO:1, wherein the variant comprises one or more amino acid modifications selected from a substitution, insertion, or deletion of one or more corresponding amino acids in SEQ ID NO: 4, 5, 12, and/or 13. For example, a variant consisting of a polypeptide with at least 99% sequence identity to the polypeptide of residues 20-636 of SEQ ID NO:1 may have one to six amino acid substitutions, insertions, or deletions, compared to the AcAmy1 of SEQ ID NO: 1. By comparison, a variant consisting of a polypeptide with at least 99% sequence identity to the polypeptide of residues 20-497 of SEQ ID NO:1 would have up to five amino acid modifications. The insertions or deletions may be at either termini of the polypeptide, for example. Alternatively, the variant can "comprise" a polypeptide consisting of a polypeptide with at least 80%, at least 90%, at least 95%, at least 98%, or at least 99% amino acid sequence identity to the polypeptide of residues 20-636 or 20-497 of SEQ ID NO:1. In such a variant, additional amino acid residues may be fused to either termini of the polypeptide. For example, the variant may comprise the signal sequence of SEQ ID NO: 3 fused in-fame with a polypeptide with one or more amino acid substitutions or deletions compared to the polypeptide of residues 20-636 of SEQ ID NO:1. The variant may be glycosylated, regardless of whether the variant "comprises" or "consists" of a given amino acid sequence.

A ClustalW alignment between AcAmy1 (SEQ ID NO: 1) and the α-amylases from *T. stipitatus* ATCC 10500 (SEQ ID NO: 4), *A. nidulans* FGSC A4 (SEQ ID NO: 5), *A. fumigatus* Af293 (SEQ ID NO: 12), and *A. terreus* NIH2624 (SEQ ID NO: 13) is shown in FIG. 1. See Thompson et al. (1994) *Nucleic Acids Res.* 22:4673-4680. As a general rule, the degree to which an amino acid is conserved in an alignment of related protein sequences is proportional to the relative importance of the amino acid position to the function of the protein. That is, amino acids that are common in all related sequences likely play an important functional role and cannot be easily substituted. Likewise, positions that vary between the sequences likely can be substituted with other amino acids or otherwise modified, while maintaining the activity of the protein.

The crystal structure of *A. niger* α-amylase has been determined, including a complex of enzyme with maltose bound to its active site. See, e.g., Vujicić-Zagar et al. (2006) "Monoclinic crystal form of *Aspergillus niger* α-amylase in complex with maltose at 1.8 Å resolution," *Acta Crystallogr. Sect. F: Struct. Biol. Cryst. Commun.* 62(8):716-21. The *A. niger* α-amylase disclosed in Vujicić-Zagar (2006) is also known as TAKA-amylase, an *A. oryzae* α-amylase homologue. The amino acid sequence of TAKA-amylase (SEQ ID NO: 6) has a 68% sequence identity to AcAmy1 over AcAmy1 residues 21-497, when aligned using the BLAST algorithm. Given the relatively high amino acid sequence conservation between TAKA-amylase and AcAmy1, AcAmy1 is expected to adopt many of the secondary structures and possess similar structure/function relationships as TAKA-amylase. For example, AcAmy1 is expected to have a similar high affinity $Ca^{2+}$ binding site and maltose binding cleft as TAKA-amylase. Consistent with this expectation, the three acidic amino acids that participate in the hydrolysis reaction catalyzed by TAKA-amylase, D206, E230, and D297, all are conserved in the wild-type AcAmy1. TAKA-amylase positions Y155, L166, D233, and D235, located near the binding cleft, also are conserved in AcAmy1. Other conserved AcAmy1 positions correspond to N121, E162, D175, and H210 of TAKA-amylase, which constitute the high affinity $Ca^{2+}$ binding site. See Vujicić-Zagar (2006).

The alignments shown in FIG. 1 and the structural relationships ascertained from the TAKA-amylase crystal structure, for example, can guide the construction of variant AcAmy1 polypeptides having α-amylase activity. Variant AcAmy1 polypeptides include, but are not limited to, those with an amino acid modification selected from a substitution, insertion, or deletion of a corresponding amino acid in SEQ ID NO: 4, 5, 12, and/or 13. Correspondence between positions in AcyAmy1 and the α-amylases of SEQ ID NOS: 4, 5, 12, and 13 is determined with reference to the alignment shown in FIG. 1. For example, a variant AcAmy1 polypeptide can have the substitution G27S, where serine is the corresponding amino acid in SEQ ID NOS: 4, 5, 12, and 13, referring to the alignment in FIG. 1. Variant AcAmy1 polypeptides also include, but are not limited to, those with 1, 2, 3, or 4 randomly selected amino acid modifications. Amino acid modifications can be made using well-known methodologies, such as oligo-directed mutagenesis.

Nucleic acids encoding the AcAmy1 polypeptide or variant thereof also are provided. A nucleic acid encoding AcAmy1 can be genomic DNA. Or, the nucleic acid can be a cDNA comprising SEQ ID NO: 2. As is well understood by one skilled in the art, the genetic code is degenerate, meaning that multiple codons in some cases may encode the same amino acid. Nucleic acids include all genomic DNA, mRNA and cDNA sequences that encode an AcAmy1 or variant thereof.

The AcAmy1 or variants thereof may be "precursor," "immature," or "full-length," in which case they include a signal sequence, or "mature," in which case they lack a signal sequence. The variant α-amylases may also be truncated at the N- or C-termini, so long as the resulting polypeptides retain α-amylase activity.

2.1. AcAmy1 Variant Characterization

Variant AcAmy1 polypeptides retain α-amylase activity. They may have a specific activity higher or lower than the wild-type AcAmy1 polypeptide. Additional characteristics of the AcAmy1 variant include stability, pH range, oxidation stability, and thermostability, for example. For example, the variant may be pH stable for 24-60 hours from pH 3 to about pH 7, e.g., pH 3.0-7.5; pH 3.5-5.5; pH 3.5-5.0; pH 3.5-4.8; pH 3.8-4.8; pH 3.5, pH 3.8, or pH 4.5. An AcAmy1 variant can be expressed at higher levels than the wild-type AcAmy1, while retaining the performance characteristics of the wild-type AcAmy1. AcAmy1 variants also may have altered oxidation stability in comparison to the parent α-amylase. For example, decreased oxidation stability may be advantageous in composition for starch liquefaction. The variant AcAmy1 have altered thermostability compared to the wild-type α-amylase. Such AcAmy1 variants are advantageous for use in baking or other processes that require elevated temperatures. Levels of expression and enzyme activity can be assessed using standard assays known to the artisan skilled in this field, including those disclosed below.

3. Production of AcAmy1 and Variants Thereof

The AcAmy1 or variant thereof can be isolated from a host cell, for example by secretion of the AcAmy1 or variant from the host cell. A cultured cell material comprising AcAmy1 or variant thereof can be obtained following secretion of the AcAmy1 or variant from the host cell. The AcAmy1 or variant optionally is purified prior to use. The AcAmy1 gene can be cloned and expressed according to methods well known in the art. Suitable host cells include bacterial, plant, or yeast cells, e.g., filamentous fungal cells. Particularly useful host cells include *Aspergillus clavatus* or *Trichoderma reesei*. Other host cells include bacterial cells, e.g., *Bacillus subtilis* or *B. licheniformis*.

The host cell further may express a nucleic acid encoding a homologous or heterologous glucoamylase, i.e., a glucoamylase that is not the same species as the host cell, or one or more other enzymes. The glucoamylase may be a variant glucoamylase, such as one of the glucoamylase variants disclosed in U.S. Pat. No. 8,058,033 (Danisco US Inc.), for example. Additionally, the host may express one or more accessory enzymes, proteins, peptides. These may benefit liquefaction, saccharification, fermentation, SSF, etc processes. Furthermore, the host cell may produce biochemicals in addition to enzymes used to digest the various feedstock(s). Such host cells may be useful for fermentation or simultaneous saccharification and fermentation processes to reduce or eliminate the need to add enzymes.

3.1. Vectors

A DNA construct comprising a nucleic acid encoding an AcAmy1 or variant thereof can be constructed to be expressed in a host cell. Representative nucleic acids that encode AcAmy1 include SEQ ID NO: 2. Because of the well-known degeneracy in the genetic code, variant polynucleotides that encode an identical amino acid sequence can be designed and made with routine skill. It is also well-known in the art to optimize codon use for a particular host cell. Nucleic acids encoding an AcAmy1 or variant thereof can be incorporated into a vector. Vectors can be transferred to a host cell using well-known transformation techniques, such as those disclosed below.

The vector may be any vector that can be transformed into and replicated within a host cell. For example, a vector comprising a nucleic acid encoding an AcAmy1 or variant thereof can be transformed and replicated in a bacterial host cell as a means of propagating and amplifying the vector. The vector also may be transformed into an expression host, so that the encoding nucleic acids can be expressed as a functional AcAmy1 or variant thereof. Host cells that serve as expression hosts can include filamentous fungi, for example. The Fungal Genetics Stock Center (FGSC) Catalogue of Strains lists suitable vectors for expression in fungal host cells. See FGSC, Catalogue of Strains, University of Missouri, at www.fgsc.net (last modified Jan. 17, 2007). FIG. 2 shows a plasmid map of a representative vector, pJG153(Tex3gM-AcAmy1). pJG153 is a promoterless Cre expression vector that can be replicated in a bacterial host. See Harrison et al. (June 2011) *Applied Environ. Microbiol.* 77: 3916-22. pJG153(Tex3gM-AcAmy1) is a pJG153 vector that comprises a nucleic acid encoding an AcAmy1 and that can express the nucleic acid in a fungal host cell. pJG153 (Tex3gM-AcAmy1) can be modified with routine skill to comprise and express a nucleic acid encoding an AcAmy1 variant.

A nucleic acid encoding an AcAmy1 or a variant thereof can be operably linked to a suitable promoter, which allows transcription in the host cell. The promoter may be any DNA sequence that shows transcriptional activity in the host cell of choice and may be derived from genes encoding proteins either homologous or heterologous to the host cell. Exemplary promoters for directing the transcription of the DNA sequence encoding an AcAmy1 or variant thereof, especially in a bacterial host, are the promoter of the lac operon of *E. coli*, the *Streptomyces coelicolor* agarase gene dagA or celA promoters, the promoters of the *Bacillus licheniformis* α-amylase gene (amyL), the promoters of the *Bacillus stearothermophilus* maltogenic amylase gene (amyM), the promoters of the *Bacillus amyloliquefaciens* α-amylase (amyQ), the promoters of the *Bacillus subtilis* xylA and xylB genes etc. For transcription in a fungal host, examples of useful promoters are those derived from the gene encoding *Aspergillus oryzae* TAKA amylase, *Rhizomucor miehei* aspartic proteinase, *Aspergillus niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase, or *A. nidulans* acetamidase. When a gene encoding an AcAmy1 or variant thereof is expressed in a bacterial species such as *E. coli*, a suitable promoter can be selected, for example, from a bacteriophage promoter including a T7 promoter and a phage lambda promoter. Examples of suitable promoters for the expression in a yeast species include but are not limited to the Gal 1 and Gal 10 promoters of *Saccharomyces cerevisiae* and the *Pichia pastoris* AOX1 or AOX2 promoters. The pJG153 vector depicted in FIG. 2, for example, contains a cbh1 promoter operably linked to AcAmy1. cbh1 is an endogenous, inducible promoter from *T. reesei*. See Liu et al. (2008) "Improved heterologous gene expression in *Trichoderma reesei* by cellobiohydrolase I gene (cbh1) promoter optimization," *Acta Biochim. Biophys. Sin (Shanghai)* 40(2): 158-65.

The coding sequence can be operably linked to a signal sequence. The DNA encoding the signal sequence may be the DNA sequence naturally associated with the AcAmy1 gene to be expressed. For example, the DNA may encode the AcAmy1 signal sequence of SEQ ID NO: 3 operably linked to a nucleic acid encoding an AcAmy1 or a variant thereof. The DNA encodes a signal sequence from a species other than *A. clavatus*. A signal sequence and a promoter sequence comprising a DNA construct or vector can be introduced into a fungal host cell and can be derived from the same source. For example, the signal sequence is the cbh1 signal sequence that is operably linked to a cbh1 promoter.

An expression vector may also comprise a suitable transcription terminator and, in eukaryotes, polyadenylation sequences operably linked to the DNA sequence encoding an AcAmy1 or variant thereof. Termination and polyadenylation sequences may suitably be derived from the same sources as the promoter.

The vector may further comprise a DNA sequence enabling the vector to replicate in the host cell. Examples of such sequences are the origins of replication of plasmids pUC19, pACYC177, pUB110, pE194, pAMB1, and pIJ702.

The vector may also comprise a selectable marker, e.g., a gene the product of which complements a defect in the isolated host cell, such as the dal genes from *B. subtilis* or *B. licheniformis*, or a gene that confers antibiotic resistance such as, e.g., ampicillin, kanamycin, chloramphenicol or tetracycline resistance. Furthermore, the vector may comprise *Aspergillus* selection markers such as amdS, argB, niaD and xxsC, a marker giving rise to hygromycin resistance, or the selection may be accomplished by co-transformation, such as known in the art. See e.g., International PCT Application WO 91/17243.

Intracellular expression may be advantageous in some respects, e.g., when using certain bacteria or fungi as host cells to produce large amounts of an AcAmy1 or variant thereof for subsequent purification. Extracellular secretion of the AcAmy1 or variant thereof into the culture medium can also be used to make a cultured cell material comprising the isolated AcAmy1 or variant thereof.

The expression vector typically includes the components of a cloning vector, such as, for example, an element that permits autonomous replication of the vector in the selected host organism and one or more phenotypically detectable markers for selection purposes. The expression vector normally comprises control nucleotide sequences such as a promoter, operator, ribosome binding site, translation initiation signal and optionally, a repressor gene or one or more activator genes. Additionally, the expression vector may comprise a sequence coding for an amino acid sequence capable of targeting the AcAmy1 or variant thereof to a host cell organelle such as a peroxisome, or to a particular host cell compartment. Such a targeting sequence includes but is not limited to the sequence, SKL. For expression under the direction of control sequences, the nucleic acid sequence of the AcAmy1 or variant thereof is operably linked to the control sequences in proper manner with respect to expression.

The procedures used to ligate the DNA construct encoding an AcAmy1 or variant thereof, the promoter, terminator and other elements, respectively, and to insert them into suitable vectors containing the information necessary for replication, are well known to persons skilled in the art (see, e.g., Sambrook et al., MOLECULAR CLONING: A LABORATORY MANUAL, 2$^{nd}$ ed., Cold Spring Harbor, 1989, and 3$^{rd}$ ed., 2001).

3.2. Transformation and Culture of Host Cells

An isolated cell, either comprising a DNA construct or an expression vector, is advantageously used as a host cell in the recombinant production of an AcAmy1 or variant thereof. The cell may be transformed with the DNA construct encoding the enzyme, conveniently by integrating the DNA construct (in one or more copies) in the host chromosome. This integration is generally considered to be an advantage, as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described above in connection with the different types of host cells.

Examples of suitable bacterial host organisms are Gram positive bacterial species such as Bacillaceae including *Bacillus subtilis, Bacillus licheniformis, Bacillus lentos, Bacillus* brevis, Geobacillus (formerly Bacillus) stearothermophilus, Bacillus alkalophilus, Bacillus amyloliquefaciens, Bacillus coagulans, Bacillus lautus, Bacillus megaterium, and Bacillus thuringiensis; Streptomyces species such as Streptomyces murinus; lactic acid bacterial species including Lactococcus sp. such as Lactococcus lactis; Lactobacillus sp. including Lactobacillus reuteri; Leuconostoc sp.; Pediococcus sp.; and Streptococcus sp. Alternatively, strains of a Gram negative bacterial species belonging to Enterobacteriaceae including E. coli, or to Pseudomonadaceae can be selected as the host organism.

A suitable yeast host organism can be selected from the biotechnologically relevant yeasts species such as but not limited to yeast species such as Pichia sp., Hansenula sp., or Kluyveromyces, Yarrowinia, Schizosaccharomyces species or a species of Saccharomyces, including Saccharomyces cerevisiae or a species belonging to Schizosaccharomyces such as, for example, S. pombe species. A strain of the methylotrophic yeast species, Pichia pastoris, can be used as the host organism. Alternatively, the host organism can be a Hansenula species. Suitable host organisms among filamentous fungi include species of Aspergillus, e.g., Aspergillus niger, Aspergillus oryzae, Aspergillus tubigensis, Aspergillus awamori, or Aspergillus nidulans. Alternatively, strains of a Fusarium species, e.g., Fusarium oxysporum or of a Rhizomucor species such as Rhizomucor miehei can be used as the host organism. Other suitable strains include Thermomyces and Mucor species. In addition, Trichoderma sp. can be used as a host. A suitable procedure for transformation of Aspergillus host cells includes, for example, that described in EP 238023. The AcAmy1 or variant thereof expressed by a fungal host cell can be glycosylated, i.e., the AcAmy1 or variant thereof will comprise a glycosyl moiety. The glycosylation pattern can be the same as present in the wild-type AcAmy1.

It is advantageous to delete genes from expression hosts, where the gene deficiency can be cured by the transformed expression vector. Known methods may be used to obtain a fungal host cell having one or more inactivated genes. Gene inactivation may be accomplished by complete or partial deletion, by insertional inactivation or by any other means that renders a gene nonfunctional for its intended purpose, such that the gene is prevented from expression of a functional protein. Any gene from a Trichoderma sp. or other filamentous fungal host that has been cloned can be deleted, for example, cbh1, cbh2, egl1, and egl2 genes. Gene deletion may be accomplished by inserting a form of the desired gene to be inactivated into a plasmid by methods known in the art.

Introduction of a DNA construct or vector into a host cell includes techniques such as transformation; electroporation; nuclear microinjection; transduction; transfection, e.g., lipofection mediated and DEAE-Dextrin mediated transfection; incubation with calcium phosphate DNA precipitate; high velocity bombardment with DNA-coated microprojectiles; and protoplast fusion. General transformation techniques are known in the art. See, e.g., Sambrook et al. (2001), supra. The expression of heterologous protein in Trichoderma is described, for example, in U.S. Pat. No. 6,022,725. Reference is also made to Cao et al. (2000) Science 9:991-1001 for transformation of Aspergillus strains. Genetically stable transformants can be constructed with vector systems whereby the nucleic acid encoding an AcAmy1 or variant thereof is stably integrated into a host cell chromosome. Transformants are then selected and purified by known techniques.

The preparation of Trichoderma sp. for transformation, for example, may involve the preparation of protoplasts from fungal mycelia. See Campbell et al. (1989) Curr. Genet. 16: 53-56. The mycelia can be obtained from germinated vegetative spores. The mycelia are treated with an enzyme that digests the cell wall, resulting in protoplasts. The protoplasts are protected by the presence of an osmotic stabilizer in the suspending medium. These stabilizers include sorbitol, mannitol, potassium chloride, magnesium sulfate, and the like. Usually the concentration of these stabilizers varies between 0.8 M and 1.2 M, e.g., a 1.2 M solution of sorbitol can be used in the suspension medium.

Uptake of DNA into the host Trichoderma sp. strain depends upon the calcium ion concentration. Generally, between about 10-50 mM $CaCl_2$ is used in an uptake solution. Additional suitable compounds include a buffering system, such as TE buffer (10 mM Tris, pH 7.4; 1 mM EDTA) or 10 mM MOPS, pH 6.0 and polyethylene glycol. The polyethylene glycol is believed to fuse the cell membranes, thus permitting the contents of the medium to be delivered into the cytoplasm of the Trichoderma sp. strain. This fusion frequently leaves multiple copies of the plasmid DNA integrated into the host chromosome.

Usually transformation of Trichoderma sp. uses protoplasts or cells that have been subjected to a permeability treatment, typically at a density of $10^5$ to $10^7$/mL, particularly $2 \times 10^6$/mL. A volume of 100 µL of these protoplasts or cells in an appropriate solution (e.g., 1.2 M sorbitol and 50 mM $CaCl_2$) may be mixed with the desired DNA. Generally, a high concentration of PEG is added to the uptake solution. From 0.1 to 1 volume of 25% PEG 4000 can be added to the protoplast suspension; however, it is useful to add about 0.25 volumes to the protoplast suspension. Additives, such as dimethyl sulfoxide, heparin, spermidine, potassium chloride and the like, may also be added to the uptake solution to facilitate transformation. Similar procedures are available for other fungal host cells. See, e.g., U.S. Pat. No. 6,022,725.

3.3. Expression

A method of producing an AcAmy1 or variant thereof may comprise cultivating a host cell as described above under conditions conducive to the production of the enzyme and recovering the enzyme from the cells and/or culture medium.

The medium used to cultivate the cells may be any conventional medium suitable for growing the host cell in question and obtaining expression of an AcAmy1 or variant thereof. Suitable media and media components are available from commercial suppliers or may be prepared according to published recipes (e.g., as described in catalogues of the American Type Culture Collection).

An enzyme secreted from the host cells can be used in a whole broth preparation. In the present methods, the preparation of a spent whole fermentation broth of a recombinant microorganism can be achieved using any cultivation method known in the art resulting in the expression of an α-amylase. Fermentation may, therefore, be understood as comprising shake flask cultivation, small- or large-scale fermentation (including continuous, batch, fed-batch, or solid state fermentations) in laboratory or industrial fermenters performed in a suitable medium and under conditions allowing the amylase to be expressed or isolated. The term "spent whole fermentation broth" is defined herein as unfractionated contents of fermentation material that includes culture medium, extracellular proteins (e.g., enzymes), and cellular biomass. It is understood that the term "spent whole fermentation broth" also encompasses cellular biomass that has been lysed or permeabilized using methods well known in the art.

An enzyme secreted from the host cells may conveniently be recovered from the culture medium by well-known procedures, including separating the cells from the medium by centrifugation or filtration, and precipitating proteinaceous components of the medium by means of a salt such as ammonium sulfate, followed by the use of chromatographic procedures such as ion exchange chromatography, affinity chromatography, or the like.

The polynucleotide encoding AcAmy1 or a variant thereof in a vector can be operably linked to a control sequence that is capable of providing for the expression of the coding sequence by the host cell, i.e. the vector is an expression vector. The control sequences may be modified, for example by the addition of further transcriptional regulatory elements to make the level of transcription directed by the control sequences more responsive to transcriptional modulators. The control sequences may in particular comprise promoters.

Host cells may be cultured under suitable conditions that allow expression of the AcAmy1 or variant thereof. Expression of the enzymes may be constitutive such that they are continually produced, or inducible, requiring a stimulus to initiate expression. In the case of inducible expression, protein production can be initiated when required by, for example, addition of an inducer substance to the culture medium, for example dexamethasone or IPTG or Sophorose. Polypeptides can also be produced recombinantly in an in vitro cell-free system, such as the TNT™ (Promega) rabbit reticulocyte system.

An expression host also can be cultured in the appropriate medium for the host, under aerobic conditions. Shaking or a combination of agitation and aeration can be provided, with production occurring at the appropriate temperature for that host, e.g., from about 25° C. to about 75° C. (e.g., 30° C. to 45° C.), depending on the needs of the host and production of the desired AcAmy1 or variant thereof. Culturing can occur from about 12 to about 100 hours or greater (and any hour value there between, e.g., from 24 to 72 hours). Typically, the culture broth is at a pH of about 4.0 to about 8.0, again depending on the culture conditions needed for the host relative to production of an AcAmy1 or variant thereof.

3.4. Identification of AcAmy1 Activity

To evaluate the expression of an AcAmy1 or variant thereof in a host cell, assays can measure the expressed protein, corresponding mRNA, or α-amylase activity. For example, suitable assays include Northern blotting, reverse transcriptase polymerase chain reaction, and in situ hybridization, using an appropriately labeled hybridizing probe. Suitable assays also include measuring AcAmy1 activity in a sample, for example, by assays directly measuring reducing sugars such as glucose in the culture media. For example, glucose concentration may be determined using glucose reagent kit No. 15-UV (Sigma Chemical Co.) or an instrument, such as Technicon Autoanalyzer. α-Amylase activity also may be measured by any known method, such as the PAHBAH or ABTS assays, described below.

3.5. Methods for Purifying AcAmy1 and Variants Thereof.

Fermentation, separation, and concentration techniques are well known in the art and conventional methods can be used in order to prepare a concentrated AcAmy1 or variant α-amylase polypeptide-containing solution.

After fermentation, a fermentation broth is obtained, the microbial cells and various suspended solids, including residual raw fermentation materials, are removed by conventional separation techniques in order to obtain an amylase solution. Filtration, centrifugation, microfiltration, rotary vacuum drum filtration, ultrafiltration, centrifugation followed by ultrafiltration, extraction, or chromatography, or the like, are generally used.

It is desirable to concentrate an AcAmy1 or variant α-amylase polypeptide-containing solution in order to optimize recovery. Use of unconcentrated solutions requires increased incubation time in order to collect the purified enzyme precipitate.

The enzyme containing solution is concentrated using conventional concentration techniques until the desired enzyme level is obtained. Concentration of the enzyme containing solution may be achieved by any of the techniques discussed herein. Exemplary methods of purification include but are not limited to rotary vacuum filtration and/or ultrafiltration.

The enzyme solution is concentrated into a concentrated enzyme solution until the enzyme activity of the concentrated AcAmy1 or variant α-amylase polypeptide-containing solution is at a desired level.

Concentration may be performed using, e.g., a precipitation agent, such as a metal halide precipitation agent. Metal halide precipitation agents include but are not limited to alkali metal chlorides, alkali metal bromides and blends of two or more of these metal halides. Exemplary metal halides include sodium chloride, potassium chloride, sodium bromide, potassium bromide and blends of two or more of these metal halides. The metal halide precipitation agent, sodium chloride, can also be used as a preservative.

The metal halide precipitation agent is used in an amount effective to precipitate the AcAmy1 or variant thereof. The selection of at least an effective amount and an optimum amount of metal halide effective to cause precipitation of the enzyme, as well as the conditions of the precipitation for maximum recovery including incubation time, pH, temperature and concentration of enzyme, will be readily apparent to one of ordinary skill in the art, after routine testing.

Generally, at least about 5% w/v (weight/volume) to about 25% w/v of metal halide is added to the concentrated enzyme solution, and usually at least 8% w/v. Generally, no more than about 25% w/v of metal halide is added to the concentrated enzyme solution and usually no more than about 20% w/v. The optimal concentration of the metal halide precipitation agent will depend, among others, on the nature of the specific AcAmy1 or variant α-amylase polypeptide and on its concentration in the concentrated enzyme solution.

Another alternative way to precipitate the enzyme is to use organic compounds. Exemplary organic compound precipitating agents include: 4-hydroxybenzoic acid, alkali metal salts of 4-hydroxybenzoic acid, alkyl esters of 4-hydroxybenzoic acid, and blends of two or more of these organic compounds. The addition of said organic compound precipitation agents can take place prior to, simultaneously with or subsequent to the addition of the metal halide precipitation agent, and the addition of both precipitation agents, organic compound and metal halide, may be carried out sequentially or simultaneously.

Generally, the organic precipitation agents are selected from the group consisting of alkali metal salts of 4-hydroxybenzoic acid, such as sodium or potassium salts, and linear or branched alkyl esters of 4-hydroxybenzoic acid, wherein the alkyl group contains from 1 to 12 carbon atoms, and blends of two or more of these organic compounds. The organic compound precipitation agents can be, for example, linear or branched alkyl esters of 4-hydroxybenzoic acid, wherein the alkyl group contains from 1 to 10 carbon atoms, and blends of two or more of these organic compounds. Exemplary organic compounds are linear alkyl esters of 4-hydroxybenzoic acid, wherein the alkyl group contains from 1 to 6 carbon atoms, and blends of two or more of these organic compounds. Methyl esters of 4-hydroxybenzoic acid, propyl esters of 4-hydroxybenzoic acid, butyl ester of 4-hydroxybenzoic acid, ethyl ester of 4-hydroxybenzoic acid and blends of two or more of these organic compounds can also be used. Additional organic compounds also include but are not limited to 4-hydroxybenzoic acid methyl ester (named methyl PARABEN), 4-hydroxybenzoic acid propyl ester (named propyl PARABEN), which also are both amylase preservative agents. For further descriptions, see, e.g., U.S. Pat. No. 5,281,526.

Addition of the organic compound precipitation agent provides the advantage of high flexibility of the precipitation conditions with respect to pH, temperature, AcAmy1 or variant α-amylase polypeptide concentration, precipitation agent concentration, and time of incubation.

The organic compound precipitation agent is used in an amount effective to improve precipitation of the enzyme by means of the metal halide precipitation agent. The selection of at least an effective amount and an optimum amount of organic compound precipitation agent, as well as the conditions of the precipitation for maximum recovery including incubation time, pH, temperature and concentration of enzyme, will be readily apparent to one of ordinary skill in the art, in light of the present disclosure, after routine testing.

Generally, at least about 0.01% w/v of organic compound precipitation agent is added to the concentrated enzyme solution and usually at least about 0.02% w/v. Generally, no more than about 0.3% w/v of organic compound precipitation agent is added to the concentrated enzyme solution and usually no more than about 0.2% w/v.

The concentrated polypeptide solution, containing the metal halide precipitation agent, and the organic compound precipitation agent, can be adjusted to a pH, which will, of necessity, depend on the enzyme to be purified. Generally, the pH is adjusted at a level near the isoelectric point of the amylase. The pH can be adjusted at a pH in a range from about 2.5 pH units below the isoelectric point (pI) up to about 2.5 pH units above the isoelectric point.

The incubation time necessary to obtain a purified enzyme precipitate depends on the nature of the specific enzyme, the concentration of enzyme, and the specific precipitation agent(s) and its (their) concentration. Generally, the time effective to precipitate the enzyme is between about 1 to about 30 hours; usually it does not exceed about 25 hours. In the presence of the organic compound precipitation agent, the time of incubation can still be reduced to less about 10 hours and in most cases even about 6 hours.

Generally, the temperature during incubation is between about 4° C. and about 50° C. Usually, the method is carried out at a temperature between about 10° C. and about 45° C. (e.g., between about 20° C. and about 40° C.). The optimal temperature for inducing precipitation varies according to the solution conditions and the enzyme or precipitation agent(s) used.

The overall recovery of purified enzyme precipitate, and the efficiency with which the process is conducted, is improved by agitating the solution comprising the enzyme, the added metal halide and the added organic compound. The agitation step is done both during addition of the metal halide and the organic compound, and during the subsequent incubation period. Suitable agitation methods include mechanical stirring or shaking, vigorous aeration, or any similar technique.

After the incubation period, the purified enzyme is then separated from the dissociated pigment and other impurities and collected by conventional separation techniques, such as filtration, centrifugation, microfiltration, rotary vacuum filtration, ultrafiltration, press filtration, cross membrane microfiltration, cross flow membrane microfiltration, or the like. Further purification of the purified enzyme precipitate can be obtained by washing the precipitate with water. For example, the purified enzyme precipitate is washed with water containing the metal halide precipitation agent, or with water containing the metal halide and the organic compound precipitation agents.

During fermentation, an AcAmy1 or variant α-amylase polypeptide accumulates in the culture broth. For the isolation and purification of the desired AcAmy1 or variant α-amylase, the culture broth is centrifuged or filtered to eliminate cells, and the resulting cell-free liquid is used for enzyme purification. In one embodiment, the cell-free broth is subjected to salting out using ammonium sulfate at about 70% saturation; the 70% saturation-precipitation fraction is then dissolved in a buffer and applied to a column such as a Sephadex G-100 column, and eluted to recover the enzyme-active fraction. For further purification, a conventional procedure such as ion exchange chromatography may be used.

Purified enzymes are useful for laundry and cleaning applications. For example, they can be used in laundry detergents and spot removers. They can be made into a final product that is either liquid (solution, slurry) or solid (granular, powder).

A more specific example of purification, is described in Sumitani et al. (2000) "New type of starch-binding domain: the direct repeat motif in the C-terminal region of Bacillus sp. 195 α-amylase contributes to starch binding and raw starch degrading," Biochem. J. 350: 477-484, and is briefly summarized here. The enzyme obtained from 4 liters of a Streptomyces lividans TK24 culture supernatant was treated with $(NH_4)_2SO_4$ at 80% saturation. The precipitate was recovered by centrifugation at 10,000×g (20 min. and 4° C.) and re-dissolved in 20 mM Tris/HCl buffer (pH 7.0) containing 5 mM $CaCl_2$. The solubilized precipitate was then dialyzed against the same buffer. The dialyzed sample was then applied to a Sephacryl S-200 column, which had previously been equilibrated with 20 mM Tris/HCl buffer, (pH 7.0), 5 mM $CaCl_2$, and eluted at a linear flow rate of 7 mL/hr with the same buffer. Fractions from the column were collected and assessed for activity as judged by enzyme assay and SDS-PAGE. The protein was further purified as follows. A Toyopearl HW55 column (Tosoh Bioscience, Montgomeryville, Pa.; Cat. No. 19812) was equilibrated with 20 mM Tris/HCl buffer (pH 7.0) containing 5 mM $CaCl_2$ and 1.5 M $(NH_4)_2SO_4$. The enzyme was eluted with a linear gradient of 1.5 to 0 M $(NH_4)_2SO_4$ in 20 mM Tris/HCL buffer, pH 7.0 containing 5 mM $CaCl_2$. The active fractions were collected, and the enzyme precipitated with $(NH_4)_2SO_4$ at 80% saturation. The precipitate was recovered, re-dissolved, and dialyzed as described above. The dialyzed sample was then applied to a Mono Q HR5/5 column (Amersham Pharmacia; Cat. No. 17-5167-01) previously equilibrated with 20 mM Tris/HCl buffer (pH 7.0) containing 5 mM $CaCl_2$, at a flow rate of 60 mL/hour. The active fractions are collected and added to a 1.5 M $(NH_4)_2SO_4$ solution. The active enzyme fractions were re-chromatographed on a Toyopearl HW55 column, as before, to yield a homogeneous enzyme as determined by SDS-PAGE. See Sumitani et al. (2000) Biochem. J. 350: 477-484, for general discussion of the method and variations thereon.

For production scale recovery, an AcAmy1 or variant α-amylase polypeptide can be partially purified as generally described above by removing cells via flocculation with polymers. Alternatively, the enzyme can be purified by microfiltration followed by concentration by ultrafiltration using available membranes and equipment. However, for some applications, the enzyme does not need to be purified, and whole broth culture can be lysed and used without further treatment. The enzyme can then be processed, for example, into granules.

4. Compositions and Uses of AcAmy1 and Variants Thereof

AcAmy1 and its variants are useful for a variety of industrial applications. For example, AcAmy1 and its variants are useful in a starch conversion process, particularly in a saccharification process of a starch that has undergone liquefaction. The desired end-product may be any product that may be produced by the enzymatic conversion of the starch substrate. For example, the desired product may be a syrup rich in glucose and maltose, which can be used in other processes, such as the preparation of HFCS, or which can be converted into a number of other useful products, such as ascorbic acid intermediates (e.g., gluconate; 2-keto-L-gulonic acid; 5-ketogluconate; and 2,5-diketogluconate); 1,3-propanediol; aromatic amino acids (e.g., tyrosine, phenylalanine and tryptophan); organic acids (e.g., lactate, pyruvate, succinate, isocitrate, and oxaloacetate); amino acids (e.g., serine and glycine); antibiotics; antimicrobials; enzymes; vitamins; and hormones.

The starch conversion process may be a precursor to, or simultaneous with, a fermentation process designed to produce alcohol for fuel or drinking (i.e., potable alcohol). One skilled in the art is aware of various fermentation processes that may be used in the production of these end-products. AcAmy1 and variants thereof also are useful in compositions and methods of food preparation. These various uses of AcAmy1 and its variants are described in more detail below.

4.1. Preparation of Starch Substrates

Those of general skill in the art are well aware of available methods that may be used to prepare starch substrates for use in the processes disclosed herein. For example, a useful starch substrate may be obtained from tubers, roots, stems, legumes, cereals or whole grain. More specifically, the granular starch may be obtained from corn, cobs, wheat, barley, rye, triticale, milo, sago, millet, cassava, tapioca, sorghum, rice, peas, bean, banana, or potatoes. Corn contains about 60-68% starch; barley contains about 55-65% starch; millet contains about 75-80% starch; wheat contains about 60-65% starch; and polished rice contains 70-72% starch. Specifically contemplated starch substrates are corn starch and wheat starch. The starch from a grain may be ground or whole and includes corn solids, such as kernels, bran and/or cobs. The starch may be highly refined raw starch or feedstock from starch refinery processes. Various starches also are commercially available. For example, corn starch is available from Cerestar, Sigma, and Katayama Chemical Industry Co. (Japan); wheat starch is available from Sigma; sweet potato starch is available from Wako Pure Chemical Industry Co. (Japan); and potato starch is available from Nakaari Chemical Pharmaceutical Co. (Japan).

The starch substrate can be a crude starch from milled whole grain, which contains non-starch fractions, e.g., germ residues and fibers. Milling may comprise either wet milling or dry milling or grinding. In wet milling, whole grain is soaked in water or dilute acid to separate the grain into its component parts, e.g., starch, protein, germ, oil, kernel fibers. Wet milling efficiently separates the germ and meal (i.e., starch granules and protein) and is especially suitable for production of syrups. In dry milling or grinding, whole kernels are ground into a fine powder and often processed without fractionating the grain into its component parts. In some cases, oils from the kernels are recovered. Dry ground grain thus will comprise significant amounts of non-starch carbohydrate compounds, in addition to starch. Dry grinding of the starch substrate can be used for production of ethanol and other biochemicals. The starch to be processed may be a highly refined starch quality, for example, at least 90%, at least 95%, at least 97%, or at least 99.5% pure.

4.2. Gelatinization and Liquefaction of Starch

As used herein, the term "liquefaction" or "liquefy" means a process by which starch is converted to less viscous and shorter chain dextrins. Generally, this process involves gelatinization of starch simultaneously with or followed by the addition of an α-amylase, although additional liquefaction-inducing enzymes optionally may be added. In some embodiments, the starch substrate prepared as described above is slurried with water. The starch slurry may contain starch as a weight percent of dry solids of about 10-55%, about 20-45%, about 30-45%, about 30-40%, or about 30-35%. α-Amylase (EC 3.2.1.1) may be added to the slurry, with a metering pump, for example. The α-amylase typically used for this application is a thermally stable, bacterial α-amylase, such as a *Geobacillus stearothermophilus* α-amylase. The α-amylase is usually supplied, for example, at about 1500 units per kg dry matter of starch. To optimize α-amylase stability and activity, the pH of the slurry typically is adjusted to about pH 5.5-6.5 and about 1 mM of calcium (about 40 ppm free calcium ions) typically is added. *Geobacillus stearothermophilus* variants or other α-amylases may require different conditions. Bacterial α-amylase remaining in the slurry following liquefaction may be deactivated via a number of methods, including lowering the pH in a subsequent reaction step or by removing calcium from the slurry in cases where the enzyme is dependent upon calcium.

The slurry of starch plus the α-amylase may be pumped continuously through a jet cooker, which is steam heated to 105° C. Gelatinization occurs rapidly under these conditions, and the enzymatic activity, combined with the significant shear forces, begins the hydrolysis of the starch substrate. The residence time in the jet cooker is brief. The partly gelatinized starch may be passed into a series of holding tubes maintained at 105-110° C. and held for 5-8 mM to complete the gelatinization process ("primary liquefaction"). Hydrolysis to the required DE is completed in holding tanks at 85-95° C. or higher temperatures for about 1 to 2 hours ("secondary liquefaction"). These tanks may contain baffles to discourage back mixing. As used herein, the term "minutes of secondary liquefaction" refers to the time that has elapsed from the start of secondary liquefaction to the time that the Dextrose Equivalent (DE) is measured. The slurry is then allowed to cool to room temperature. This cooling step can be 30 minutes to 180 minutes, e.g. 90 minutes to 120 minutes.

The liquefied starch resulting from the process above typically contains about 98% oligosaccharides and about 2% maltose and 0.3% D-glucose. The liquefied starch typically is in the form of a slurry having a dry solids content (w/w) of about 10-50%; about 10-45%; about 15-40%; about 20-40%; about 25-40%; or about 25-35%.

AcAmy1 and variants thereof can be used in a process of liquefaction instead of bacterial α-amylases. Liquefaction with AcAmy1 and variants thereof advantageously can be conducted at low pH, eliminating the requirement to adjust the pH to about pH 5.5-6.5. AcAmy1 and variants thereof can be used for liquefaction at a pH range of 2 to 7, e.g., pH 3.0-7.5, pH 4.0-6.0, or pH 4.5-5.8. AcAmy1 and variants thereof can maintain liquefying activity at a temperature range of about 85° C.-95° C., e.g., 85° C., 90° C., or 95° C. For example, liquefaction can be conducted with 800 µg AcAmy1 or a variant thereof in a solution of 25% DS corn starch for 10 min at pH 5.8 and 85° C., or pH 4.5 and 95° C., for example. Liquefying activity can be assayed using any of a number of known viscosity assays in the art.

4.3. Saccharification

The liquefied starch can be saccharified into a syrup rich in lower DP (e.g., DP1+DP2) saccharides, using the AcAmy1 and variants thereof, optionally in the presence of another enzyme(s). The exact composition of the products of saccharification depends on the combination of enzymes used, as well as the type of granular starch processed. Advantageously, the syrup obtainable using the provided AcAmy1 and variants thereof may contain a weight percent of DP2 of the total oligosaccharides in the saccharified starch exceeding 30%, e.g., 45%-65% or 55%-65%. The weight percent of (DP1+DP2) in the saccharified starch may exceed about 70%, e.g., 75%-85% or 80%-85%. AcAmy1 or its variants also produce a relatively high yield of glucose, e.g., DP1>20%, in the syrup product.

Whereas liquefaction is generally run as a continuous process, saccharification is often conducted as a batch process. Saccharification typically is most effective at temperatures of about 60-65° C. and a pH of about 4.0-4.5, e.g., pH 4.3, necessitating cooling and adjusting the pH of the liquefied starch. Saccharification may be performed, for example, at a temperature between about 40° C., about 50° C., or about 55° C. to about 60° C. or about 65° C. Saccharification is normally conducted in stirred tanks, which may take several hours to fill or empty. Enzymes typically are added either at a fixed ratio to dried solids as the tanks are filled or added as a single dose at the commencement of the filling stage. A saccharification reaction to make a syrup typically is run over about 24-72 hours, for example, 24-48 hours. When a maximum or desired DE has been attained, the reaction is stopped by heating to 85° C. for 5 min, for example. Further incubation will result in a lower DE, eventually to about 90 DE, as accumulated glucose re-polymerizes to isomaltose and/or other reversion products via an enzymatic reversion reaction and/or with the approach of thermodynamic equilibrium. When using an AcAmy1 polypeptide or variants thereof, saccharification optimally is conducted at a temperature range of about 30° C. to about 75° C., e.g., 45° C.-75° C. or 47° C.-74° C. The saccharifying may be conducted over a pH range of about pH 3 to about pH 7, e.g., pH 3.0-pH 7.5, pH 3.5-pH 5.5, pH 3.5, pH 3.8, or pH 4.5.

AcAmy1 or a variant thereof also may be added to the slurry in the form of a composition. AcAmy1 or a variant thereof can be added to a slurry of a granular starch substrate in an amount of about 0.6-10 ppm ds, e.g., 2 ppm ds. The AcAmy1 or variant thereof can be added as a whole broth, clarified, partially purified, or purified enzyme. The specific activity of the purified AcAmy1 or variant thereof may be about 300 U/mg of enzyme, for example, measured with the PAHBAH assay. AcAmy1 or variant thereof also can be added as a whole broth product.

AcAmy1 or a variant thereof may be added to the slurry as an isolated enzyme solution. For example, AcAmy1 or a variant thereof can be added in the form of a cultured cell material produced by host cells expressing the AcAmy1 or variant thereof. AcAmy1 or a variant thereof also may be secreted by a host cell into the reaction medium during the fermentation or SSF process, such that the enzyme is provided continuously into the reaction. The host cell producing and secreting the AcAmy1 or a variant may also express an additional enzyme, such as a glucoamylase. For example, U.S. Pat. No. 5,422,267 discloses the use of a glucoamylase in yeast for production of alcoholic beverages. For example, a host cell, e.g., *Trichoderma reesei* or *Aspergillus niger*, may be engineered to co-express AcAmy1 or a variant thereof and a glucoamylase, e.g., HgGA, TrGA, or a TrGA variant, during saccharification. The host cell can be genetically modified so as not to express its endogenous glucoamylase and/or other enzymes, proteins or other materials. The host cell can be engineered to express a broad spectrum of various saccharolytic enzymes. For example, the recombinant yeast host cell can comprise nucleic acids encoding a glucoamylase, an alpha-glucosidase, an enzyme that utilizes pentose sugar, an α-amylase, a pullulanase, an isoamylase, and/or an isopullulanase. See, e.g., WO 2011/153516 A2.

4.4. Isomerization

The soluble starch hydrolysate produced by treatment with AcAmy1 or variants thereof can be converted into high fructose starch-based syrup (HFSS), such as high fructose corn syrup (HFCS). This conversion can be achieved using a glucose isomerase, particularly a glucose isomerase immobilized on a solid support. The pH is increased to about 6.0 to about 8.0, e.g., pH 7.5, and $Ca^{2+}$ is removed by ion exchange. Suitable isomerases include Sweetzyme®, IT (Novozymes A/S); G-zyme® IMGI, and G-zyme® G993, Ketomax®, G-zyme® G993, G-zyme® G993 liquid, and GenSweet® IGI. Following isomerization, the mixture typically contains about 40-45% fructose, e.g., 42% fructose.

4.5. Fermentation

The soluble starch hydrolysate, particularly a glucose rich syrup, can be fermented by contacting the starch hydrolysate with a fermenting organism typically at a temperature around 32° C., such as from 30° C. to 35° C. EOF products include metabolites, such as citric acid, lactic acid, succinic acid, monosodium glutamate, gluconic acid, sodium gluconate, calcium gluconate, potassium gluconate, itaconic acid and other carboxylic acids, glucono delta-lactone, sodium erythorbate, lysine and other amino acids, omega 3 fatty acid, butanol, isoprene, 1,3-propanediol and other biomaterials.

Ethanologenic microorganisms include yeast, such as *Saccharomyces cerevisiae* and bacteria, e.g., *Zymomonas moblis*, expressing alcohol dehydrogenase and pyruvate decarboxylase. The ethanologenic microorganism can express xylose reductase and xylitol dehydrogenase, which convert xylose to xylulose. Improved strains of ethanologenic microorganisms, which can withstand higher temperatures, for example, are known in the art and can be used. See Liu et al. (2011) *Sheng Wu Gong Cheng Xue Bao* 27(7): 1049-56. Commercial sources of yeast include ETHANOL RED® (LeSaffre); Thermosacc® (Lallemand); RED STAR® (Red Star); FERMIOL® (DSM Specialties); and SUPERSTART® (Alltech). Microorganisms that produce other metabolites, such as citric acid and lactic acid, by fermentation are also known in the art. See, e.g., Papagianni (2007) "Advances in citric acid fermentation by *Aspergillus niger*: biochemical aspects, membrane transport and modeling," *Biotechnol. Adv.* 25(3): 244-63; John et al. (2009) "Direct lactic acid fermentation: focus on simultaneous saccharification and lactic acid production," *Biotechnol. Adv.* 27(2): 145-52.

The saccharification and fermentation processes may be carried out as an SSF process. Fermentation may comprise subsequent purification and recovery of ethanol, for example. During the fermentation, the ethanol content of the broth or "beer" may reach about 8-18% v/v, e.g., 14-15% v/v. The broth may be distilled to produce enriched, e.g., 96% pure, solutions of ethanol. Further, $CO_2$ generated by fermentation may be collected with a $CO_2$ scrubber, compressed, and marketed for other uses, e.g., carbonating beverage or dry ice production. Solid waste from the fermentation process may be used as protein-rich products, e.g., livestock feed.

As mentioned above, an SSF process can be conducted with fungal cells that express and secrete AcAmy1 or its variants continuously throughout SSF. The fungal cells expressing AcAmy1 or its variants also can be the fermenting microorganism, e.g., an ethanologenic microorganism. Ethanol production thus can be carried out using a fungal cell that expresses sufficient AcAmy1 or its variants so that less or no enzyme has to be added exogenously. The fungal host cell can be from an appropriately engineered fungal strain. Fungal host cells that express and secrete other enzymes, in addition to AcAmy1 or its variants, also can be used. Such cells may express glucoamylase and/or a pullulanase, phytase, alpha-glucosidase, isoamylase, beta-amylase cellulase, xylanase, other hemicellulases, protease, beta-glucosidase, pectinase, esterase, redox enzymes, transferase, or other enzyme.

A variation on this process is a "fed-batch fermentation" system, where the substrate is added in increments as the fermentation progresses. Fed-batch systems are useful when catabolite repression may inhibit the metabolism of the cells and where it is desirable to have limited amounts of substrate in the medium. The actual substrate concentration in fed-batch systems is estimated by the changes of measurable factors such as pH, dissolved oxygen and the partial pressure of waste gases, such as $CO_2$. Batch and fed-batch fermentations are common and well known in the art.

Continuous fermentation is an open system where a defined fermentation medium is added continuously to a bioreactor, and an equal amount of conditioned medium is removed simultaneously for processing. Continuous fermentation generally maintains the cultures at a constant high density where cells are primarily in log phase growth. Continuous fermentation permits modulation of cell growth and/or product concentration. For example, a limiting nutrient such as the carbon source or nitrogen source is maintained at a fixed rate and all other parameters are allowed to moderate. Because growth is maintained at a steady state, cell loss due to medium being drawn off should be balanced against the cell growth rate in the fermentation. Methods of optimizing continuous fermentation processes and maximizing the rate of product formation are well known in the art of industrial microbiology.

4.6. Compositions Comprising AcAmy1 or Variants Thereof

AcAmy1 or variants thereof may be combined with a glucoamylase (EC 3.2.1.3), e.g., a *Trichoderma* glucoamylase or variant thereof. An exemplary glucoamylase is *Trichoderma reesei* glucoamylase (TrGA) and variants thereof that possess superior specific activity and thermal stability. See U.S. Published Applications Nos. 2006/0094080, 2007/0004018, and 2007/0015266 (Danisco US Inc.). Suitable variants of TrGA include those with glucoamylase activity and at least 80%, at least 90%, or at least 95% sequence identity to wild-type TrGA. AcAmy1 and its variants advantageously increase the yield of glucose produced in a saccharification process catalyzed by TrGA.

Alternatively, the glucoamylase may be another glucoamylase derived from plants, fungi, or bacteria. For example, the glucoamylases may be *Aspergillus niger* G1 or G2 glucoamylase or its variants (e.g., Boel et al. (1984) *EMBO J*. 3: 1097-1102; WO 92/00381; WO 00/04136 (Novo Nordisk A/S)); and *A. awamori* glucoamylase (e.g., WO 84/02921 (Cetus Corp.)). Other contemplated *Aspergillus* glucoamylase include variants with enhanced thermal stability, e.g., G137A and G139A (Chen et al. (1996) *Prot. Eng.* 9: 499-505); D257E and D293E/Q (Chen et al. (1995) *Prot. Eng.* 8: 575-582); N182 (Chen et al. (1994) *Biochem. J*. 301: 275-281); A246C (Fierobe et al. (1996) *Biochemistry*, 35: 8698-8704); and variants with Pro residues in positions A435 and S436 (Li et al. (1997) *Protein Eng.* 10: 1199-1204). Other contemplated glucoamylases include *Talaromyces* glucoamylases, in particular derived from *T. emersonii* (e.g., WO 99/28448 (Novo Nordisk A/S), *T. leycettanus* (e.g., U.S. Pat. No. RE 32,153 (CPC International, Inc.)), *T. duponti*, or *T. thermophiles* (e.g., U.S. Pat. No. 4,587,215). Contemplated bacterial glucoamylases include glucoamylases from the genus *Clostridium*, in particular *C. thermoamylolyticum* (e.g., EP 135,138 (CPC International, Inc.) and *C. thermohydrosulfuricum* (e.g., WO 86/01831 (Michigan Biotechnology Institute)). Suitable glucoamylases include the glucoamylases derived from *Aspergillus oryzae*, such as a glucoamylase shown in SEQ ID NO:2 in WO 00/04136 (Novo Nordisk A/S). Also suitable are commercial glucoamylases, such as AMG 200L; AMG 300 L; SAN™ SUPER and AMG™ E (Novozymes); OPTIDEX® 300 and OPTIDEX L-400 (Danisco US Inc.); AMIGASE™ and AMIGASE™ PLUS (DSM); G-ZYME® G900 (Enzyme Bio-Systems); and G-ZYME® G990 ZR (*A. niger* glucoamylase with a low protease content). Still other suitable glucoamylases include *Aspergillus fumigatus* glucoamylase, *Talaromyces* glucoamylase, *Thielavia* glucoamylase, *Trametes* glucoamylase, *Thermomyces* glucoamylase, *Athelia* glucoamylase, or *Humicola* glucoamylase (e.g., HgGA). Glucoamylases typically are added in an amount of about 0.1-2 glucoamylase units (GAU)/g ds, e.g., about 0.16 GAU/g ds, 0.23 GAU/g ds, or 0.33 GAU/g ds.

Other suitable enzymes that can be used with AcAmy1 or its variants include a phytase, protease, pullulanase, β-amylase, isoamylase, α-amylase that is not AcAmy1, alpha-glucosidase, cellulase, xylanase, other hemicellulases, beta-glucosidase, transferase, pectinase, lipase, cutinase, esterase, redox enzymes, or a combination thereof. For example, a debranching enzyme, such as an isoamylase (EC 3.2.1.68), may be added in effective amounts well known to the person skilled in the art. A pullulanase (EC 3.2.1.41), e.g., Promozyme®, is also suitable. Pullulanase typically is added at 100 U/kg ds. Further suitable enzymes include proteases, such as fungal and bacterial proteases. Fungal proteases include those obtained from *Aspergillus*, such as *A. niger*, *A. awamori*, *A. oryzae*; *Mucor* (e.g., *M. miehei*); *Rhizopus*; and *Trichoderma*.

β-Amylases (EC 3.2.1.2) are exo-acting maltogenic amylases, which catalyze the hydrolysis of 1,4-α-glucosidic linkages into amylopectin and related glucose polymers, thereby releasing maltose. β-Amylases have been isolated from various plants and microorganisms. See Fogarty et al. (1979) in PROGRESS IN INDUSTRIAL MICROBIOLOGY, Vol. 15, pp. 112-115. These β-Amylases have optimum temperatures in the range from 40° C. to 65° C. and optimum pH in the range from about 4.5 to about 7.0. Contemplated β-amylases include, but are not limited to, β-amylases from barley Spezyme® BBA 1500, Spezyme® DBA, Optimalt™ ME, Optimalt™ BBA (Danisco US Inc.); and Novozym™ WBA (Novozymes A/S).

5. Compositions and Methods for Baking and Food Preparation

The present invention also relates to a "food composition," including but not limited to a food product, animal feed and/or food/feed additives, comprising an AcAmy1 or variant thereof, and methods for preparing such a food composition comprising mixing AcAmy1 or variant thereof with one or more food ingredients, or uses thereof.

Furthermore, the present invention relates to the use of an AcAmy1 or variant thereof in the preparation of a food composition, wherein the food composition is baked subsequent to the addition of the polypeptide of the invention. As used herein the term "baking composition" means any composition and/or additive prepared in the process of providing a baked food product, including but not limited to bakers flour, a dough, a baking additive and/or a baked product. The food composition or additive may be liquid or solid.

As used herein, the term "flour" means milled or ground cereal grain. The term "flour" also may mean Sago or tuber products that have been ground or mashed. In some embodiments, flour may also contain components in addition to the milled or mashed cereal or plant matter. An example of an additional component, although not intended to be limiting, is a leavening agent. Cereal grains include wheat, oat, rye, and barley. Tuber products include tapioca flour, cassava flour, and custard powder. The term "flour" also includes ground corn flour, maize-meal, rice flour, whole-meal flour, self-rising flour, tapioca flour, cassava flour, ground rice, enriched flower, and custard powder.

For the commercial and home use of flour for baking and food production, it is important to maintain an appropriate level of α-amylase activity in the flour. A level of activity that is too high may result in a product that is sticky and/or doughy and therefore unmarketable. Flour with insufficient α-amylase activity may not contain enough sugar for proper yeast function, resulting in dry, crumbly bread, or baked products. Accordingly, an AcAmy1 or variant thereof, by itself or in combination with another α-amylase(s), may be added to the flour to augment the level of endogenous α-amylase activity in flour.

An AcAmy1 or variant thereof further can be added alone or in a combination with other amylases to prevent or retard staling, i.e., crumb firming of baked products. The amount of anti-staling amylase will typically be in the range of 0.01-10 mg of enzyme protein per kg of flour, e.g., 0.5 mg/kg ds. Additional anti-staling amylases that can be used in combination with an AcAmy1 or variant thereof include an endo-amylase, e.g., a bacterial endo-amylase from Bacillus. The additional amylase can be another maltogenic α-amylase (EC 3.2.1.133), e.g., from Bacillus. Novamyl® is an exemplary maltogenic α-amylase from B. stearothermophilus strain NCIB 11837 and is described in Christophersen et al. (1997) Starch 50: 39-45. Other examples of anti-staling endo-amylases include bacterial α-amylases derived from Bacillus, such as B. licheniformis or B. amyloliquefaciens. The anti-staling amylase may be an exo-amylase, such as β-amylase, e.g., from plant sources, such as soy bean, or from microbial sources, such as Bacillus.

The baking composition comprising an AcAmy1 or variant thereof further can comprise a phospholipase or enzyme with phospholipase activity. An enzyme with phospholipase activity has an activity that can be measured in Lipase Units (LU). The phospholipase may have $A_1$ or $A_2$ activity to remove fatty acid from the phospholipids, forming a lysophospholipid. It may or may not have lipase activity, i.e., activity on triglyceride substrates. The phospholipase typically has a temperature optimum in the range of 30-90° C., e.g., 30-70° C. The added phospholipases can be of animal origin, for example, from pancreas, e.g., bovine or porcine pancreas, snake venom or bee venom. Alternatively, the phospholipase may be of microbial origin, e.g., from filamentous fungi, yeast or bacteria, for example.

The phospholipase is added in an amount that improves the softness of the bread during the initial period after baking, particularly the first 24 hours. The amount of phospholipase will typically be in the range of 0.01-10 mg of enzyme protein per kg of flour, e.g., 0.1-5 mg/kg. That is, phospholipase activity generally will be in the range of 20-1000 LU/kg of flour, where a Lipase Unit is defined as the amount of enzyme required to release 1 µmol butyric acid per minute at 30° C., pH 7.0, with gum arabic as emulsifier and tributyrin as substrate.

Compositions of dough generally comprise wheat meal or wheat flour and/or other types of meal, flour or starch such as corn flour, cornstarch, rye meal, rye flour, oat flour, oatmeal, soy flour, sorghum meal, sorghum flour, potato meal, potato flour or potato starch. The dough may be fresh, frozen or par-baked. The dough can be a leavened dough or a dough to be subjected to leavening. The dough may be leavened in various ways, such as by adding chemical leavening agents, e.g., sodium bicarbonate or by adding a leaven, i.e., fermenting dough. Dough also may be leavened by adding a suitable yeast culture, such as a culture of Saccharomyces cerevisiae (baker's yeast), e.g., a commercially available strain of S. cerevisiae.

The dough may also comprise other conventional dough ingredients, e.g., proteins, such as milk powder, gluten, and soy; eggs (e.g., whole eggs, egg yolks or egg whites); an oxidant, such as ascorbic acid, potassium bromate, potassium iodate, azodicarbonamide (ADA) or ammonium persulfate; an amino acid such as L-cysteine; a sugar; or a salt, such as sodium chloride, calcium acetate, sodium sulfate or calcium sulfate. The dough further may comprise fat, e.g., triglyceride, such as granulated fat or shortening. The dough further may comprise an emulsifier such as mono- or diglycerides, diacetyl tartaric acid esters of mono- or diglycerides, sugar esters of fatty acids, polyglycerol esters of fatty acids, lactic acid esters of monoglycerides, acetic acid esters of monoglycerides, polyoxyethylene stearates, or lysolecithin. In particular, the dough can be made without addition of emulsifiers.

The dough product may be any processed dough product, including fried, deep fried, roasted, baked, steamed and boiled doughs, such as steamed bread and rice cakes. In one embodiment, the food product is a bakery product. Typical bakery (baked) products include bread—such as loaves, rolls, buns, bagels, pizza bases etc. pastry, pretzels, tortillas, cakes, cookies, biscuits, crackers etc.

Optionally, an additional enzyme may be used together with the anti-staling amylase and the phospholipase. The additional enzyme may be a second amylase, such as an amyloglucosidase, β-amylase, a cyclodextrin glucanotransferase, or the additional enzyme may be a peptidase, in particular an exopeptidase, a transglutaminase, a lipase, a cellulase, a xylanase, a protease, a protein disulfide isomerase, e.g., a protein disulfide isomerase as disclosed in WO 95/00636, for example, a glycosyltransferase, a branching enzyme (1,4-α-glucan branching enzyme), a 4-α-glucanotransferase (dextrin glycosyltransferase) or an oxidoreductase, e.g., a peroxidase, a laccase, a glucose oxidase, a pyranose oxidase, a lipooxygenase, an L-amino acid oxidase or a carbohydrate oxidase. The additional enzyme(s) may be of any origin, including mammalian and plant, and particularly of microbial (bacterial, yeast or fungal) origin and may be obtained by techniques conventionally used in the art.

The xylanase is typically of microbial origin, e.g., derived from a bacterium or fungus, such as a strain of Aspergillus. Xylanases include Pentopan® and Novozym 384®, for example, which are commercially available xylanase preparations produced from Trichoderma reesei. The amyloglucosidase may be an A. niger amyloglucosidase (such as AMG®). Other useful amylase products include Grindamyl® A 1000 or A 5000 (Grindsted Products, Denmark) and Amylase® H or Amylase® P (DSM). The glucose oxidase may be a fungal glucose oxidase, in particular an *Aspergillus niger* glucose oxidase (such as Gluzyme®). An exemplary protease is Neutrase®.

The process may be used for any kind of baked product prepared from dough, either of a soft or a crisp character, either of a white, light or dark type. Examples are bread, particularly white, whole-meal or rye bread, typically in the form of loaves or rolls, such as, but not limited to, French baguette-type bread, pita bread, tortillas, cakes, pancakes, biscuits, cookies, pie crusts, crisp bread, steamed bread, pizza and the like.

The AcAmy1 or variant thereof may be used in a pre-mix, comprising flour together with an anti-staling amylase, a phospholipase, and/or a phospholipid. The pre-mix may contain other dough-improving and/or bread-improving additives, e.g., any of the additives, including enzymes, mentioned above. The AcAmy1 or variant thereof can be a component of an enzyme preparation comprising an anti-staling amylase and a phospholipase, for use as a baking additive.

The enzyme preparation is optionally in the form of a granulate or agglomerated powder. The preparation can have a narrow particle size distribution with more than 95% (by weight) of the particles in the range from 25 to 500 μm. Granulates and agglomerated powders may be prepared by conventional methods, e.g., by spraying the AcAmy1 or variant thereof onto a carrier in a fluid-bed granulator. The carrier may consist of particulate cores having a suitable particle size. The carrier may be soluble or insoluble, e.g., a salt (such as NaCl or sodium sulfate), a sugar (such as sucrose or lactose), a sugar alcohol (such as sorbitol), starch, rice, corn grits, or soy.

Enveloped particles, i.e., α-amylase particles, can comprise an AcAmy1 or variants thereof. To prepare enveloped α-amylase particles, the enzyme is contacted with a food grade lipid in sufficient quantity to suspend all of the α-amylase particles. Food grade lipids, as used herein, may be any naturally organic compound that is insoluble in water but is soluble in non-polar organic solvents such as hydrocarbon or diethyl ether. Suitable food grade lipids include, but are not limited to, triglycerides either in the form of fats or oils that are either saturated or unsaturated. Examples of fatty acids and combinations thereof which make up the saturated triglycerides include, but are not limited to, butyric (derived from milk fat), palmitic (derived from animal and plant fat), and/or stearic (derived from animal and plant fat). Examples of fatty acids and combinations thereof which make up the unsaturated triglycerides include, but are not limited to, palmitoleic (derived from animal and plant fat), oleic (derived from animal and plant fat), linoleic (derived from plant oils), and/or linolenic (derived from linseed oil). Other suitable food grade lipids include, but are not limited to, monoglycerides and diglycerides derived from the triglycerides discussed above, phospholipids and glycolipids.

The food grade lipid, particularly in the liquid form, is contacted with a powdered form of the α-amylase particles in such a fashion that the lipid material covers at least a portion of the surface of at least a majority, e.g., 100% of the α-amylase particles. Thus, each α-amylase particle is individually enveloped in a lipid. For example, all or substantially all of the α-amylase particles are provided with a thin, continuous, enveloping film of lipid. This can be accomplished by first pouring a quantity of lipid into a container, and then slurrying the α-amylase particles so that the lipid thoroughly wets the surface of each α-amylase particle. After a short period of stirring, the enveloped α-amylase particles, carrying a substantial amount of the lipids on their surfaces, are recovered.

The thickness of the coating so applied to the particles of α-amylase can be controlled by selection of the type of lipid used and by repeating the operation in order to build up a thicker film, when desired.

The storing, handling and incorporation of the loaded delivery vehicle can be accomplished by means of a packaged mix. The packaged mix can comprise the enveloped α-amylase. However, the packaged mix may further contain additional ingredients as required by the manufacturer or baker. After the enveloped α-amylase has been incorporated into the dough, the baker continues through the normal production process for that product.

The advantages of enveloping the α-amylase particles are two-fold. First, the food grade lipid protects the enzyme from thermal denaturation during the baking process for those enzymes that are heat labile. Consequently, while the α-amylase is stabilized and protected during the proving and baking stages, it is released from the protective coating in the final baked good product, where it hydrolyzes the glucosidic linkages in polyglucans. The loaded delivery vehicle also provides a sustained release of the active enzyme into the baked good. That is, following the baking process, active α-amylase is continually released from the protective coating at a rate that counteracts, and therefore reduces the rate of, staling mechanisms.

In general, the amount of lipid applied to the α-amylase particles can vary from a few percent of the total weight of the α-amylase to many times that weight, depending upon the nature of the lipid, the manner in which it is applied to the α-amylase particles, the composition of the dough mixture to be treated, and the severity of the dough-mixing operation involved.

The loaded delivery vehicle, i.e., the lipid-enveloped enzyme, is added to the ingredients used to prepare a baked good in an effective amount to extend the shelf-life of the baked good. The baker computes the amount of enveloped α-amylase, prepared as discussed above, that will be required to achieve the desired anti-staling effect. The amount of the enveloped α-amylase required is calculated based on the concentration of enzyme enveloped and on the proportion of α-amylase to flour specified. A wide range of concentrations has been found to be effective, although, as has been discussed, observable improvements in anti-staling do not correspond linearly with the α-amylase concentration, but above certain minimal levels, large increases in α-amylase concentration produce little additional improvement. The α-amylase concentration actually used in a particular bakery production could be much higher than the minimum necessary to provide the baker with some insurance against inadvertent under-measurement errors by the baker. The lower limit of enzyme concentration is determined by the minimum anti-staling effect the baker wishes to achieve.

A method of preparing a baked good may comprise: a) preparing lipid-coated α-amylase particles, where substantially all of the α-amylase particles are coated; b) mixing a dough containing flour; c) adding the lipid-coated α-amylase to the dough before the mixing is complete and terminating the mixing before the lipid coating is removed from the α-amylase; d) proofing the dough; and e) baking the dough to provide the baked good, where the α-amylase is inactive during the mixing, proofing and baking stages and is active in the baked good.

The enveloped α-amylase can be added to the dough during the mix cycle, e.g., near the end of the mix cycle. The enveloped α-amylase is added at a point in the mixing stage that allows sufficient distribution of the enveloped α-amylase throughout the dough; however, the mixing stage is terminated before the protective coating becomes stripped from the α-amylase particle(s). Depending on the type and volume of dough, and mixer action and speed, anywhere from one to six minutes or more might be required to mix the enveloped α-amylase into the dough, but two to four minutes is average. Thus, several variables may determine the precise procedure. First, the quantity of enveloped α-amylase should have a total volume sufficient to allow the enveloped α-amylase to be spread throughout the dough mix. If the preparation of enveloped α-amylase is highly concentrated, additional oil may need to be added to the pre-mix before the enveloped α-amylase is added to the dough. Recipes and production processes may require specific modifications; however, good results generally can be achieved when 25% of the oil specified in a bread dough formula is held out of the dough and is used as a carrier for a concentrated enveloped α-amylase when added near the end of the mix cycle. In bread or other baked goods, particularly those having a low fat content, e.g., French-style breads, an enveloped α-amylase mixture of approximately 1% of the dry flour weight is sufficient to admix the enveloped α-amylase properly with the dough. The range of suitable percentages is wide and depends on the formula, finished product, and production methodology requirements of the individual baker. Second, the enveloped α-amylase suspension should be added to the mix with sufficient time for complete mixture into the dough, but not for such a time that excessive mechanical action strips the protective lipid coating from the enveloped α-amylase particles.

In a further aspect of the invention, the food composition is an oil, meat, lard, composition comprising an AcAmy1 or a variant thereof. In this context the term "[oil/meat/lard] composition" means any composition, based on, made from and/or containing oil, meat or lard, respectively. Another aspect the invention relates to a method of preparing an oil or meat or lard composition and/or additive comprising an AcAmy1 or a variant thereof, comprising mixing the polypeptide of the invention with a oil/meat/lard composition and/or additive ingredients.

In a further aspect of the invention, the food composition is an animal feed composition, animal feed additive and/or pet food comprising an AcAmy1 and variants thereof. The present invention further relates to a method for preparing such an animal feed composition, animal feed additive composition and/or pet food comprising mixing an AcAmy1 and variants thereof with one or more animal feed ingredients and/or animal feed additive ingredients and/or pet food ingredients. Furthermore, the present invention relates to the use of an AcAmy1 and variants thereof in the preparation of an animal feed composition and/or animal feed additive composition and/or pet food.

The term "animal" includes all non-ruminant and ruminant animals. In a particular embodiment, the animal is a non-ruminant animal, such as a horse and a mono-gastric animal. Examples of mono-gastric animals include, but are not limited to, pigs and swine, such as piglets, growing pigs, sows; poultry such as turkeys, ducks, chicken, broiler chicks, layers; fish such as salmon, trout, tilapia, catfish and carps; and crustaceans such as shrimps and prawns. In a further embodiment the animal is a ruminant animal including, but not limited to, cattle, young calves, goats, sheep, giraffes, bison, moose, elk, yaks, water buffalo, deer, camels, alpacas, llamas, antelope, pronghorn and nilgai.

In the present context, it is intended that the term "pet food" is understood to mean a food for a household animal such as, but not limited to dogs, cats, gerbils, hamsters, chinchillas, fancy rats, guinea pigs; avian pets, such as canaries, parakeets, and parrots; reptile pets, such as turtles, lizards and snakes; and aquatic pets, such as tropical fish and frogs.

The terms "animal feed composition," "feedstuff" and "fodder" are used interchangeably and may comprise one or more feed materials selected from the group comprising a) cereals, such as small grains (e.g., wheat, barley, rye, oats and combinations thereof) and/or large grains such as maize or sorghum; b) by products from cereals, such as corn gluten meal, Distillers Dried Grain Solubles (DDGS) (particularly corn based Distillers Dried Grain Solubles (cDDGS), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; e) minerals and vitamins.

6. Textile Desizing Compositions and Use

Also contemplated are compositions and methods of treating fabrics (e.g., to desize a textile) using an AcAmy1 or a variant thereof. Fabric-treating methods are well known in the art (see, e.g., U.S. Pat. No. 6,077,316). For example, the feel and appearance of a fabric can be improved by a method comprising contacting the fabric with an AcAmy1 or a variant thereof in a solution. The fabric can be treated with the solution under pressure.

An AcAmy1 or a variant thereof can be applied during or after the weaving of a textile, or during the desizing stage, or one or more additional fabric processing steps. During the weaving of textiles, the threads are exposed to considerable mechanical strain. Prior to weaving on mechanical looms, warp yarns are often coated with sizing starch or starch derivatives to increase their tensile strength and to prevent breaking. An AcAmy1 or a variant thereof can be applied during or after the weaving to remove these sizing starch or starch derivatives. After weaving, an AcAmy1 or a variant thereof can be used to remove the size coating before further processing the fabric to ensure a homogeneous and washproof result.

An AcAmy1 or a variant thereof can be used alone or with other desizing chemical reagents and/or desizing enzymes to desize fabrics, including cotton-containing fabrics, as detergent additives, e.g., in aqueous compositions. An AcAmy1 or a variant thereof also can be used in compositions and methods for producing a stonewashed look on indigo-dyed denim fabric and garments. For the manufacture of clothes, the fabric can be cut and sewn into clothes or garments, which are afterwards finished. In particular, for the manufacture of denim jeans, different enzymatic finishing methods have been developed. The finishing of denim garment normally is initiated with an enzymatic desizing step, during which garments are subjected to the action of amylolytic enzymes to provide softness to the fabric and make the cotton more accessible to the subsequent enzymatic finishing steps. An AcAmy1 or a variant thereof can be used in methods of finishing denim garments (e.g., a "bio-stoning process"), enzymatic desizing and providing softness to fabrics, and/or finishing process.

7. Cleaning Compositions

An aspect of the present compositions and methods is a cleaning composition that includes an AcAmy1 or variant thereof as a component. An amylase polypeptide can be used as a component in detergent compositions for hand washing, laundry washing, dishwashing, and other hard-surface cleaning.

7.1. Overview

Preferably, the AcAmy1 or variant thereof is incorporated into detergents at or near a concentration conventionally used for amylase in detergents. For example, an amylase polypeptide may be added in amount corresponding to 0.00001-1 mg (calculated as pure enzyme protein) of amylase per liter of wash/dishwash liquor. Exemplary formulations are provided herein, as exemplified by the following:

An amylase polypeptide may be a component of a detergent composition, as the only enzyme or with other enzymes including other amylolytic enzymes. As such, it may be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1,000 to 20,000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in, for example, GB 1483591. Liquid enzyme preparations may, for instance, be stabilized by adding a polyol such as propylene glycol, a sugar or sugar alcohol, lactic acid or boric acid according to established methods. Other enzyme stabilizers are known in the art. Protected enzymes may be prepared according to the method disclosed in for example EP 238 216. Polyols have long been recognized as stabilizers of proteins, as well as improving protein solubility.

The detergent composition may be in any useful form, e.g., as powders, granules, pastes, or liquid. A liquid detergent may be aqueous, typically containing up to about 70% of water and 0% to about 30% of organic solvent. It may also be in the form of a compact gel type containing only about 30% water.

The detergent composition comprises one or more surfactants, each of which may be anionic, nonionic, cationic, or zwitterionic. The detergent will usually contain 0% to about 50% of anionic surfactant, such as linear alkylbenzenesulfonate (LAS); α-olefinsulfonate (AOS); alkyl sulfate (fatty alcohol sulfate) (AS); alcohol ethoxysulfate (AEOS or AES); secondary alkanesulfonates (SAS); α-sulfo fatty acid methyl esters; alkyl- or alkenylsuccinic acid; or soap. The composition may also contain 0% to about 40% of nonionic surfactant such as alcohol ethoxylate (AEO or AE), carboxylated alcohol ethoxylates, nonylphenol ethoxylate, alkylpolyglycoside, alkyldimethylaminoxide, ethoxylated fatty acid monoethanolamide, fatty acid monoethanolamide, or polyhydroxy alkyl fatty acid amide (as described for example in WO 92/06154).

The detergent composition may additionally comprise one or more other enzymes, such as proteases, another amylolytic enzyme, cutinase, lipase, cellulase, pectate lyase, perhydrolase, xylanase, peroxidase, and/or laccase in any combination.

The detergent may contain about 1% to about 65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g., SKS-6 from Hoechst). The detergent may also be unbuilt, i.e. essentially free of detergent builder. The enzymes can be used in any composition compatible with the stability of the enzyme. Enzymes generally can be protected against deleterious components by known forms of encapsulation, for example, by granulation or sequestration in hydro gels. Enzymes, and specifically amylases, either with or without starch binding domains, can be used in a variety of compositions including laundry and dishwashing applications, surface cleaners, as well as in compositions for ethanol production from starch or biomass.

The detergent may comprise one or more polymers. Examples include carboxymethylcellulose (CMC), poly(vinylpyrrolidone) (PVP), polyethyleneglycol (PEG), poly(vinyl alcohol) (PVA), polycarboxylates such as polyacrylates, maleic/acrylic acid copolymers and lauryl methacrylate/acrylic acid copolymers.

The detergent may contain a bleaching system, which may comprise a $H_2O_2$ source such as perborate or percarbonate, which may be combined with a peracid-forming bleach activator such as tetraacetylethylenediamine (TAED) or nonanoyloxybenzenesulfonate (NOBS). Alternatively, the bleaching system may comprise peroxyacids (e.g., the amide, imide, or sulfone type peroxyacids). The bleaching system can also be an enzymatic bleaching system, for example, perhydrolase, such as that described in International PCT Application WO 2005/056783.

The enzymes of the detergent composition may be stabilized using conventional stabilizing agents, e.g., a polyol such as propylene glycol or glycerol; a sugar or sugar alcohol; lactic acid; boric acid or a boric acid derivative such as, e.g., an aromatic borate ester; and the composition may be formulated as described in, e.g., WO 92/19709 and WO 92/19708.

The detergent may also contain other conventional detergent ingredients such as e.g., fabric conditioners including clays, foam boosters, suds suppressors, anti-corrosion agents, soil-suspending agents, anti-soil redeposition agents, dyes, bactericides, tarnish inhibiters, optical brighteners, or perfumes.

The pH (measured in aqueous solution at use concentration) is usually neutral or alkaline, e.g., pH about 7.0 to about 11.0.

Particular forms of detergent compositions for inclusion of the present α-amylase are described, below.

7.2. Heavy Duty Liquid (HDL) Laundry Detergent Composition

Exemplary HDL laundry detergent compositions includes a detersive surfactant (10%-40% wt/wt), including an anionic detersive surfactant (selected from a group of linear or branched or random chain, substituted or unsubstituted alkyl sulphates, alkyl sulphonates, alkyl alkoxylated sulphate, alkyl phosphates, alkyl phosphonates, alkyl carboxylates, and/or mixtures thereof), and optionally non-ionic surfactant (selected from a group of linear or branched or random chain, substituted or unsubstituted alkyl alkoxylated alcohol, for example a $C_8$-$C_{18}$ alkyl ethoxylated alcohol and/or $C_6$-$C_{12}$ alkyl phenol alkoxylates), wherein the weight ratio of anionic detersive surfactant (with a hydrophilic index (HIc) of from 6.0 to 9) to non-ionic detersive surfactant is greater than 1:1. Suitable detersive surfactants also include cationic detersive surfactants (selected from a group of alkyl pyridinium compounds, alkyl quarternary ammonium compounds, alkyl quarternary phosphonium compounds, alkyl ternary sulphonium compounds, and/or mixtures thereof); zwitterionic and/or amphoteric detersive surfactants (selected from a group of alkanolamine sulpho-betaines); ampholytic surfactants; semi-polar non-ionic surfactants and mixtures thereof.

The composition may optionally include, a surfactancy boosting polymer consisting of amphiphilic alkoxylated grease cleaning polymers (selected from a group of alkoxylated polymers having branched hydrophilic and hydrophobic properties, such as alkoxylated polyalkylenimines in the range of 0.05 wt %-10 wt %) and/or random graft polymers (typically comprising of hydrophilic backbone comprising monomers selected from the group consisting of: unsaturated $C_1$-$C_6$ carboxylic acids, ethers, alcohols, aldehydes, ketones, esters, sugar units, alkoxy units, maleic anhydride, saturated polyalcohols such as glycerol, and mixtures thereof; and hydrophobic side chain(s) selected from the group consisting of: $C_4$-$C_{25}$ alkyl group, polypropylene, polybutylene, vinyl ester of a saturated $C_1$-$C_6$ mono-carboxylic acid, $C_1$-$C_6$ alkyl ester of acrylic or methacrylic acid, and mixtures thereof.

The composition may include additional polymers such as soil release polymers (include anionically end-capped polyesters, for example SRP1, polymers comprising at least one monomer unit selected from saccharide, dicarboxylic acid, polyol and combinations thereof, in random or block configuration, ethylene terephthalate-based polymers and co-polymers thereof in random or block configuration, for example Repel-o-tex SF, SF-2 and SRP6, Texcare SRA100, SRA300, SRN100, SRN170, SRN240, SRN300 and SRN325, Marloquest SL), anti-redeposition polymers (0.1 wt % to 10 wt %, include carboxylate polymers, such as polymers comprising at least one monomer selected from acrylic acid, maleic acid (or maleic anhydride), fumaric acid, itaconic acid, aconitic acid, mesaconic acid, citraconic acid, methylenemalonic acid, and any mixture thereof, vinylpyrrolidone homopolymer, and/or polyethylene glycol, molecular weight in the range of from 500 to 100,000 Da); cellulosic polymer (including those selected from alkyl cellulose, alkyl alkoxyalkyl cellulose, carboxyalkyl cellulose, alkyl carboxyalkyl cellulose examples of which include carboxymethyl cellulose, methyl cellulose, methyl hydroxyethyl cellulose, methyl carboxymethyl cellulose, and mixtures thereof) and polymeric carboxylate (such as maleate/acrylate random copolymer or polyacrylate homopolymer).

The composition may further include saturated or unsaturated fatty acid, preferably saturated or unsaturated $C_{12}$-$C_{24}$ fatty acid (0 wt % to 10 wt %); deposition aids (examples for which include polysaccharides, preferably cellulosic polymers, poly diallyl dimethyl ammonium halides (DADMAC), and co-polymers of DAD MAC with vinyl pyrrolidone, acrylamides, imidazoles, imidazolinium halides, and mixtures thereof, in random or block configuration, cationic guar gum, cationic cellulose such as cationic hydoxyethyl cellulose, cationic starch, cationic polyacylamides, and mixtures thereof.

The composition may further include dye transfer inhibiting agents, examples of which include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof; chelating agents, examples of which include ethylene-diamine-tetraacetic acid (EDTA), diethylene triamine penta methylene phosphonic acid (DTPMP), hydroxy-ethane diphosphonic acid (HEDP), ethylenediamine N,N'-disuccinic acid (EDDS), methyl glycine diacetic acid (MGDA), diethylene triamine penta acetic acid (DTPA), propylene diamine tetracetic acid (PDT A), 2-hydroxypyridine-N-oxide (HPNO), or methyl glycine diacetic acid (MGDA), glutamic acid N,N-diacetic acid (N,N-dicarboxymethyl glutamic acid tetrasodium salt (GLDA), nitrilotriacetic acid (NTA), 4,5-dihydroxy-m-benzenedisulfonic acid, citric acid and any salts thereof, N-hydroxyethylethylenediaminetri-acetic acid (HEDTA), triethylenetetraaminehexaacetic acid (TTHA), N-hydroxyethyliminodiacetic acid (HEIDA), dihydroxyethylglycine (DHEG), ethylenediaminetetrapropionic acid (EDTP), and derivatives thereof.

The composition preferably included enzymes (generally about 0.01 wt % active enzyme to 0.03 wt % active enzyme) selected from proteases, amylases, lipases, cellulases, choline oxidases, peroxidases/oxidases, pectate lyases, mannanases, cutinases, laccases, phospholipases, lysophospholipases, acyltransferases, perhydrolases, arylesterases, and any mixture thereof. The composition may include an enzyme stabilizer (examples of which include polyols such as propylene glycol or glycerol, sugar or sugar alcohol, lactic acid, reversible protease inhibitor, boric acid, or a boric acid derivative, e.g., an aromatic borate ester, or a phenyl boronic acid derivative such as 4-formylphenyl boronic acid).

The composition optionally include silicone or fatty-acid based suds suppressors; heuing dyes, calcium and magnesium cations, visual signaling ingredients, anti-foam (0.001 wt % to about 4.0 wt %), and/or structurant/thickener (0.01 wt % to 5 wt %, selected from the group consisting of diglycerides and triglycerides, ethylene glycol distearate, microcrystalline cellulose, cellulose based materials, microfiber cellulose, biopolymers, xanthan gum, gellan gum, and mixtures thereof).

The composition can be any liquid form, for example a liquid or gel form, or any combination thereof. The composition may be in any unit dose form, for example a pouch.

7.3. Heavy Duty Dry/Solid (HDD) Laundry Detergent Composition

Exemplary HDD laundry detergent compositions includes a detersive surfactant, including anionic detersive surfactants (e.g., linear or branched or random chain, substituted or unsubstituted alkyl sulphates, alkyl sulphonates, alkyl alkoxylated sulphate, alkyl phosphates, alkyl phosphonates, alkyl carboxylates and/or mixtures thereof), non-ionic detersive surfactant (e.g., linear or branched or random chain, substituted or unsubstituted $C_8$-$C_{18}$ alkyl ethoxylates, and/or $C_6$-$C_{12}$ alkyl phenol alkoxylates), cationic detersive surfactants (e.g., alkyl pyridinium compounds, alkyl quaternary ammonium compounds, alkyl quaternary phosphonium compounds, alkyl ternary sulphonium compounds, and mixtures thereof), zwitterionic and/or amphoteric detersive surfactants (e.g., alkanolamine sulpho-betaines), ampholytic surfactants, semi-polar non-ionic surfactants, and mixtures thereof; builders including phosphate free builders (for example zeolite builders examples which include zeolite A, zeolite X, zeolite P and zeolite MAP in the range of 0 wt % to less than 10 wt %), phosphate builders (for example sodium tri-polyphosphate in the range of 0 wt % to less than 10 wt %), citric acid, citrate salts and nitrilotriacetic acid, silicate salt (e.g., sodium or potassium silicate or sodium meta-silicate in the range of 0 wt % to less than 10 wt %, or layered silicate (SKS-6)); carbonate salt (e.g., sodium carbonate and/or sodium bicarbonate in the range of 0 wt % to less than 80 wt %); and bleaching agents including photobleaches (e.g., sulfonated zinc phthalocyanines, sulfonated aluminum phthalocyanines, xanthenes dyes, and mixtures thereof) hydrophobic or hydrophilic bleach activators (e.g., dodecanoyl oxybenzene sulfonate, decanoyl oxybenzene sulfonate, decanoyl oxybenzoic acid or salts thereof, 3,5,5-trimethy hexanoyl oxybenzene sulfonate, tetraacetyl ethylene diamine-TAED, nonanoyloxybenzene sulfonate-NOBS, nitrile quats, and mixtures thereof), sources of hydrogen peroxide (e.g., inorganic perhydrate salts examples of which include mono or tetra hydrate sodium salt of perborate, percarbonate, persulfate, perphosphate, or persilicate), preformed hydrophilic and/or hydrophobic peracids (e.g., percarboxylic acids and salts, percarbonic acids and salts, perimidic acids and salts, peroxymonosulfuric acids and salts, and mixtures thereof), and/or bleach catalysts (e.g., imine bleach boosters (examples of which include iminium cations and polyions), iminium zwitterions, modified amines, modified amine oxides, N-sulphonyl imines, N-phosphonyl imines, N-acyl imines, thiadiazole dioxides, perfluoroimines, cyclic sugar ketones, and mixtures thereof, and metal-containing bleach catalysts (e.g., copper, iron, titanium, ruthenium, tungsten, molybdenum, or manganese cations along with an auxiliary metal cations such as zinc or aluminum and a sequestrate such as ethylenediaminetetraacetic acid, ethylenediaminetetra(methylenephosphonic acid), and water-soluble salts thereof).

The composition preferably includes enzymes, e.g., proteases, amylases, lipases, cellulases, choline oxidases, peroxidases/oxidases, pectate lyases, mannanases, cutinases, laccases, phospholipases, lysophospholipases, acyltransferase, perhydrolase, arylesterase, and any mixture thereof.

The composition may optionally include additional detergent ingredients including perfume microcapsules, starch encapsulated perfume accord, hueing agents, additional polymers, including fabric integrity and cationic polymers, dyelock ingredients, fabric-softening agents, brighteners (for example C.I. Fluorescent brighteners), flocculating agents, chelating agents, alkoxylated polyamines, fabric deposition aids, and/or cyclodextrin.

7.4. Automatic Dishwashing (ADW) Detergent Composition

Exemplary ADW detergent composition includes non-ionic surfactants, including ethoxylated non-ionic surfactants, alcohol alkoxylated surfactants, epoxy-capped poly(oxyalkylated) alcohols, or amine oxide surfactants present in amounts from 0 to 10% by weight; builders in the range of 5-60% including phosphate builders (e.g., mono-phosphates, di-phosphates, tri-polyphosphates, other oligomeric-poylphosphates, sodium tripolyphosphate-STPP) and phosphate-free builders (e.g., amino acid-based compounds including methyl-glycine-diacetic acid (MGDA) and salts and derivatives thereof, glutamic-N,N-diacetic acid (GLDA) and salts and derivatives thereof, iminodisuccinic acid (IDS) and salts and derivatives thereof, carboxy methyl inulin and salts and derivatives thereof, nitrilotriacetic acid (NTA), diethylene triamine penta acetic acid (DTPA), B-alaninediacetic acid (B-ADA) and their salts, homopolymers and copolymers of poly-carboxylic acids and their partially or completely neutralized salts, monomeric polycarboxylic acids and hydroxycarboxylic acids and their salts in the range of 0.5% to 50% by weight; sulfonated/carboxylated polymers in the range of about 0.1% to about 50% by weight to provide dimensional stability; drying aids in the range of about 0.1% to about 10% by weight (e.g., polyesters, especially anionic polyesters, optionally together with further monomers with 3 to 6 functionalities—typically acid, alcohol or ester functionalities which are conducive to polycondensation, polycarbonate-, polyurethane- and/or polyurea-polyorganosiloxane compounds or precursor compounds, thereof, particularly of the reactive cyclic carbonate and urea type); silicates in the range from about 1% to about 20% by weight (including sodium or potassium silicates for example sodium disilicate, sodium meta-silicate and crystalline phyllosilicates); inorganic bleach (e.g., perhydrate salts such as perborate, percarbonate, perphosphate, persulfate and persilicate salts) and organic bleach (e.g., organic peroxyacids, including diacyl and tetraacylperoxides, especially diperoxydodecanedioc acid, diperoxytetradecanedioc acid, and diperoxyhexade-canedioc acid); bleach activators (i.e., organic peracid precursors in the range from about 0.1% to about 10% by weight); bleach catalysts (e.g., manganese triazacyclononane and related complexes, Co, Cu, Mn, and Fe bispyridylamine and related complexes, and pentamine acetate cobalt (III) and related complexes); metal care agents in the range from about 0.1% to 5% by weight (e.g., benzatriazoles, metal salts and complexes, and/or silicates); enzymes in the range from about 0.01 to 5.0 mg of active enzyme per gram of automatic dishwashing detergent composition (e.g., proteases, amylases, lipases, cellulases, choline oxidases, peroxidases/oxidases, pectate lyases, mannanases, cutinases, laccases, phospholipases, lysophospholipases, acyltransferase, perhydrolase, arylesterase, and mixtures thereof); and enzyme stabilizer components (e.g., oligosaccharides, polysaccharides, and inorganic divalent metal salts).

7.5. Additional Detergent Compositions

Additional exemplary detergent formulations to which the present amylase can be added are described, below, in the numbered paragraphs.

1) A detergent composition formulated as a granulate having a bulk density of at least 600 g/L comprising linear alkylbenzenesulfonate (calculated as acid) about 7% to about 12%; alcohol ethoxysulfate (e.g., $C_{12-18}$ alcohol, 1-2 ethylene oxide (EO)) or alkyl sulfate (e.g., $C_{16-18}$) about 1% to about 4%; alcohol ethoxylate (e.g., $C_{14-15}$ alcohol, 7 EO) about 5% to about 9%; sodium carbonate (e.g., $Na_2CO_3$) about 14% to about 20%; soluble silicate (e.g., $Na_2O$, $2SiO_2$) about 2 to about 6%; zeolite (e.g., $NaAlSiO_4$) about 15% to about 22%; sodium sulfate (e.g., $Na_2SO_4$) 0% to about 6%; sodium citrate/citric acid (e.g., $C_6H_5Na_3O_7/C_6H_8O_7$) about 0% to about 15%; sodium perborate (e.g., $NaBO_3H_2O$) about 11% to about 18%; TAED about 2% to about 6%; carboxymethylcellulose (CMC) and 0% to about 2%; polymers (e.g., maleic/acrylic acid, copolymer, PVP, PEG) 0-3%; enzymes (calculated as pure enzyme) 0.0001-0.1% protein; and minor ingredients (e.g., suds suppressors, perfumes, optical brightener, photobleach) 0-5%.

2) A detergent composition formulated as a granulate having a bulk density of at least 600 g/L comprising linear alkylbenzenesulfonate (calculated as acid) about 6% to about 11%; alcohol ethoxysulfate (e.g., $C_{12-18}$ alcohol, 1-2 EO) or alkyl sulfate (e.g., $C_{16-18}$) about 1% to about 3%; alcohol ethoxylate (e.g., $C_{14-15}$ alcohol, 7 EO) about 5% to about 9%; sodium carbonate (e.g., $Na_2CO_3$) about 15% to about 21%; soluble silicate (e.g., $Na_2O$, $2SiO_2$) about 1% to about 4%; zeolite (e.g., $NaAlSiO_4$) about 24% to about 34%; sodium sulfate (e.g., $Na_2SO_4$) about 4% to about 10%; sodium citrate/citric acid (e.g., $C_6H_5Na_3O_7/C_6H_8O_7$) 0% to about 15%; carboxymethylcellulose (CMC) 0% to about 2%; polymers (e.g., maleic/acrylic acid copolymer, PVP, PEG) 1-6%; enzymes (calculated as pure enzyme protein) 0.0001-0.1%; minor ingredients (e.g., suds suppressors, perfume) 0-5%.

3) A detergent composition formulated as a granulate having a bulk density of at least 600 g/L comprising linear alkylbenzenesulfonate (calculated as acid) about 5% to about 9%; alcohol ethoxylate (e.g., $C_{12-15}$ alcohol, 7 EO) about 7% to about 14%; Soap as fatty acid (e.g., $C_{16-22}$ fatty acid) about 1 to about 3%; sodium carbonate (as $Na_2CO_3$) about 10% to about 17%; soluble silicate (e.g., $Na_2O$, $2SiO_2$) about 3% to about 9%; zeolite (as $NaAlSiO_4$) about 23% to about 33%; sodium sulfate (e.g., $Na_2SO_4$) 0% to about 4%; sodium perborate (e.g., $NaBO_3H_2O$) about 8% to about 16%; TAED about 2% to about 8%; phosphonate (e.g., EDTMPA) 0% to about 1%; carboxymethylcellulose (CMC) 0% to about 2%; polymers (e.g., maleic/acrylic acid copolymer, PVP, PEG)

0-3%; enzymes (calculated as pure enzyme protein) 0.0001-0.1%; minor ingredients (e.g., suds suppressors, perfume, optical brightener) 0-5%.

4) A detergent composition formulated as a granulate having a bulk density of at least 600 g/L comprising linear alkylbenzenesulfonate (calculated as acid) about 8% to about 12%; alcohol ethoxylate (e.g., $C_{12-15}$ alcohol, 7 EO) about 10% to about 25%; sodium carbonate (as $Na_2CO_3$) about 14% to about 22%; soluble silicate (e.g., $Na_2O$, $2SiO_2$) about 1% to about 5%; zeolite (e.g., $NaAlSiO_4$) about 25% to about 35%; sodium sulfate (e.g., $Na_2SO_4$) 0% to about 10%; carboxymethylcellulose (CMC) 0% to about 2%; polymers (e.g., maleic/acrylic acid copolymer, PVP, PEG) 1-3%; enzymes (calculated as pure enzyme protein) 0.0001-0.1%; and minor ingredients (e.g., suds suppressors, perfume) 0-5%.

5) An aqueous liquid detergent composition comprising linear alkylbenzenesulfonate (calculated as acid) about 15% to about 21%; alcohol ethoxylate (e.g., $C_{12-15}$ alcohol, 7 EO or $C_{12-15}$ alcohol, 5 EO) about 12% to about 18%; soap as fatty acid (e.g., oleic acid) about 3% to about 13%; alkenyl-succinic acid ($C_{12-14}$) 0% to about 13%; aminoethanol about 8% to about 18%; citric acid about 2% to about 8%; phosphonate 0% to about 3%; polymers (e.g., PVP, PEG) 0% to about 3%; borate (e.g., $B_4O_7$) 0% to about 2%; ethanol 0% to about 3%; propylene glycol about 8% to about 14%; enzymes (calculated as pure enzyme protein) 0.0001-0.1%; and minor ingredients (e.g., dispersants, suds suppressors, perfume, optical brightener) 0-5%.

6) An aqueous structured liquid detergent composition comprising linear alkylbenzenesulfonate (calculated as acid) about 15% to about 21%; alcohol ethoxylate (e.g., $C_{12-15}$ alcohol, 7 EO, or $C_{12-15}$ alcohol, 5 EO) 3-9%; soap as fatty acid (e.g., oleic acid) about 3% to about 10%; zeolite (as $NaAlSiO_4$) about 14% to about 22%; potassium citrate about 9% to about 18%; borate (e.g., $B_4O_7$) 0% to about 2%; carboxymethylcellulose (CMC) 0% to about 2%; polymers (e.g., PEG, PVP) 0% to about 3%; anchoring polymers such as, e.g., lauryl methacrylate/acrylic acid copolymer; molar ratio 25:1, MW 3800) 0% to about 3%; glycerol 0% to about 5%; enzymes (calculated as pure enzyme protein) 0.0001-0.1%; and minor ingredients (e.g., dispersants, suds suppressors, perfume, optical brighteners) 0-5%.

7) A detergent composition formulated as a granulate having a bulk density of at least 600 g/L comprising fatty alcohol sulfate about 5% to about 10%; ethoxylated fatty acid monoethanolamide about 3% to about 9%; soap as fatty acid 0-3%; sodium carbonate (e.g., $Na_2CO_3$) about 5% to about 10%; Soluble silicate (e.g., $Na_2O$, $2SiO_2$) about 1% to about 4%; zeolite (e.g., $NaAlSiO_4$) about 20% to about 40%; Sodium sulfate (e.g., $Na_2SO_4$) about 2% to about 8%; sodium perborate (e.g., $NaBO_3H_2O$) about 12% to about 18%; TAED about 2% to about 7%; polymers (e.g., maleic/acrylic acid copolymer, PEG) about 1% to about 5%; enzymes (calculated as pure enzyme protein) 0.0001-0.1%; and minor ingredients (e.g., optical brightener, suds suppressors, perfume) 0-5%.

8) A detergent composition formulated as a granulate comprising linear alkylbenzenesulfonate (calculated as acid) about 8% to about 14%; ethoxylated fatty acid monoethanolamide about 5% to about 11%; soap as fatty acid 0% to about 3%; sodium carbonate (e.g., $Na_2CO_3$) about 4% to about 10%; soluble silicate ($Na_2O$, $2SiO_2$) about 1% to about 4%; zeolite (e.g., $NaAlSiO_4$) about 30% to about 50%; sodium sulfate (e.g., $Na_2SO_4$) about 3% to about 11%; sodium citrate (e.g., $C_6H_5Na_3O_7$) about 5% to about 12%; polymers (e.g., PVP, maleic/acrylic acid copolymer, PEG) about 1% to about 5%; enzymes (calculated as pure enzyme protein) 0.0001-0.1%; and minor ingredients (e.g., suds suppressors, perfume) 0-5%.

9) A detergent composition formulated as a granulate comprising linear alkylbenzenesulfonate (calculated as acid) about 6% to about 12%; nonionic surfactant about 1% to about 4%; soap as fatty acid about 2% to about 6%; sodium carbonate (e.g., $Na_2CO_3$) about 14% to about 22%; zeolite (e.g., $NaAlSiO_4$) about 18% to about 32%; sodium sulfate (e.g., $Na_2SO_4$) about 5% to about 20%; sodium citrate (e.g., $C_6H_5Na_3O_7$) about 3% to about 8%; sodium perborate (e.g., $NaBO_3H_2O$) about 4% to about 9%; bleach activator (e.g., NOBS or TAED) about 1% to about 5%; carboxymethylcellulose (CMC) 0% to about 2%; polymers (e.g., polycarboxylate or PEG) about 1% to about 5%; enzymes (calculated as pure enzyme protein) 0.0001-0.1%; and minor ingredients (e.g., optical brightener, perfume) 0-5%.

10) An aqueous liquid detergent composition comprising linear alkylbenzenesulfonate (calculated as acid) about 15% to about 23%; alcohol ethoxysulfate (e.g., $C_{12-15}$ alcohol, 2-3 EO) about 8% to about 15%; alcohol ethoxylate (e.g., $C_{12-15}$ alcohol, 7 EO, or $C_{12-15}$ alcohol, 5 EO) about 3% to about 9%; soap as fatty acid (e.g., lauric acid) 0% to about 3%; aminoethanol about 1% to about 5%; sodium citrate about 5% to about 10%; hydrotrope (e.g., sodium toluensulfonate) about 2% to about 6%; borate (e.g., $B_4O_7$) 0% to about 2%; carboxymethylcellulose 0% to about 1%; ethanol about 1% to about 3%; propylene glycol about 2% to about 5%; enzymes (calculated as pure enzyme protein) 0.0001-0.1%; and minor ingredients (e.g., polymers, dispersants, perfume, optical brighteners) 0-5%.

11) An aqueous liquid detergent composition comprising linear alkylbenzenesulfonate (calculated as acid) about 20% to about 32%; alcohol ethoxylate (e.g., $C_{12-15}$ alcohol, 7 EO, or $C_{12-15}$ alcohol, 5 EO) 6-12%; aminoethanol about 2% to about 6%; citric acid about 8% to about 14%; borate (e.g., $B_4O_7$) about 1% to about 3%; polymer (e.g., maleic/acrylic acid copolymer, anchoring polymer such as, e.g., lauryl methacrylate/acrylic acid copolymer) 0% to about 3%; glycerol about 3% to about 8%; enzymes (calculated as pure enzyme protein) 0.0001-0.1%; and minor ingredients (e.g., hydrotropes, dispersants, perfume, optical brighteners) 0-5%.

12) A detergent composition formulated as a granulate having a bulk density of at least 600 g/L comprising anionic surfactant (linear alkylbenzenesulfonate, alkyl sulfate, α-olefinsulfonate, α-sulfo fatty acid methyl esters, alkanesulfonates, soap) about 25% to about 40%; nonionic surfactant (e.g., alcohol ethoxylate) about 1% to about 10%; sodium carbonate (e.g., $Na_2CO_3$) about 8% to about 25%; soluble silicates (e.g., $Na_2O$, $2SiO_2$) about 5% to about 15%; sodium sulfate (e.g., $Na_2SO_4$) 0% to about 5%; zeolite ($NaAlSiO_4$) about 15% to about 28%; sodium perborate (e.g., $NaBO_3.4H_2O$) 0% to about 20%; bleach activator (TAED or NOBS) about 0% to about 5%; enzymes (calculated as pure enzyme protein) 0.0001-0.1%; minor ingredients (e.g., perfume, optical brighteners) 0-3%.

13) Detergent compositions as described in compositions 1)-12) supra, wherein all or part of the linear alkylbenzenesulfonate is replaced by ($C_{12}$-$C_{18}$) alkyl sulfate.

14) A detergent composition formulated as a granulate having a bulk density of at least 600 g/L comprising ($C_{12}$-$C_{18}$) alkyl sulfate about 9% to about 15%; alcohol ethoxylate about 3% to about 6%; polyhydroxy alkyl fatty acid amide about 1% to about 5%; zeolite (e.g., $NaAlSiO_4$) about 10% to about 20%; layered disilicate (e.g., SK56 from Hoechst) about 10% to about 20%; sodium carbonate (e.g., $Na_2CO_3$) about 3% to about 12%; soluble silicate (e.g., $Na_2O$, $2SiO_2$) 0% to about 6%; sodium citrate about 4% to about 8%; sodium percarbonate about 13% to about 22%; TAED about 3% to about 8%; polymers (e.g., polycarboxylates and PVP) 0% to about 5%; enzymes (calculated as pure enzyme protein) 0.0001-0.1%; and minor ingredients (e.g., optical brightener, photobleach, perfume, suds suppressors) 0-5%.

15) A detergent composition formulated as a granulate having a bulk density of at least 600 g/L comprising ($C_{12}$-$C_{18}$) alkyl sulfate about 4% to about 8%; alcohol ethoxylate about 11% to about 15%; soap about 1% to about 4%; zeolite MAP or zeolite A about 35% to about 45%; sodium carbonate (as $Na_2CO_3$) about 2% to about 8%; soluble silicate (e.g., $Na_2O$, $2SiO_2$) 0% to about 4%; sodium percarbonate about 13% to about 22%; TAED 1-8%; carboxymethylcellulose (CMC) 0% to about 3%; polymers (e.g., polycarboxylates and PVP) 0% to about 3%; enzymes (calculated as pure enzyme protein) 0.0001-0.1%; and minor ingredients (e.g., optical brightener, phosphonate, perfume) 0-3%.

16) Detergent formulations as described in 1)-15) supra, which contain a stabilized or encapsulated peracid, either as an additional component or as a substitute for already specified bleach systems.

17) Detergent compositions as described supra in 1), 3), 7), 9), and 12), wherein perborate is replaced by percarbonate.

18) Detergent compositions as described supra in 1), 3), 7), 9), 12), 14), and 15), which additionally contain a manganese catalyst. The manganese catalyst for example is one of the compounds described in "Efficient manganese catalysts for low-temperature bleaching," Nature 369: 637-639 (1994).

19) Detergent composition formulated as a non-aqueous detergent liquid comprising a liquid nonionic surfactant such as, e.g., linear alkoxylated primary alcohol, a builder system (e.g., phosphate), an enzyme(s), and alkali. The detergent may also comprise anionic surfactant and/or a bleach system.

As above, the present amylase polypeptide may be incorporated at a concentration conventionally employed in detergents. It is at present contemplated that, in the detergent composition, the enzyme may be added in an amount corresponding to 0.00001-1.0 mg (calculated as pure enzyme protein) of amylase polypeptide per liter of wash liquor.

The detergent composition may also contain other conventional detergent ingredients, e.g., deflocculant material, filler material, foam depressors, anti-corrosion agents, soil-suspending agents, sequestering agents, anti-soil redeposition agents, dehydrating agents, dyes, bactericides, fluorescers, thickeners, and perfumes.

The detergent composition may be formulated as a hand (manual) or machine (automatic) laundry detergent composition, including a laundry additive composition suitable for pre-treatment of stained fabrics and a rinse added fabric softener composition, or be formulated as a detergent composition for use in general household hard surface cleaning operations, or be formulated for manual or automatic dishwashing operations.

Any of the cleaning compositions described, herein, may include any number of additional enzymes. In general the enzyme(s) should be compatible with the selected detergent, (e.g., with respect to pH-optimum, compatibility with other enzymatic and non-enzymatic ingredients, and the like), and the enzyme(s) should be present in effective amounts. The following enzymes are provided as examples.

Proteases:

Suitable proteases include those of animal, vegetable or microbial origin. Chemically modified or protein engineered mutants are included, as well as naturally processed proteins. The protease may be a serine protease or a metalloprotease, an alkaline microbial protease, a trypsin-like protease, or a chymotrypsin-like protease. Examples of alkaline proteases are subtilisins, especially those derived from *Bacillus*, e.g., subtilisin Novo, subtilisin Carlsberg, subtilisin 309, subtilisin 147, and subtilisin 168 (see, e.g., WO 89/06279). Examples of trypsin-like proteases are trypsin (e.g., of porcine or bovine origin), and *Fusarium* proteases (see, e.g., WO 89/06270 and WO 94/25583). Examples of useful proteases also include but are not limited to the variants described in WO 92/19729, WO 98/20115, WO 98/20116, and WO 98/34946. Commercially available protease enzymes include but are not limited to: ALCALASE®, SAVINASE®, PRIMASE™, DURALASE™, ESPERASE®, KANNASE™, and BLAZE™ (Novo Nordisk A/S and Novozymes A/S); MAXATASE®, MAXACAL™, MAXAPEM™, PROPERASE®, PURAFECT®, PURAFECT OXP™, FN2™, and FN3™ (Danisco US Inc.). Other exemplary proteases include NprE from *Bacillus amyloliquifaciens* and ASP from *Cellulomonas* sp. strain 69B4.

Lipases:

Suitable lipases include those of bacterial or fungal origin. Chemically modified, proteolytically modified, or protein engineered mutants are included. Examples of useful lipases include but are not limited to lipases from *Humicola* (synonym *Thermomyces*), e.g., from *H. lanuginosa* (*T. lanuginosus*) (see e.g., EP 258068 and EP 305216), from *H. insolens* (see e.g., WO 96/13580); a *Pseudomonas* lipase (e.g., from *P. alcaligenes* or *P. pseudoalcaligenes*; see, e.g., EP 218 272), *P. cepacia* (see e.g., EP 331 376), *P. stutzeri* (see e.g., GB 1,372,034), *P. fluorescens*, *Pseudomonas* sp. strain SD 705 (see e.g., WO 95/06720 and WO 96/27002), *P. wisconsinensis* (see e.g., WO 96/12012); a *Bacillus* lipase (e.g., from *B. subtilis*; see e.g., Dartois et al. *Biochemica et Biophysica Acta*, 1131: 253-360 (1993)), *B. stearothermophilus* (see e.g., JP 64/744992), or *B. pumilus* (see e.g., WO 91/16422). Additional lipase variants contemplated for use in the formulations include those described for example in: WO 92/05249, WO 94/01541, WO 95/35381, WO 96/00292, WO 95/30744, WO 94/25578, WO 95/14783, WO 95/22615, WO 97/04079, WO 97/07202, EP 407225, and EP 260105. Some commercially available lipase enzymes include LIPOLASE® and LIPOLASE ULTRA™ (Novo Nordisk A/S and Novozymes A/S).

Polyesterases:

Suitable polyesterases can be included in the composition, such as those described in, for example, WO 01/34899, WO 01/14629, and U.S. Pat. No. 6,933,140.

Amylases: The compositions can be combined with other amylases, such as non-production enhanced amylase. These can include commercially available amylases, such as but not limited to STAINZYME®, NATALASE®, DURAMYL®, TERMAMYL®, FUNGAMYL® and BAN™ (Novo Nordisk A/S and Novozymes A/S); RAPIDASE®, POWERASE®, and PURASTAR® (from Danisco US Inc.).

Cellulases:

Cellulases can be added to the compositions. Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed for example in U.S. Pat. Nos. 4,435,307; 5,648,263; 5,691,178; 5,776,757; and WO 89/09259. Exemplary cellulases contemplated for use are those having color care benefit for the textile. Examples of such cellulases are cellulases described in for example EP 0495257, EP 0531372, WO 96/11262, WO 96/29397, and WO 98/08940. Other examples are cellulase variants, such as those described in WO 94/07998; WO 98/12307; WO 95/24471; PCT/DK98/00299; EP 531315; U.S. Pat. Nos. 5,457,046; 5,686,593; and 5,763,254. Commercially available cellulases include CELLUZYME® and CAREZYME® (Novo Nordisk A/S and Novozymes A/S); CLAZINASE® and PURADAX HA® (Danisco US Inc.); and KAC-500(B)™ (Kao Corporation).

Peroxidases/Oxidases:

Suitable peroxidases/oxidases contemplated for use in the compositions include those of plant, bacterial or fungal origin. Chemically modified or protein engineered mutants are included. Examples of useful peroxidases include peroxidases from *Coprinus*, e.g., from *C. cinereas*, and variants thereof as those described in WO 93/24618, WO 95/10602, and WO 98/15257. Commercially available peroxidases include for example GUARDZYME™ (Novo Nordisk A/S and Novozymes A/S).

The detergent composition can also comprise 2,6-β-D-fructan hydrolase, which is effective for removal/cleaning of biofilm present on household and/or industrial textile/laundry.

The detergent enzyme(s) may be included in a detergent composition by adding separate additives containing one or more enzymes, or by adding a combined additive comprising all of these enzymes. A detergent additive, i.e. a separate additive or a combined additive, can be formulated e.g., as a granulate, a liquid, a slurry, and the like. Exemplary detergent additive formulations include but are not limited to granulates, in particular non-dusting granulates, liquids, in particular stabilized liquids or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (e.g., polyethyleneglycol, PEG) with mean molar weights of 1,000 to 20,000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in, for example, GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition may be in any convenient form, e.g., a bar, a tablet, a powder, a granule, a paste, or a liquid. A liquid detergent may be aqueous, typically containing up to about 70% water, and 0% to about 30% organic solvent. Compact detergent gels containing about 30% or less water are also contemplated. The detergent composition can optionally comprise one or more surfactants, which may be non-ionic, including semi-polar and/or anionic and/or cationic and/or zwitterionic. The surfactants can be present in a wide range, from about 0.1% to about 60% by weight.

When included therein the detergent will typically contain from about 1% to about 40% of an anionic surfactant, such as linear alkylbenzenesulfonate, α-olefinsulfonate, alkyl sulfate (fatty alcohol sulfate), alcohol ethoxysulfate, secondary alkanesulfonate, α-sulfo fatty acid methyl ester, alkyl- or alkenylsuccinic acid, or soap.

When included therein, the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl-N-alkyl derivatives of glucosamine ("glucamides").

The detergent may contain 0% to about 65% of a detergent builder or complexing agent such as zeolite, diphosphate, triphosphate, phosphonate, carbonate, citrate, nitrilotriacetic acid, ethylenediaminetetraacetic acid (EDTA), diethylenetriaminepentaacetic acid, alkyl- or alkenylsuccinic acid, soluble silicates or layered silicates (e.g., SKS-6 from Hoechst).

The detergent may comprise one or more polymers. Exemplary polymers include carboxymethylcellulose (CMC), poly(vinylpyrrolidone) (PVP), poly(ethylene glycol) (PEG), poly(vinyl alcohol) (PVA), poly(vinylpyridine-N-oxide), poly(vinylimidazole), polycarboxylates e.g., polyacrylates, maleic/acrylic acid copolymers), and lauryl methacrylate/acrylic acid copolymers.

The enzyme(s) of the detergent composition may be stabilized using conventional stabilizing agents, e.g., as polyol (e.g., propylene glycol or glycerol), a sugar or sugar alcohol, lactic acid, boric acid, or a boric acid derivative (e.g., an aromatic borate ester), or a phenyl boronic acid derivative (e.g., 4-formylphenyl boronic acid). The composition may be formulated as described in WO 92/19709 and WO 92/19708.

It is contemplated that in the detergent compositions, in particular the enzyme variants, may be added in an amount corresponding to about 0.01 to about 100 mg of enzyme protein per liter of wash liquor (e.g., about 0.05 to about 5.0 mg of enzyme protein per liter of wash liquor or 0.1 to about 1.0 mg of enzyme protein per liter of wash liquor).

Although the present compositions and methods have been described with reference to the details below, it would be understood that various modifications can be made.

7.6. Methods of Assessing Amylase Activity in Detergent Compositions

Numerous α-amylase cleaning assays are known in the art, including swatch and micro-swatch assays. The appended Examples describe only a few such assays.

In order to further illustrate the compositions and methods, and advantages thereof, the following specific examples are given with the understanding that they are illustrative rather than limiting.

8. Brewing Compositions

An AcAmy1 or variant thereof may be a component of a brewing composition used in a process of brewing, i.e., making a fermented malt beverage. Non-fermentable carbohydrates form the majority of the dissolved solids in the final beer. This residue remains because of the inability of malt amylases to hydrolyze the alpha-1,6-linkages of the starch. The non-fermentable carbohydrates contribute about 50 calories per 12 ounces of beer. The AcAmy1 or variant thereof, in combination with a glucoamylase and optionally a pullulanase and/or isoamylase, assist in converting the starch into dextrins and fermentable sugars, lowering the residual non-fermentable carbohydrates in the final beer.

The principal raw materials used in making these beverages are water, hops and malt. In addition, adjuncts such as common corn grits, refined corn grits, brewer's milled yeast, rice, sorghum, refined corn starch, barley, barley starch, dehusked barley, wheat, wheat starch, torrified cereal, cereal flakes, rye, oats, potato, tapioca, and syrups, such as corn syrup, sugar cane syrup, inverted sugar syrup, barley and/or wheat syrups, and the like may be used as a source of starch.

For a number of reasons, the malt, which is produced principally from selected varieties of barley, has the greatest effect on the overall character and quality of the beer. First, the malt is the primary flavoring agent in beer. Second, the malt provides the major portion of the fermentable sugar. Third, the malt provides the proteins, which will contribute to the body and foam character of the beer. Fourth, the malt provides the necessary enzymatic activity during mashing. Hops also contribute significantly to beer quality, including flavoring. In particular, hops (or hops constituents) add desirable bittering substances to the beer. In addition, the hops act as protein precipitants, establish preservative agents and aid in foam formation and stabilization.

Grains, such as barley, oats, wheat, as well as plant components, such as corn, hops, and rice, also are used for brewing, both in industry and for home brewing. The components used in brewing may be unmalted or may be malted, i.e., partially germinated, resulting in an increase in the levels of enzymes, including α-amylase. For successful brewing, adequate levels of α-amylase enzyme activity are necessary to ensure the appropriate levels of sugars for fermentation. An AcAmy1 or variant thereof, by itself or in combination with another α-amylase(s), accordingly may be added to the components used for brewing.

As used herein, the term "stock" means grains and plant components that are crushed or broken. For example, barley used in beer production is a grain that has been coarsely ground or crushed to yield a consistency appropriate for producing a mash for fermentation. As used herein, the term "stock" includes any of the aforementioned types of plants and grains in crushed or coarsely ground forms. The methods described herein may be used to determine α-amylase activity levels in both flours and stock.

Processes for making beer are well known in the art. See, e.g., Wolfgang Kunze (2004) "Technology Brewing and Malting," Research and Teaching Institute of Brewing, Berlin (VLB), 3rd edition. Briefly, the process involves: (a) preparing a mash, (b) filtering the mash to prepare a wort, and (c) fermenting the wort to obtain a fermented beverage, such as beer. Typically, milled or crushed malt is mixed with water and held for a period of time under controlled temperatures to permit the enzymes present in the malt to convert the starch present in the malt into fermentable sugars. The mash is then transferred to a mash filter where the liquid is separated from the grain residue. This sweet liquid is called "wort," and the left over grain residue is called "spent grain." The mash is typically subjected to an extraction, which involves adding water to the mash in order to recover the residual soluble extract from the spent grain. The wort is then boiled vigorously to sterilizes the wort and help develop the color, flavor and odor. Hops are added at some point during the boiling. The wort is cooled and transferred to a fermentor.

The wort is then contacted in a fermentor with yeast. The fermentor may be chilled to stop fermentation. The yeast flocculates and is removed. Finally, the beer is cooled and stored for a period of time, during which the beer clarifies and its flavor develops, and any material that might impair the appearance, flavor and shelf life of the beer settles out. The beer usually contains from about 2% to about 10% v/v alcohol, although beer with a higher alcohol content, e.g., 18% v/v, may be obtained. Prior to packaging, the beer is carbonated and, optionally, filtered and pasteurized.

The brewing composition comprising the AcAmy1 or variant thereof, in combination with a glucoamylase and optionally a pullulanase and/or isoamylase, may be added to the mash of step (a) above, i.e., during the preparation of the mash. Alternatively, or in addition, the brewing composition may be added to the mash of step (b) above, i.e., during the filtration of the mash. Alternatively, or in addition, the brewing composition may be added to the wort of step (c) above, i.e., during the fermenting of the wort.

A fermented beverage, such as a beer, can be produced by one of the methods above. The fermented beverage can be a beer, such as full malted beer, beer brewed under the "Reinheitsgebot," ale, IPA, lager, bitter, Happoshu (second beer), third beer, dry beer, near beer, light beer, low alcohol beer, low calorie beer, porter, bock beer, stout, malt liquor, non-alcoholic beer, non-alcoholic malt liquor and the like, but also alternative cereal and malt beverages such as fruit flavored malt beverages, e.g., citrus flavored, such as lemon-, orange-, lime-, or berry-flavored malt beverages, liquor flavored malt beverages, e.g., vodka-, rum-, or tequila-flavored malt liquor, or coffee flavored malt beverages, such as caffeine-flavored malt liquor, and the like.

9. Reduction of Iodine-Positive Starch

AcAmy1 and variants thereof may reduce the iodine-positive starch (IPS), when used in a method of liquefaction and/or saccharification. One source of IPS is from amylose that escapes hydrolysis and/or from retrograded starch polymer. Starch retrogradation occurs spontaneously in a starch paste, or gel on ageing, because of the tendency of starch molecules to bind to one another followed by an increase in crystallinity. Solutions of low concentration become increasingly cloudy due to the progressive association of starch molecules into larger articles. Spontaneous precipitation takes place and the precipitated starch appears to be reverting to its original condition of cold-water insolubility. Pastes of higher concentration on cooling set to a gel, which on ageing becomes steadily firmer due to the increasing association of the starch molecules. This arises because of the strong tendency for hydrogen bond formation between hydroxy groups on adjacent starch molecules. See J. A. Radley, ed., STARCH AND ITS DERIVATIVES 194-201 (Chapman and Hall, London (1968)).

The presence of IPS in saccharide liquor negatively affects final product quality and represents a major issue with downstream processing. IPS plugs or slows filtration system, and fouls the carbon columns used for purification. When IPS reaches sufficiently high levels, it may leak through the carbon columns and decrease production efficiency. Additionally, it may results in hazy final product upon storage, which is unacceptable for final product quality. The amount of IPS can be reduced by isolating the saccharification tank and blending the contents back. IPS nevertheless will accumulate in carbon columns and filter systems, among other things. The use of AcAmy1 or variants thereof thus is expected to improve overall process performance by reducing the amount of IPS.

EXAMPLES

Example 1

Cloning of AcAmy1

The genome of *Aspergillus clavatus* is sequenced. See *Aspergillus* 10-way comparative database asp2_v3, on the Internet at hypertext transfer protocol://aspgd.broadinstitute. org/cgi-bin/asp2_v3/shared/ show_organism.cgi?site=asp2_v3&id=2 (downloaded May 24, 2010). *A. clavatus* encodes a glycosyl hydrolase with homology to other fungal alpha-amylase as determined from a BLAST search. See FIG. 1. The nucleotide sequence of the AcAmy1 gene, which comprises eight introns, is set forth in SEQ ID NO: 2. A similar sequence is present at NCBI Reference No. XM_001272244.1, *Aspergillus clavatus* NRRL 1 alpha amylase, putative (ACLA_052920; SEQ ID NO: 7). The polynucleotide disclosed at NCBI Reference No. XM_001272244.1 represents a cDNA sequence obtained from the mRNA encoding AcAmy1 that lacks the eight intron sequences.

The AcAmy1 gene was amplified from genomic DNA of *Aspergillus clavatus* using the following primers: Primer 1 (Not I) 5'-ggggcggccgccaccATGAAGCT-TCTAGCTTTGACAAC-3' (SEQ ID NO: 8), and Primer 2 (Asc I) 5'-cceggcgcgccttaTCACCTCCAA-GAGCTGTCCAC-3' (SEQ ID NO: 9). After digestion with Not I and Asc I, the PCR product was cloned into pTrex3gM expression vector (described in U.S. Published Application 2011/0136197 A1) digested with the same restriction enzymes, and the resulting plasmid was labeled pJG153. A plasmid map of pJG153 is provided in FIG. 2. The sequence of the AcAmy1 gene was confirmed by DNA sequencing. The sequence differs from SEQ ID NO: 2 at two positions, bases 1165 (G→A) and 1168 (T→C). The changes in nucleotide sequence do not change the AcAmy1 amino acid sequence.

Example 2

Expression and Purification of AcAmy1

The plasmid pJG153 was transformed into a quad-deleted *Trichoderma reesei* strain (described in WO 05/001036) using biolistic method (Te'o et al., *J. Microbiol. Methods* 51:393-99, 2002). The protein was secreted into the extracellular medium, and the filtered culture medium was used to perform SDS-PAGE and an alpha-amylase activity assay to confirm the enzyme expression.

The AcAmy1 protein was purified using ammonium sulfate precipitation plus 2 steps chromatography. About 900 mL of broth from shake flask was added ammonium sulfate to give a final ammonium sulfate concentration of 3 M. The sample was centrifuged at 10,000×g for 30 mM, and the pellet was resuspended in 20 mM sodium phosphate buffer pH 7.0, 1 M ammonium sulfate (buffer A). After filtering, this sample was loaded onto 70 mL Phenyl-Sepharose™ column equilibrated with buffer A. After loading, the column was washed with three column volumes of buffer A. The target protein eluted at 0.6 M ammonium sulfate. The fractions from the Phenyl-Sepharose™ column were pooled and dialyzed against 20 mM Tris-HCl, pH 8.0 (buffer C) overnight, and then loaded onto 50 mL Q-HP Sepharose column equilibrated with buffer C. The target protein was eluted with a gradient of 20 column volumes of 0-100% buffer C with 1 M NaCl (buffer D). Fractions containing AcAmy1 were pooled and concentrated using 10 kDa Amicon Ultra-15 devices. The sample was above 90% pure and stored in 40% glycerol at −80° C.

Example 3

Determining AcAmy1 α-Amylase Activity

α-Amylase activity was assayed based on its releasing of reducing sugar from potato amylopectin substrate. Formation of reducing sugars was monitored colorimetrically via a PAHBAH assay. Activity number is reported as equivalents of glucose released per minute.

The 2.5% potato amylopectin (AP, Fluka Cat. No. 10118) substrate was prepared with 1.25 g ds in total of 50 g water/ 0.005% Tween followed by heating for 1 min with a micro-waving in 15 s intervals and stirring. A buffer cocktail was prepared by mixing 5 mL of 0.5 M Na acetate, pH 5.8; 2.5 mL 1 M NaCl; 0.2 mL 0.5 M CaCl$_2$; and 7.3 mL water/Tween (167 mM Na acetate, 167 mM NaCl, 6.67 mM CaCl$_2$).

Purified enzyme was diluted to 0.4 mg/mL (400 ppm) in water/Tween as stock solution. On the first row of a non-binding microtiter plate (Corning 3641), 195 µL of water were added, and 100 µL water/Tween was placed in all the remaining wells. 5 µL of 400 ppm enzyme was added to the first row so that the enzyme concentration is 10 ppm in the well and the final enzyme concentration in the reaction is 2 ppm. A two-fold serial dilution was carried out (40 µL+40 µL), through the seventh well, leaving the eighth well as an enzyme-free blank. 15 µL of the buffer cocktail, followed by 25 µL of amylopectin, was dispensed to a PCR plate using an automatic pipette. Reactions were initiated by dispensing 10 µL of the enzyme dilution series to the PCR plate, mixing quickly with a vortexer, and incubating for 10 minutes on a PCR heat block at 50° C. with a heated lid (80° C.). After exactly 10 minutes, 20 µL of 0.5 N NaOH was added to the plate followed by vortexing to terminate the reaction.

Total reducing sugars present in tubes were assayed via a PAHBAH method: 80 µL of 0.5 N NaOH was aliquoted to a PCR microtube plate followed by 20 µL of PAHBAH reagent (5% w/v 4-hydroxybenzoic acid hydrazide in 0.5 N HCl). 10 µL of terminated reactions were added to each row using a multichannel pipette and mixed briefly with up and down pipetting. The loaded plate was incubated at 95° C. for 2 min sealed with tin foil. 80 µL of developed reactions were transferred to a polystyrene microtiter plate (Costar 9017), and the OD was determined at 410 nm. The resulting OD values were plotted against enzyme concentration using Microsoft Excel. Linear regression was used to determine the slope of the linear part of the plot. Amylase activity was quantified using Equation 1:

$$\text{Specific Activity (Unit/mg)} = \text{Slope (enzyme)/slope (std)} \times 100 \quad (1),$$

where 1 Unit=1 µmol glucose eq./min

A representative specific activity of AcAmy1 and the benchmark amylase AkAA are shown in Table 1.

TABLE 1

| Specific activity of purified alpha-amylases on amylopectin. | |
|---|---|
| Protein | Specific Activity (U/mg) |
| AkAA | 58.9 |
| AcAmy1 | 300.9 |

Example 4

Effect of pH on AcAmy1 α-Amylase Activity

The effect of pH on AcAmy1 amylase activity was monitored using the alpha-amylase assay protocol as described in Example 3 in a pH range of 3.0 to 10.0. Buffer stocks were prepared as 1 M sodium acetate buffer stocks with pH 3.0 to 6.0, 1 M HEPES buffer stocks with pH 6.0 to pH 9.0, and 1 M CAPS buffer stock pH 10.0. The working buffer contains 2.5 mL of 1 M Na acetate (pH 3.5-6.5) or 1 M HEPES (pH 7-9), every half pH units, with 2.5 mL of 1 M NaCl and 50 µL of 2 M CaCl$_2$, 10 mL water/Tween (167 mM each buffer and NaCl, 6.67 mM CaCl$_2$), so that the final enzyme reaction mixture contains 50 mM each buffer and NaCl, 2 mM CaCl$_2$.

Figure 3A:
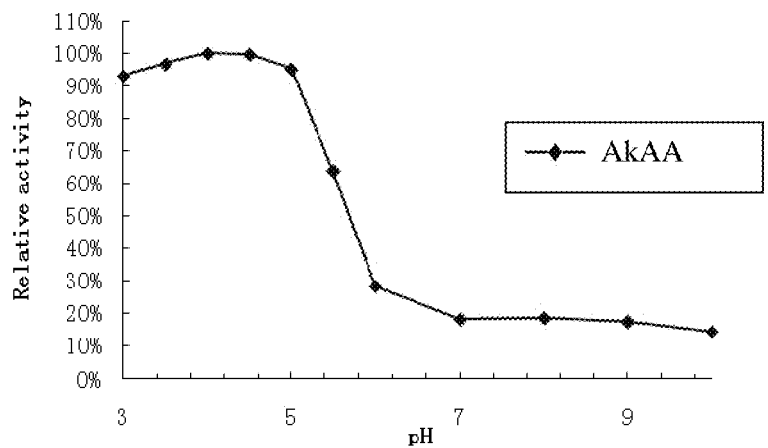
FIG. 3A depicts the dependence of α-amylase activity (relative units) of *Aspergillus kawachii* α-amylase (AkAA) on pH.
Figure 3B:
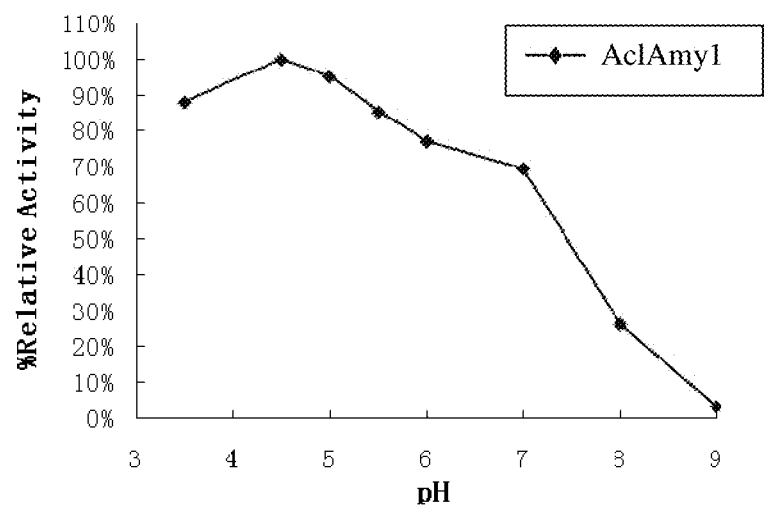
FIG. 3B depicts the dependence of α-amylase activity (relative units) of AcAmy1 on pH. α-Amylase activity was based on 2 ppm enzyme and assayed by the release of reducing sugar from potato amylopectin substrate at 50° C.

Enzyme stocks were prepared in water/0.005% Tween at concentrations in the linear range of the PAHBAH assay. 15 µL of the working buffer (pH 3.5-7.0 using sodium acetate, pH 6.0-9.0 using HEPES), followed by 25 µL of amylopectin, was dispensed to a PCR plate using an automatic pipette. Sodium acetate and HEPES buffers were separately used at pH values of 6.0, 6.5, and 7.0 to confirm there are no buffer effects on enzyme activity. Reactions were initiated by dispensing 10 µL of enzyme stock to the PCR plate, mixing quickly on a vortexer, and incubating for 10 minutes on a PCR heat block at 50° C. with a heated lid (80° C.). Reactions were performed in replicates of three. Blank samples using the different pH buffers alone were included. After exactly 10 min, 20 µL of 0.5 N NaOH was added to the plate, followed by vortexing to terminate the reaction. Total reducing sugars present in wells were assayed with the PAHBAH method described above. The resulting OD values were converted to a percentage of relative activity by defining the optimum pH as 100% activity. The percent relative activity, plotted as a function of pH, is shown in FIG. 3A (benchmark AkAA) and FIG. 3B (AcAmy1). The optimum pH and pH range at >70% of maximum activity when hydrolysis is measured at 50° C. are listed in Table 2.

TABLE 2

Optimum pH and pH range (>70% activity) at 50° C. for purified alpha-amylases.

| Protein | Optimum pH | pH range (>70% activity) | pH range (≥85% activity) |
|---|---|---|---|
| AkAA | 4.0 | pH <5.4 | pH 3-5 |
| AcAmy1 | 4.5 | pH <7.0 | pH 3.5-5.5 |

Example 5

Effect of Temperature on AcAmy1 α-Amylase Activity

The fungal alpha-amylase activity was monitored using the alpha-amylase assay protocol as described in Example 4 in a temperature range of 30° C. to 95° C. Buffer stock of the optimum pH of each enzyme is prepared as 2.5 mL of 1 M buffer (sodium acetate or HEPES, depending on the enzyme's optimum pH), 2.5 mL of 1 M NaCl and 50 µL of 2 M $CaCl_2$, 10 mL water/Tween (167 mM ea. buffer and NaCl, 6.67 mM $CaCl_2$), so that the final reaction mixture contained 50 mM each buffer and NaCl, 2 mM $CaCl_2$.

Figure 4A:
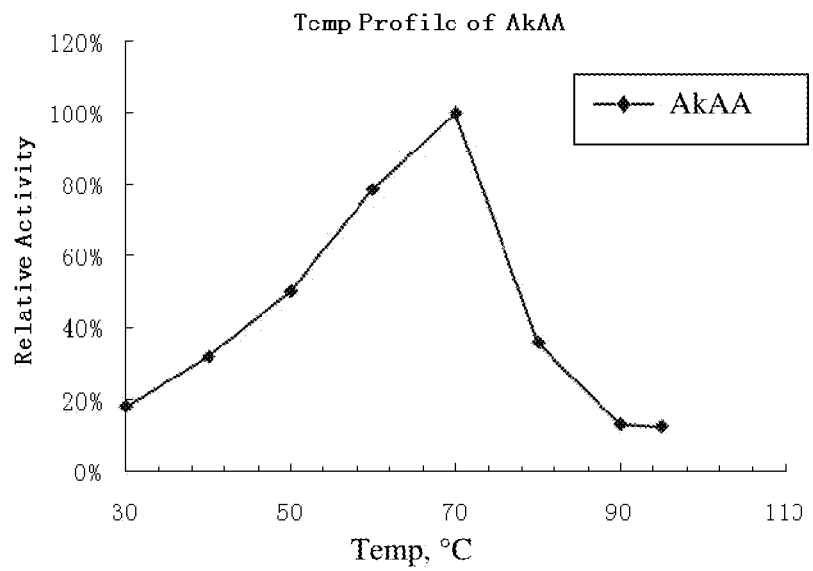
FIG. 4A depicts the dependence of α-amylase activity (relative units) of AkAA on temperature.
Figure 4B:
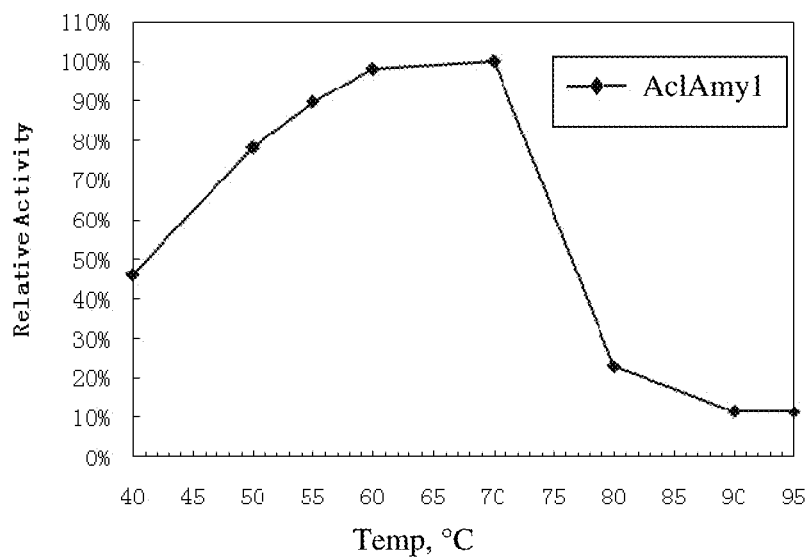
FIG. 4B depicts the dependence of α-amylase activity (relative units) of AcAmy1 on temperature. α-Amylase activity was based on 2 ppm enzyme and assayed by the release of reducing sugar from potato amylopectin substrate at pH 4.0 (AkAA) or pH 4.5 (AcAmy1).

Enzyme stocks were prepared as described above. 15 µL of the buffer stock (optimum pH, predetermined), followed by 25 µL of the amylopectin, were dispensed to a PCR plate using an automatic pipette. Reactions were initiated by dispensing 10 µL of enzyme to the PCR plate, mixing quickly on a vortexer, and incubating for 10 minutes on a PCR heat block, at 30-95° C. (every 5-10° C.) with the lid heated to the same or greater than the incubation temperature. Reactions were performed in replicates of three. Blank samples using the different buffers alone were included. After exactly 10 min, 20 µL of 0.5 N NaOH were added to the plate followed by vortexing to terminate the reactions. Total reducing sugars present in tubes were assayed with a PAHBAH method as described above. The resulting OD values were converted to a percentage of relative activity by defining the optimum temperature as 100% activity. The temperature profiles of the fungal alpha-amylases are shown in FIG. 4A (AkAA benchmark) and FIG. 4B (AcAmy1). The optimum temperature and temperature range at >70% of maximum activity are listed in Table 3, when measured at the indicated optimal pH of the enzyme.

TABLE 3

Optimum temperature and temperature range (>70% activity) for alpha-amylases at their respective optimum pH.

| Protein | Optimum Temperature | Temp range (>70% activity) |
|---|---|---|
| AkAA, pH 4.0 | 70° C. | 56-75° C. |
| AcAmy1, pH 4.5 | 66° C. | 47-74° C. |

Example 6

Effect of Sustained Low pH on AcAmy1 α-Amylase Activity

SSF is usually conducted at pH 3.5-5.5, 32° C. for 55 hours, and the enzymes used in the process should be able to maintain their activity during the whole process. Thus, it is useful to know the low pH stability of the α-amylases. The following protocol is used for testing the pH stability.

Figure 5A:
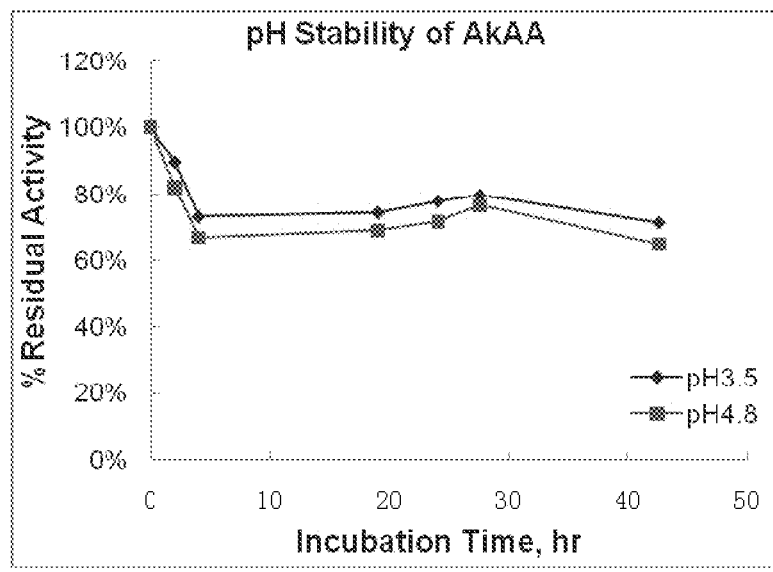
FIG. 5A depicts the residual α-amylase activity (relative units) of AkAA after incubation at pH 3.5 or 4.8 for the time periods shown.
Figure 5B:
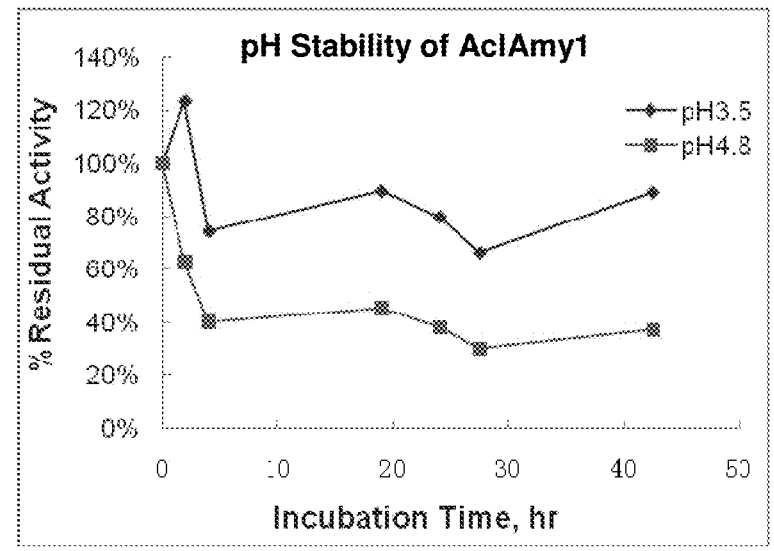
FIG. 5B depicts the residual α-amylase activity (relative units) of AcAmy1 at pH 3.5 or 4.8 for the time periods shown. α-Amylase activity was based on 2 ppm enzyme and assayed by the release of reducing sugar from potato amylopectin substrate.

The enzymes were diluted in 50 mM sodium acetate at pH 3.5 and 4.8 to a concentration in the linear range of the α-amylase assay described above. The diluted enzymes were incubated at room temperature, sampling 10 µL for assays at t=0, 2, 4, 19, 24, 28, and 43 hr. Assays were conducted under standard conditions using amylopectin as a substrate and PAHBAH for the reducing sugar at pH 5, 50° C., as described above. Data were processed by normalizing signal to the glucose standard and plotted as the percentage of residual activity relative to t=0 as a function of time. FIG. 5A and FIG. 5B show the residual activity of the benchmark AkAA and AcAmy1, respectively, after incubation at pH 3.5 or 4.8 for different time periods. Both AkAA and AcAmy1 maintain >60% activity after extended incubation at pH 3.5. AcAmy1 retained less activity than AkAA at pH 4.8. In contrast, amylases of bacteria origin usually lost most of their activity in several hours under these conditions (data not shown).

Example 7

AcAmy1 Product Profile Analysis

To assay the products of fungal α-amylase catalysis of polysaccharides, amylases were incubated with three different substrates, DP7, amylopectin, and maltodextrin DE10 liquefact, at 50° C., pH 5.3 for 2 hours. The oligosaccharides released by the enzymes were analyzed via HPLC.

A final concentration of 10 ppm amylase was incubated with 0.5% (w/v) substrate in 50 mM pH 5.3 sodium citrate buffer containing 50 mM NaCl and 2 mM $CaCl_2$ for 120 min at 50° C. The reaction was then stopped by adding the same volume of ethanol and centrifuging 10 min at 14,000 rpm. The supernatant was diluted by a factor of 10 using MilliQ water, and 10 µL was loaded onto an HPLC column Aminex HPX-42A, 300 mm×7.8 mm, equipped with a refractive index detector. The mobile phase was MilliQ water, and the flow rate was 0.6 mL/min at 85° C.

Table 4 shows the profile of oligosaccharides saccharified by AcAmy1 and the AkAA benchmark for various substrates. Only oligosaccharides with DP1-DP7 are shown. The numbers in the Table reflect the weight percentage of each DPn as a fraction of the total DP1-DP7. The AcAmy1 produced mostly DP1 and DP2, with DP2 as the major product for all tested substrates. AcAmyl produced a composition of sugars containing at least 50% w/w DP2 relative to the combined amounts of DP1-DP7. AkAA, on the other hand, produced a product profile more evenly distributed from DP1 to DP4.

TABLE 4

Product profile of fungal alpha-amylases on three substrates.

| Enzyme | Substrate | Percent Oligosaccharides Product Composition | | | | | | |
|--------|-----------|-----|-----|-----|-----|-----|-----|-----|
|        |           | DP1 | DP2 | DP3 | DP4 | DP5 | DP6 | DP7 |
| AkAA   | DP7       | 15  | 27  | 41  | 17  | 0   | 0   | ND  |
|        | Amylopectin | 14 | 20 | 46  | 21  | 0   | 0   | 0   |
|        | DE10 Liquefact | 16 | 23 | 44 | 17 | 0   | 0   | 0   |
| AcAmyl | DP7       | 19  | 64  | 17  | 0   | 0   | 0   | ND  |
|        | Amylopectin | 24 | 56 | 9  | 1   | 4   | 5   | 2   |
|        | DE10 Liquefact | 24 | 58 | 9  | 1   | 3   | 3   | 2   |

Example 8

Liquefaction

AcAmyl was used to liquefy a 25% DS corn starch solution. 800 μg AcAmyl was added to the corn starch solution for 10 min at pH 5.8 and 85° C., and pH 4.5 and 95° C. Liquefying activity was assayed by an RVA viscometer test. Table 5 shows the reduction in viscosity by AcAmyl.

TABLE 5

Peak and final viscosity of corn flour during liquefaction in the presence of AcAmyl.

| pH 5.8/85° C. | | pH 4.5/95° C. | |
|---|---|---|---|
| Peak viscosity | Final viscosity | Peak viscosity | Final viscosity |
| 14560 | 120 | 14320 | 840 |

Example 9

SSF Ethanol Fermentation

The ability of AcAmyl to produce ethanol and reduce insoluble residual starch (IRS) were tested in SSF. The results show that AcAmyl can achieve comparable effects as AkAA but at a reduced dosage.

The liquefact was specially prepared to contain a relatively high amount of residual starch in the End of Fermentation (EOF) corn slurry to help differentiate performance in abating insoluble residual starch (IRS) and fouling by IRS. SSF was carried out with AkAA or AcAmyl in the presence of a *Trichoderma* glucoamylase variant having a DP7 performance index of at least 1.15 measured using FPLC (see U.S. Pat. No. 8,058,033 B2, Danisco US Inc.), according to the procedure below. After SSF, samples were analyzed for: (i) ethanol yield and DP3+ reduction using HPLC; and (ii) IRS using an iodine assay. The DP3+ levels are measured through the void volume, the reduction of which is commonly interpreted to reflect the efficiency of liquefact saccharification.

Liquefact Preparation: frozen liquefact (30% DS) was incubated overnight at 4° C., then put in water bath at 70° C. until completely thawed (1-3 hours). The liquefact temperature was adjusted to 32° C. The liquefact was weighed, and solid urea was added to 600 ppm. The pH of the liquefact was adjusted using 6N sulfuric acid or 28% ammonium hydroxide.

Fermentation: ETHANOL RED® (LeSaffre) yeast was used to convert glucose to ethanol. Dry yeast was added to 0.1% w/w to the liquefact batch, and the composition was mixed well and incubated for 30 minutes at room temperature. 100 g+/−0.2 g liquefact (32% DS) was weighed into individually labeled 150 mL Erlynmeyer flasks. Glucoamylase was added to each flask at varying dosages from 0.325 GAU/g solid, 0.2275 GAU/g solid, and 0.1625 GAU/g solid. AkAA or AcAmyl alpha-amylases were added to each flask at varying dosages, with the highest dosage at 20 rig protein/g solid (100% dose). The mixture was incubated in a forced air incubator with mixing at 200 rpm for 54 or 70 hours at pH 3.5 to 4.8, 32° C. About 1 mL EOF corn slurry samples were taken at approximately t=0, 3, 19, 23, 27, 43, 52, and/or 70 hours and stored frozen. The EOF samples were assayed for ethanol yield and DP3+ reduction, and IRS.

(i) Ethanol Yield and DP3+ Reduction

To determine the ethanol yield and DP3+ reduction, time point samples were thawed at 4° C. and centrifuged for 2 min at 15,000 rpm. 100 μL of the sample supernatants were mixed in individual microcentrifuge tubes with 10 μL of 1.1 N sulfuric acid and incubated 5 min at room temp. 1 mL of water was added to each tube, and the tubes were centrifuged for 1 min at 15,000 rpm. 200 μL were filtered onto an HPLC plate. The plate was analyzed on an Agilent HPLC using a Rezex Fast Fruit RFQ column with 8 min elution. Calibration curves for the above components were prepared using a Supelco Fuel Ethanol (Sigma Cat. 48468-U). DP1, DP2, DP3+, glycerol, acetic acid, lactic acid, and ethanol concentration (g/L) were determined using the ChemStation software. Ethanol production was converted to the percent v/v of the reaction mixture.

Rates of ethanol production obtained with AcAmyl and a glucoamylase at pH 4.8 were comparable to those obtained with AkAA and a glucoamylase (data not shown). Similar results were obtained at pH 3.5 and pH 3.8 for the rate and yield of ethanol production and DP3+ hydrolysis (data not shown). By 21 hours, ethanol yield was about 8% v/v for the control and AcAmyl as the α-amylase. Similar ethanol yields for both were also observed at around 48 hours. The rate of DP3+ hydrolysis, however, was noticeably improved using AcAmyl and glucoamylase. At 6 hr, DP3+(w/v) was reduced from 23% to about 8-9% by AcAmyl and glucoamylase, compared to about 14% for the control. The final amount of DP3+ at 48 hr was about 2% in both cases. The same results at pH 4.8 for ethanol yield and the rate and extent of DP3+ hydrolysis were obtained using less AcAmyl than AkAA (data not shown), indicating that AcAmyl can be used at a reduced dosage compared to AkAA.

(ii) Iodine-Positive Starch

The following procedure describes a method to qualitatively predict residual starch levels following conventional fermentation of corn liquefact by iodine staining of amylose. One gram of the EOF corn slurry was added to individually labeled microcentrifuge tubes. 200 μL of deionized water were added to each tube, then 20 μL of iodine solution was added to each tube and mixed thoroughly. The iodine solution (Lugol's Reagent) was prepared by dissolving 5 g iodine and 10 g potassium iodine in 100 mL water. Iodine stained tubes were ranked in order of increasing blue color. Samples staining blue/black contain the highest levels of residual starch.

Additionally, the commercially available Megazyme Total Starch protocol (Megazyme International, Ireland) was adapted to qualitatively measure residual starch levels following conventional fermentation of corn liquefact by iodine staining of amylose. About 800 mg of the EOF corn slurry and 0.2 mL of aqueous ethanol (80% v/v) were mixed in a glass tube by stirring on a vortex mixer. Then 3 mL of thermostable α-amylase (300 U) in 50 mM MOPS buffer, pH 7.0, were added, and the tube was vigorously stirred. The tube was incubated in a boiling water bath for 6 mM with vigorous stirring after 2 min and 4 min. After the tube was transferred to a bath of 50° C., 4 mL 200 mM sodium acetate buffer, pH 4.5, and 0.1 mL amyloglucosidase (20 U) were added. The tube was stirred on a vortex mixer and incubated at 50° C. for 30 mM Distilled water was added to each tube to bring up to a final volume of 10 mL. The mixture was transferred to 1.5 ml eppendorf tubes and centrifuged at 3,000 rpm for 10 min. If the starting EOF corn slurry contained 10-100% starch, the supernatant was diluted 10 times with distilled water. Duplicate aliquots (0.1 mL) of the supernatant or the diluted supernatant were transferred to the bottom of glass test tubes (16× 100 mm) About 3.0 mL of GOPOD Reagent were added to each tube, including the glucose controls and reagent blanks. The tubes were incubated at 50° C. for 20 min. The samples were transferred to 1.5 ml plastic cuvettes, and absorbance at 510 nm was measured for each sample within 60 minutes. The measured glucose amount for the EOF corn slurry was converted to the amount of residual starch.

Table 6 shows the residual starch level in the EOF corn slurry following SSF with AcAmy1 and AkAA. The residual starch was found to be about the same using 10 rig protein/g solid of AkAA (50% dose) and 3.3 rig protein/g solid for AcAmy1 (17% dose). Given the data, AcAmy1 appears at least three times more efficient than AkAA in removing residual starch.

TABLE 6

Residual starch analysis for SSF with AcAmy1 and AkAA.

|  | Dosage (µg protein/g solid) | Residual Starch (% w/v) |
| --- | --- | --- |
| AkAA | 10 | 0.85 ± 0.00 |
| AcAmy1 | 3.3 | 0.85 ± 0.04 |

What is claimed is:

1. A method of saccharifying a composition comprising starch to produce a composition comprising glucose, wherein said method comprises:
   (i) contacting said solution comprising starch with an isolated AcAmy1 or variant thereof having α-amylase activity comprising an amino acid sequence with at least 90% amino acid sequence identity to (a) residues 20-636 of SEQ ID NO:1 or (b) residues 20-497 of SEQ ID NO:1;
   (ii) saccharifying said solution comprising starch to produce said composition comprising glucose; wherein said isolated AcAmy1 or variant thereof catalyzes the saccharification of the starch solution to glucose; and
   (iii) fermenting the glucose composition to produce an End of Fermentation (EOF) product.

2. The method of claim 1, wherein said fermentation is a simultaneous saccharification and fermentation (SSF) reaction.

3. The method of claim 1, wherein said fermentation is conducted for 48-70 hours at pH 2-8 and in a temperature range of 25° C.-70° C.

4. The method of claim 1, wherein the EOF product comprises ethanol.

5. The method of claim 4, wherein the EOF product comprises 8%-18% (v/v) ethanol.

6. The method of claim 1, wherein said method further comprises contacting a mash and/or a wort with the AcAmy1 or variant thereof.

7. The method of claim 6, wherein said method further comprises:

(a) preparing a mash;
(b) filtering the mash to obtain a wort; and
(c) fermenting the wort to obtain a fermented beverage, wherein AcAmy1 or variant thereof are added to:
   (i) the mash of step (a) and/or
   (ii) the wort of step (b) and/or
   (iii) the wort of step (c).

8. The method of claim 1, wherein the EOF product comprises a metabolite.

9. The method of claim 8, wherein the metabolite is citric acid, lactic acid, succinic acid, monosodium glutamate, gluconic acid, sodium gluconate, calcium gluconate, potassium gluconate, glucono delta-lactone, sodium erythorbate, omega 3 fatty acid, butanol, an amino acid, lysine, itaconic acid, 1,3-propanediol, or isoprene.

10. The method of claim 1, further comprising adding glucoamylase, hexokinase, xylanase, glucose isomerase, xylose isomerase, phosphatase, phytase, pullulanase, β-amylase, α-amylase that is not AcAmy1, protease, cellulase, hemicellulase, lipase, cutinase, isoamylase, redox enzyme, esterase, transferase, pectinase, alpha-glucosidase, beta-glucosidase, or a combination thereof, to said starch solution.

11. The method of claim 10, wherein said glucoamylase is added to 0.1-2 glucoamylase units (GAU)/g ds.

12. The method of claim 1, wherein said isolated AcAmy1 or a variant thereof is expressed and secreted by a host cell.

13. The method of claim 12, wherein said composition comprising starch is contacted with said host cell.

14. The method of claim 12, wherein the host cell further expresses and secretes a glucoamylase.

15. The method of claim 12, wherein the host cell is capable of fermenting the glucose composition.

* * * * *